(12) United States Patent
DePasqua et al.

(10) Patent No.: US 12,350,416 B2
(45) Date of Patent: *Jul. 8, 2025

(54) METHODS OF AMELIORATION OF CEREBROSPINAL FLUID AND DEVICES AND SYSTEMS THEREFOR

(71) Applicant: EnClear Therapies, Inc., Newburyport, MA (US)

(72) Inventors: Anthony DePasqua, Newburyport, MA (US); Kevin Eggan, Jr., Boston, MA (US); Kevin Kalish, Newburyport, MA (US); Manual A. Navia, Lexington, MA (US); Kasper Roet, Somerville, MA (US); Ching-Hua Tseng, Belmont, MA (US); Alan D. Watson, Lexington, MA (US); William X. Siopes, Lowell, MA (US); Gianna N. Riccardi, South Berwick, ME (US); Marcie Ann Glicksman, Salem, MA (US)

(73) Assignee: EnClear Therapies, Inc., Newburyport, MA (US)

( * ) Notice: Subject to any disclaimer, the term of this patent is extended or adjusted under 35 U.S.C. 154(b) by 684 days.

This patent is subject to a terminal disclaimer.

(21) Appl. No.: 17/669,883

(22) Filed: Feb. 11, 2022

(65) Prior Publication Data

US 2022/0160947 A1    May 26, 2022

Related U.S. Application Data

(63) Continuation of application No. 17/062,440, filed on Oct. 2, 2020, now Pat. No. 11,278,657, which is a
(Continued)

(51) Int. Cl.
*A61M 1/36* (2006.01)
*A61M 1/16* (2006.01)
*A61M 27/00* (2006.01)

(52) U.S. Cl.
CPC ............ *A61M 1/3687* (2013.01); *A61M 1/16* (2013.01); *A61M 1/1601* (2014.02);
(Continued)

(58) Field of Classification Search
CPC ........ A61M 27/006; A61M 2027/0004; A61M 2202/0464; A61M 1/14; A61M 1/34; A61M 1/36
See application file for complete search history.

(56) References Cited

U.S. PATENT DOCUMENTS 3,929,992 A    12/1975   Sehgal et al.
4,316,885 A    2/1982    Rakhit
(Continued)

FOREIGN PATENT DOCUMENTS

EP    1481697 A1    12/2004
EP    1731182 A1    12/2006
(Continued)

OTHER PUBLICATIONS

Extended European Search Report for European Application No. 19839881.0 dated Jun. 21, 2022, 9 pages.
(Continued)

*Primary Examiner* — Leslie R Deak
(74) *Attorney, Agent, or Firm* — Nutter, McClennen & Fish, LLP

(57) ABSTRACT

Cerebrospinal fluid (CSF) and other fluid amelioration systems completely or partially implantable within a mammalian subject and associated methods include a substrate and an agent for amelioration of a toxic biomolecule present in the CSF or fluid, wherein the agent is disposed on or within the substrate.

21 Claims, 26 Drawing Sheets

Related U.S. Application Data continuation of application No. PCT/US2020/027683, filed on Apr. 10, 2020.

(60) Provisional application No. 62/960,861, filed on Jan. 14, 2020, provisional application No. 62/832,486, filed on Apr. 11, 2019.

(52) U.S. Cl.
CPC ......... *A61M 27/006* (2013.01); *A61M 1/3655* (2013.01); *A61M 1/3659* (2014.02); *A61M 2027/004* (2013.01); *A61M 2202/0464* (2013.01); *A61M 2205/103* (2013.01); *A61M 2205/12* (2013.01); *A61M 2205/3334* (2013.01); *A61M 2205/3344* (2013.01); *A61M 2205/3379* (2013.01); *A61M 2210/1003* (2013.01); *A61M 2210/1039* (2013.01)

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,382,445 A | 5/1983 | Sommers |
| 4,517,288 A | 5/1985 | Giegel et al. |
| 4,650,803 A | 3/1987 | Stella et al. |
| 4,655,745 A | 4/1987 | Corbett |
| 4,830,849 A | 5/1989 | Osterholm |
| 4,837,168 A | 6/1989 | de Jaeger et al. |
| 4,950,232 A | 8/1990 | Ruzicka et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,162,333 A | 11/1992 | Failli et al. |
| 5,177,203 A | 1/1993 | Failli et al. |
| 5,221,670 A | 6/1993 | Caufield |
| 5,233,036 A | 8/1993 | Hughes |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,405,316 A | 4/1995 | Magram |
| 5,411,967 A | 5/1995 | Kao et al. |
| 5,434,260 A | 7/1995 | Skotnicki et al. |
| 5,463,048 A | 10/1995 | Skotnicki et al. |
| 5,470,318 A | 11/1995 | Griffith, III et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,531,673 A | 7/1996 | Helenowski |
| 5,563,145 A | 10/1996 | Failli et al. |
| 5,665,772 A | 9/1997 | Cottens et al. |
| 5,780,462 A | 7/1998 | Lee et al. |
| 5,957,912 A | 9/1999 | Heitzmann |
| 6,193,691 B1 | 2/2001 | Beardsley |
| 6,210,346 B1 | 4/2001 | Hall et al. |
| 6,273,913 B1 | 8/2001 | Wright et al. |
| 6,277,983 B1 | 8/2001 | Shaw et al. |
| 6,358,969 B1 | 3/2002 | Shelley et al. |
| 6,471,960 B1 | 10/2002 | Anderson |
| 6,585,764 B2 | 7/2003 | Wright et al. |
| 6,599,275 B1 | 7/2003 | Fischer, Jr. |
| 6,670,168 B1 | 12/2003 | Katz et al. |
| 6,689,085 B1 | 2/2004 | Rubenstein et al. |
| 6,696,488 B2 | 2/2004 | Wolfe et al. |
| 6,808,536 B2 | 10/2004 | Wright et al. |
| 6,916,310 B2 | 7/2005 | Sommerich |
| 7,025,739 B2 | 4/2006 | Saul |
| 7,037,288 B2 | 5/2006 | Rosenberg et al. |
| 7,331,940 B2 | 2/2008 | Sommerich |
| 7,662,140 B2 | 2/2010 | Heruth et al. |
| 7,717,871 B2 | 5/2010 | Odland |
| 7,763,142 B2 | 7/2010 | Watson |
| 7,887,503 B2 | 2/2011 | Geiger |
| 8,088,091 B2 | 1/2012 | Thomas et al. |
| 8,137,334 B2 | 3/2012 | Heruth et al. |
| 8,206,334 B2 | 6/2012 | Kralick et al. |
| 8,216,173 B2 | 7/2012 | Dacey, Jr. et al. |
| 8,292,856 B2 | 10/2012 | Bertrand et al. |
| 8,435,204 B2 | 5/2013 | Lad et al. |
| 9,097,723 B2 | 8/2015 | Fathollahi et al. |
| 9,138,537 B2 | 9/2015 | Miesel |
| 9,220,424 B2 | 12/2015 | Wilson et al. |
| 9,421,348 B2 | 8/2016 | Lenihan et al. |
| 9,603,792 B2 | 3/2017 | John |
| 9,629,987 B2 | 4/2017 | Anand et al. |
| 9,682,193 B2 | 6/2017 | Anand et al. |
| 9,687,670 B2 | 6/2017 | Dacey, Jr. et al. |
| 9,744,338 B2 | 8/2017 | East et al. |
| 9,770,180 B2 | 9/2017 | Radojicic |
| 9,895,518 B2 | 2/2018 | Lad et al. |
| 9,919,138 B2 | 3/2018 | Lenihan et al. |
| 10,258,781 B2 | 4/2019 | Choi et al. |
| 10,272,188 B1 | 4/2019 | Geiger et al. |
| 10,441,770 B2 | 10/2019 | Singh et al. |
| 10,549,035 B2 | 2/2020 | Hayek |
| 10,653,713 B2 | 5/2020 | Thakker et al. |
| 10,695,484 B1 | 6/2020 | Radojicic |
| 10,864,323 B2 | 12/2020 | Gerrans |
| 11,278,657 B2 * | 3/2022 | DePasqua ........... A61M 1/1601 |
| 11,534,592 B2 | 12/2022 | Singh et al. |
| 2002/0004580 A1 | 1/2002 | Fueyo et al. |
| 2002/0025521 A1 | 2/2002 | Lu et al. |
| 2003/0060436 A1 | 3/2003 | Schneider |
| 2003/0135148 A1 | 7/2003 | Dextradeur et al. |
| 2004/0068241 A1 | 4/2004 | Fischer |
| 2004/0110250 A1 | 6/2004 | Wischik et al. |
| 2004/0138153 A1 | 7/2004 | Ramesh et al. |
| 2004/0185042 A1 | 9/2004 | Scheiflinger et al. |
| 2004/0220510 A1 | 11/2004 | Koullick et al. |
| 2004/0236309 A1 | 11/2004 | Yang |
| 2006/0025726 A1 | 2/2006 | Fischer et al. |
| 2006/0074388 A1 | 4/2006 | Dextradeur et al. |
| 2006/0079740 A1 | 4/2006 | Silver et al. |
| 2006/0264897 A1 | 11/2006 | Lobl et al. |
| 2007/0167867 A1 | 7/2007 | Wolf |
| 2007/0173787 A1 | 7/2007 | Huang et al. |
| 2007/0243179 A1 | 10/2007 | Elia |
| 2008/0082036 A1 | 4/2008 | Trescony et al. |
| 2008/0242590 A1 | 10/2008 | Andersson et al. |
| 2009/0131857 A1 | 5/2009 | Geiger |
| 2010/0030196 A1 | 2/2010 | Hildebrand et al. |
| 2010/0234792 A1 | 9/2010 | Dacey, Jr. et al. |
| 2011/0033463 A1 | 2/2011 | Thakker et al. |
| 2012/0238835 A1 | 9/2012 | Hyde et al. |
| 2012/0238936 A1 | 9/2012 | Hyde et al. |
| 2013/0197422 A1 | 8/2013 | Browd et al. |
| 2013/0273203 A1 | 10/2013 | Oestergaard et al. |
| 2014/0018257 A1 | 1/2014 | Suga et al. |
| 2014/0206102 A1 | 7/2014 | Petrucelli et al. |
| 2014/0303455 A1 | 10/2014 | Shachar et al. |
| 2014/0377319 A1 | 12/2014 | Leuthardt et al. |
| 2015/0005800 A1 | 1/2015 | Anile |
| 2015/0094644 A1 | 4/2015 | Lenihan et al. |
| 2015/0201882 A1 | 7/2015 | Swoboda et al. |
| 2015/0374898 A1 | 12/2015 | Fujieda et al. |
| 2016/0002627 A1 | 1/2016 | Bennett et al. |
| 2016/0025747 A1 | 1/2016 | Ranum et al. |

(56) References Cited

U.S. PATENT DOCUMENTS

| | | |
|---|---|---|
| 2016/0089521 A1 | 3/2016 | Dragoon et al. |
| 2016/0183819 A1 | 6/2016 | Burnett et al. |
| 2016/0361365 A1 | 12/2016 | Lee et al. |
| 2017/0059586 A1 | 3/2017 | Petrucelli et al. |
| 2017/0095649 A1 | 4/2017 | Vase et al. |
| 2017/0137492 A1 | 5/2017 | Looby |
| 2017/0157038 A1 | 6/2017 | Peyman |
| 2017/0157374 A1 | 6/2017 | Hedstrom et al. |
| 2017/0203084 A1 | 7/2017 | Lad et al. |
| 2017/0313687 A1 | 11/2017 | Hendrickson et al. |
| 2018/0028746 A1 | 2/2018 | Abrams et al. |
| 2018/0185058 A1 | 7/2018 | Anand et al. |
| 2018/0371010 A1 | 12/2018 | Vassylyev et al. |
| 2019/0009014 A1 | 1/2019 | Chen et al. |
| 2019/0048371 A1 | 2/2019 | Basheer et al. |
| 2019/0083303 A1 | 3/2019 | Khanna |
| 2019/0085336 A1 | 3/2019 | Zhu et al. |
| 2019/0089521 A1 | 3/2019 | Coulthard et al. |
| 2019/0317099 A1 | 10/2019 | Halbert et al. |
| 2020/0001059 A1 | 1/2020 | Campbell et al. |
| 2020/0046952 A1 | 2/2020 | Vase |
| 2020/0046954 A1 | 2/2020 | Lad et al. |
| 2020/0324006 A1 | 10/2020 | Paul et al. |
| 2020/0330497 A1 | 10/2020 | Marcotulli et al. |
| 2021/0023293 A1 | 1/2021 | DePasqua et al. |
| 2021/0033620 A1 | 2/2021 | Porter et al. |
| 2021/0077016 A1 | 3/2021 | Bodner |
| 2021/0145944 A1 | 5/2021 | Navia et al. |
| 2021/0154276 A1 | 5/2021 | Navia et al. |
| 2021/0162173 A1 | 6/2021 | Singh et al. |
| 2022/0096743 A1 | 3/2022 | Riccardi et al. |
| 2022/0096744 A1 | 3/2022 | Riccardi et al. |
| 2022/0096745 A1 | 3/2022 | Riccardi et al. |
| 2022/0105322 A1 | 4/2022 | Riccardi et al. |
| 2022/0134076 A1 | 5/2022 | Bodner |
| 2022/0257854 A1 | 8/2022 | Bodner et al. |
| 2022/0313890 A1 | 10/2022 | Riccardi et al. |
| 2022/0355015 A1 | 11/2022 | Patel et al. |
| 2022/0370716 A1 | 11/2022 | Martin et al. |
| 2022/0379010 A1 | 12/2022 | Martin et al. |
| 2022/0401645 A1 | 12/2022 | Morse et al. |
| 2023/0001165 A1 | 1/2023 | Bourouiba et al. |
| 2023/0056486 A1 | 2/2023 | Navia et al. |

FOREIGN PATENT DOCUMENTS

| | | |
|---|---|---|
| EP | 3294398 A1 | 3/2018 |
| EP | 3833251 A1 | 6/2021 |
| EP | 4030988 A1 | 7/2022 |
| WO | 98/02441 A2 | 1/1998 |
| WO | 99/13886 A1 | 3/1999 |
| WO | 99/15530 A1 | 4/1999 |
| WO | 2000/056335 A1 | 9/2000 |
| WO | 01/14387 A1 | 3/2001 |
| WO | 2001/039819 A2 | 6/2001 |
| WO | 2003015710 A2 | 2/2003 |
| WO | 03/057218 A1 | 7/2003 |
| WO | 2003/015710 A3 | 2/2004 |
| WO | 2004/058337 A1 | 7/2004 |
| WO | 2004/091444 A2 | 10/2004 |
| WO | 2008/105959 A2 | 9/2008 |
| WO | 2010123558 A1 | 10/2010 |
| WO | 2011114260 A1 | 9/2011 |
| WO | 2014/159247 A1 | 10/2014 |
| WO | 2015/049588 A2 | 4/2015 |
| WO | 2014/124365 A3 | 10/2015 |
| WO | 2016183123 A1 | 11/2016 |
| WO | 2017096228 A1 | 6/2017 |
| WO | 2018005621 A1 | 1/2018 |
| WO | 2019/028006 A1 | 2/2019 |
| WO | 2019/100074 A1 | 5/2019 |
| WO | 2020/023417 A1 | 1/2020 |
| WO | 2020/023418 A1 | 1/2020 |
| WO | 2020/033773 A1 | 2/2020 |
| WO | 2020064875 A1 | 4/2020 |
| WO | 2020/0149993 A1 | 7/2020 |
| WO | 2020/210634 A1 | 10/2020 |
| WO | 2021/055100 A1 | 3/2021 |
| WO | 2022/173620 A1 | 8/2022 |
| WO | 2022/246042 A1 | 11/2022 |

OTHER PUBLICATIONS

Extended European Search Report for European Application No. 19840444.4 dated Jun. 28, 2022, 7 pages.

International Search Report and Written Opinion for International Application No. PCT/US2021/052735, mailed Feb. 11, 2022, 28 pages.

International Search Report and Written Opinion for International Application No. PCT/US2021/053829 mailed Jan. 13, 2022. 19 pages.

International Searching Authority, International Search Report for International Application No. PCT/US2022/037609, dated Oct. 26, 2022, together with the Written Opinion of the International Searching Authority, 8 pages.

International Searching Authority, International Search Report for International Application No. PCT/US22/34706, dated Oct. 18, 2022, together with the Written Opinion of the International Searching Authority, 8 pages.

Kim Kwang Soo, et al., "Proteolytic Cleavage of Extracellular a-Synuclein by Plasmin: Implications for Parkinson Disease" Journal of Biological Chemistry, vol. 287, No. 30, Mar. 22, 2012, pp. 24862-24872.

Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.

Saido, T., et al., "Proteolytic Degradation of Amyloid 13-Protein" Cold Spring Harbor Perspectives in Medicine, vol. 2, No. 6, Jun. 1, 2012, pp. a006379-a006379.

Spencer, B., et al., "Lentivirus Mediated Delivery of Neurosin Promotes Clearance of Wild-type a-Synuclein and Reduces the Pathology in an a-Synuclein Model of LBD", Molecular Therapy, vol. 21, No. 1, Jan. 1, 2013, pp. 31-41.

Tanji, K., et al., "Proteinase K-resistant a-synuclein is deposited in presynapses in human Lewy body disease and A53T a-synuclein transgenic mice," Acta Neuropathologica, Springer, Berlin, DE, vol. 120, No. 2, Mar. 26, 2010, pp. 145-154.

Neumann, M., et al., "Ubiquitinated TDP-43 in frontotemporal lobar degeneration and amyotrophic lateral sclerosis," Science, vol. 314, 2006, pp. 130-133.

Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.

Ozcelik, A., et al., "Acoustic tweezers for the life sciences," Nature Methods vol. 15, 2018, pp. 1021-1028.

Paraskevas,G., et al., "The emerging TDP-43 proteinpathy" Neuroimmunol Neuroinflammation 5:17 (Year 2018).

Pardridge, W., et al., "CSF, blood-brain barrier, and brain drug delivery," Expert Opinion on Drug Delivery, vol. 13, 2016, pp. 1-13.

Patel, A., et al., "Identification and enumeration of circulating tumor cells in the cerebrospinal fluid of breast cancer patents with central nervous system metastases," Oncotarget, vol. 2, No. 10, 2011, pp. 752-760.

Paulson, H., et al., "Genetics of Dementia," Seminars in Neurology, vol. 31, pp. 449-360.

Phukan, J., et al., "Cognitive impairment in amyotrophic lateral sclerosis," The Lancet Neurology, vol. 6, Issue 11, pp. 994-1003.

Poreba, M., et al., "Current Strategies for Probing Substrate Specificity of Proteases," Current Medicinal Chemistry, vol. 17, Issue 33, 2010, pp. 3968-3995.

Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.

Reinhard, M., et al., "Blood-Brain Barrier Disruption by Low-Frequency Ultrasound," Stroke, vol. 37, 2006, pp. 1546-1548.

(56) References Cited

OTHER PUBLICATIONS

Renton, A., et al., "A Hexanucleotide Repeat Expansion in C9orF72 Is the Cause of Chromosome 9p21-Linked ALS-FTD," Neuron, vol. 27, Issue 2, pp. 257-268.
Sonabend, A., et al., "Overcoming the Blood-Brain Barrier with an Implantable Ultrasound Device," Clinical Cancer Research, vol. 25, Issue 13, 2019, pp. 3750-3752.
Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Steele, J., et al., "Progressive Supranuclear Palsy a Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
Takalo, M., et al., "Protein aggregation and degradation mechanisms in neurodegenerative diseases," American Journal of Neurodegenerative Disease, 2013; 2(1), pp. 1-14.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency, Ultrasound," PLOS One vol. 3, Issue 10, 2008, e3511, 11 pages.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N-terminally cleaved tau containing four microtubule?binding repeats," Journal of Neurochemistry, vol. 105, 2008, pp. 2343-2352.
Written Opinion of the International Preliminary Examining Authority for International Application No. PCT/US2019/042879, mailed Feb. 25, 2021 (6 pages).
Written Opinion of the International Preliminary Examining Authority for International Application No. PCT/US2019/042880, mailed Sep. 11, 2020 (8 pages).
Wszolek, Z., et al., "Frontotemporal dementia and parkinsonism linked to chromosome 17 (FTDP-17)" Orphanet Journal of Rare Diseases, 2006, 1:30, pp. 1-9.
Xie, L., et al., "Sleep Drives Metabolite Clearance from the Adult Brain," Science vol. 342, Issue 6156, 2013, pp. 373-377.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.
Abbott, N., et al., "The role of brain barriers in fluid movement in the CNS: is there a 'glymphatic' system?" Acta Neuropathologica vol. 135, 2018, pp. 387-407.
Allen, J., et al., "Abstract 3483: Modeling circulating tumor cells in the peripheral blood and CSF of breast cancer patients," Cancer Research vol. 73, Issue 8, 2013, abstract only.
Allen, J., et al., "Abstract 5565: Circulating tumor cells in the peripheral blood and cerebrospinal fluid of patients with central nervous system metastases," Cancer Research vol. 72, Issue 8, 2012, abstract only.
Andersen, P., et al., "Clinical genetics of amyotrophic lateral sclerosis: what do we really know?" Nature Reviews Neurology, vol. 7, 2011, pp. 603-615.
Arai, T., et al., "Phosphorylated and cleaved TDP?43 in ALS, FTLD and other neurodegenerative disorders and in cellular models of TDP?43 proteinopathy," Neuropathology, vol. 30, 2010, pp. 170-181.
Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.
Arriagada, P., et al., "Neurofibrillary tangles but not senile plaques parallel duration and severity of Alzheimer's disease," Neurology 42, 1992, pp. 631-639.
Asai, D., et al., "Chapter 3 Making Monoclonal Antibodies," Methods in Cell Biology, vol. 37, 1993, pp. 57-74.
Bioline "Proteinase K" accessed from bioline.com on Jun. 22, 2021 (Year: 2013).
Brat, D., et al., "Tau?associated neuropathology in ganglion cell tumours increases with patient age but appears unrelated to ApoE genotype," Neuropathy and Applied Neurobiology, vol. 27, Issue 3, 2001, pp. 197-205.
Buee, L., et al., "Tau protein isoforms, phosphorylation and role in neurodegenerative disorders," Brain Research Reviews, vol. 33, Issue 1, 2000, pp. 95-130.
Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.
Coatti, G., et al., "Pericytes Extended Survival of ALS SOD1 Mice and Induce the Expression of Antioxidant Enzymes in the Murine Model and in IPSCs Dervised Neuronal Cells from an ALS Patient," Stem Cell Reviews and Reports (2017) 13: 686-698.
De Souza, P., et al., "A biotechnology perspective of fungal proteases," Brazilian Journal of Microbiology, vol. 46, 2, 2015, pp. 337-346.
DeJesus-Hernandez, M., et al., "Expanded GGGGCC Hexanucleotide Repeat in Noncoding Region of C9orF72 Causes Chromosome 9p-Linked FTD and ALS," Neuron, vol. 72, 2011, pp. 245-256.
Diamond, S., "Methods for mapping protease specificity," Current Opinion in Chemical Biology, vol. 11, Issue 1, 2007, pp. 46-51.
Evidente, V., et al., "Post-encephalitic parkinsonism," Journal of Neurology, Neurosurgery & Psychiatry, vol. 63, Issue 1, 1998, pp. 5.
Finsterer, J., et al., "Liquorpheresis (CSF filtration) in familial amyotrophic lateral sclerosis," Spinal Cord, vol. 39, 1999, pp. 592-593.
Giannakopoulos, P., et al., Tangle and neuron numbers, but not amyloid load, predict cognitive status in Alzheimer's disease, Neurology, vol. 60, 2003, pp. 1495-1500.
Giordana, M., et al., "Dementia and cognitive impairment in amyotrophic lateral sclerosis: a review," Neurological Sciences, vol. 32, 2011, pp. 9-16.
Gomez-Isla, T., et al., Neuronal loss correlates with but exceeds neurofibrillary tangles in Alzheimer's disease, Annals of Neurology, vol. 41, 1997, pp. 17-24.
Grad, L., et al., "Prion-like activity of Cu/Zn superoxide dismutase: implications for amyotrophic lateral sclerosis," 8:1, 2014, pp. 33-41.
Graff-Radford, N., et al., "Frontotemporal dementia," Seminars in Neurology vol. 27, 2007, pp. 48-57.
Hasegawa, M., et al., "Molecular Dissection of TDP-43 Proteinopathies," Journal of Molecular Neuroscience, vol. 45, 2011, pp. 480-485.
Hasegawa, M., et al., "Phosphorylated TDP-43 in frontotemporal lobar degeneration and amyotrophic lateral sclerosis," Annals of Neurology, vol. 62, Issue 1, 2008, pp. 60-70.
Hersh, D., et al., "MR-guided transcranial focused ultrasound safely enhances interstitial dispersion of large polymeric nanoparticles in the living brain," PLOS One 13(2): e0192240, 2018, 19 pages.
Indivero, V., "Technique filters cancer where chemo can't reach: A new therapy may help cancer patients with malignant ce4lls near the spinal cord and in the brain," dated Jul. 30, 2013. Retrieved from the internet under https://news.psu.edu/story/282970/2013/07/30/research/technique-filters-cancer-where-chemo-cant-reach, 4 pages.
International Preliminary Report on Patentability for International Application No. PCT/US2019/042880, mailed Jan. 21, 2021 (8 pages).
International Preliminary Report on Patentability for International Application No. PCT/US2020/027683, mailed Oct. 21, 2021 (11 pages).
International Search Report and Written Opinion for International Application No. PCT/US2019/042879, mailed Oct. 8, 2019 (14 pages).
International Search Report and Written Opinion for International Application No. PCT/US2019/042880, mailed Oct. 16, 2019 (10 pages).

(56) References Cited

OTHER PUBLICATIONS

International Search Report and Written Opinion for International Application No. PCT/US2020/027683, mailed Aug. 6, 2020 (19 pages).
International Search Report and Written Opinion for International Application No. PCT/US2021/013458, mailed Jun. 9, 2021 (20 pages).
Jessen, N., et al., "The Glymphatic System—A Beginner's Guide," Neurochemical Research, 2015, 40(2), pp. 2583-2599.
Kaufman, S., et al., "Prion-Like Propagatio of Protein Aggregation and Related Therapeutic Strategies," Neurotherapeutics, 10, 2013, pp. 371-382.
Kopeikina, K., et al., "Soluble forms of tau are toxic in Alzheimer's disease," Translational Neuroscience 3(3), 2012, pp. 223-233.
Kouzehgarani, G., et al., "Harnessing cerebrospinal fluid circulation for drug delivery to brain tissues, Advanced Drug Delivery Reviews," 2021, vol. 173, pp. 20-59.
Lee, V., et al., "Neurodegenerative tauopathies," Annual Review of Neuroscience, vol. 24, 2001, pp. 1121-1159.
Legon, W., et al., "Transcranial focused ultrasound modulates the activity of primary somatosensory cortex in humans," Nature Neuroscience vol. 17, No. 2, 2014, pp. 322-329.
Lei, P., et al., "Tau protein: relevance to Parkinson's disease," The International Journal of Biochemistry & Cell Biology, vol. 42, Issue 11, 2010, pp. 1775-1778.
Lin, Z., et al., "Facile synthesis of enzyme-inorganic hybrid nanoflowers and their application as an immobilized trypsin reactor for highly efficient protein digestion." (Communication) RSC Adv., 2014, 4, 13888-13891.
Lipsman, N., et al., "Blood-brain barrier opening in Alzheimer's disease using MR-guided focused ultrasound," Nature Communications vol. 9, Article 2336, 2018, pp. 1-8.
Lomen-Hoerth, C., et al., "The overlap of amyotrophic lateral sclerosis and frontotemporal dementia," Neurology, vol. 59, 2002, pp. 1077-1079.
Martin, L., et al., "Post-translational modifications of tau protein: implications for Alzheimer's disease," Neurochemistry International, vol. 58, Issue 4, pp. 458-471.
Marx, S., et al., "Bench to Bedside: The Development of Rapamycin and Its Application to Stent Restenosis", Journal of the American Heart Association 104, 2001, pp. 852-855.
May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.
McKee, A., et al., "The Neuropathology of Chronic Traumatic Encephalopathy," Brain Pathology 253), 2015, pp. 350-364.
McRae et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, pp. 7196-7206.
Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.
Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.

\* cited by examiner

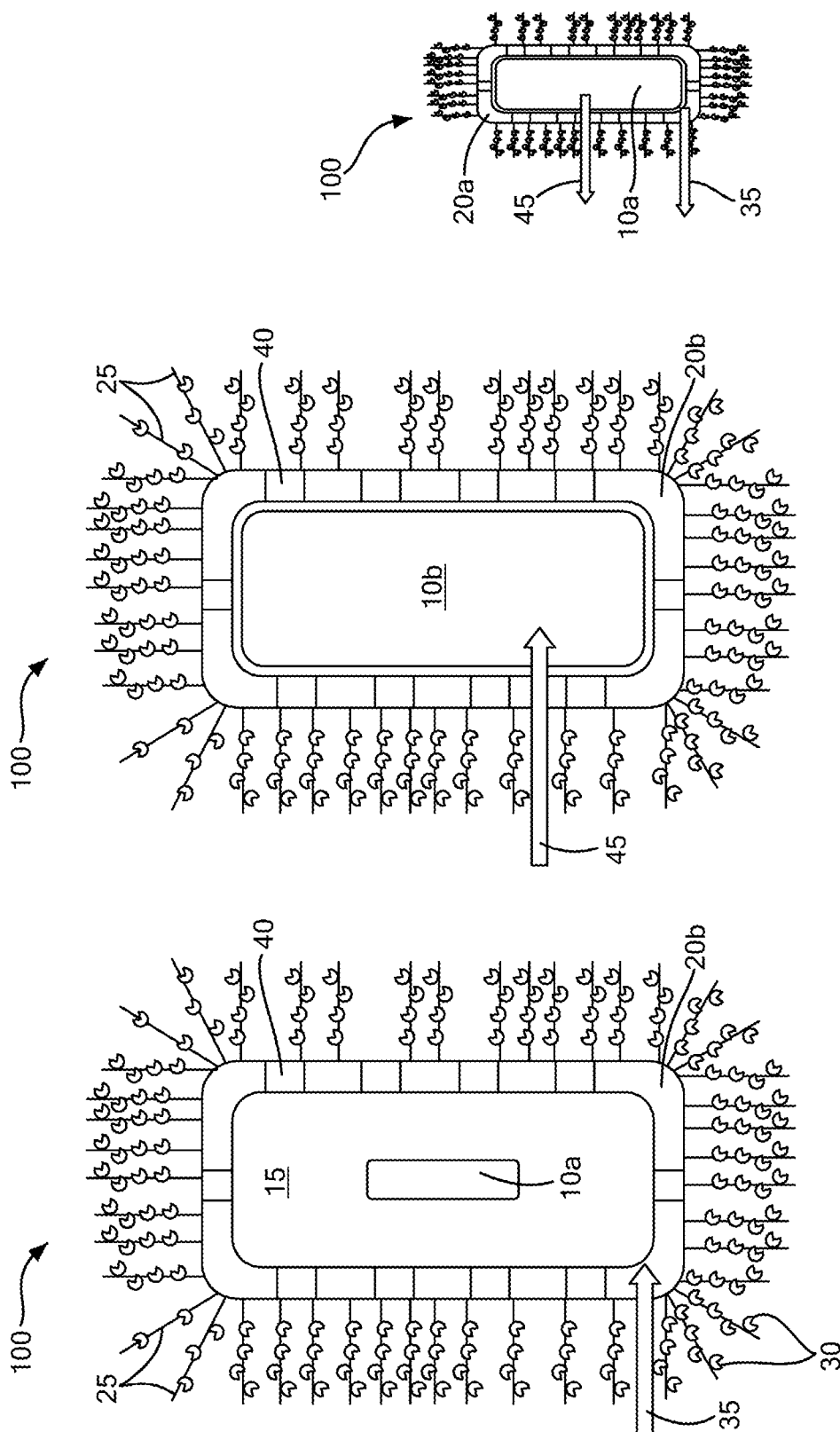

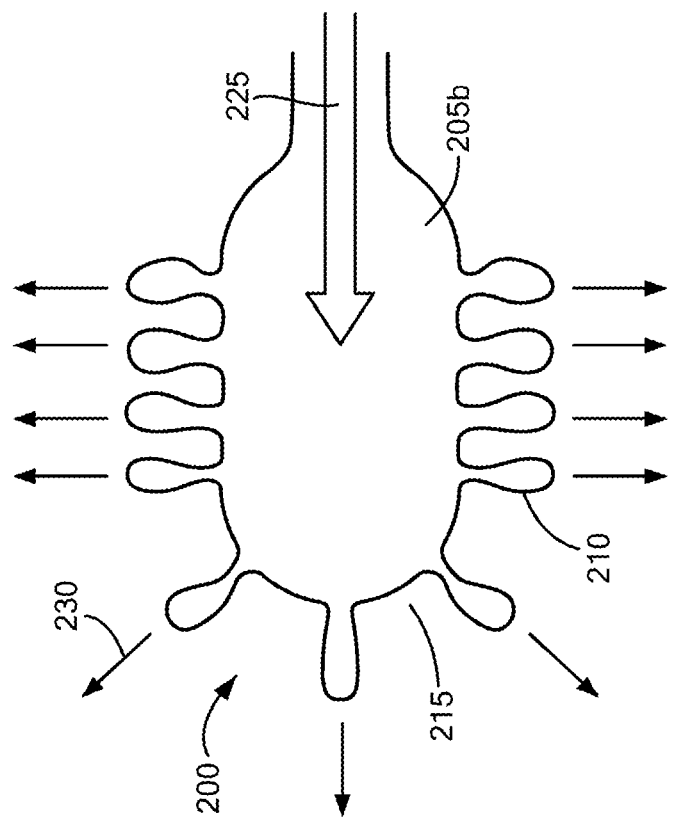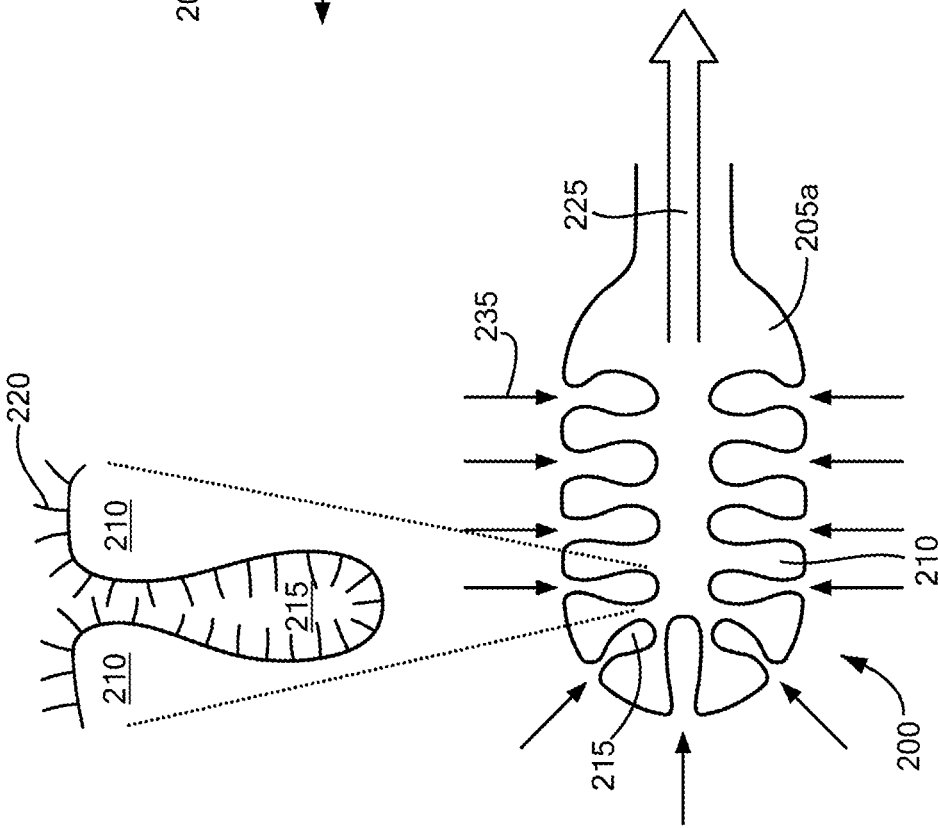

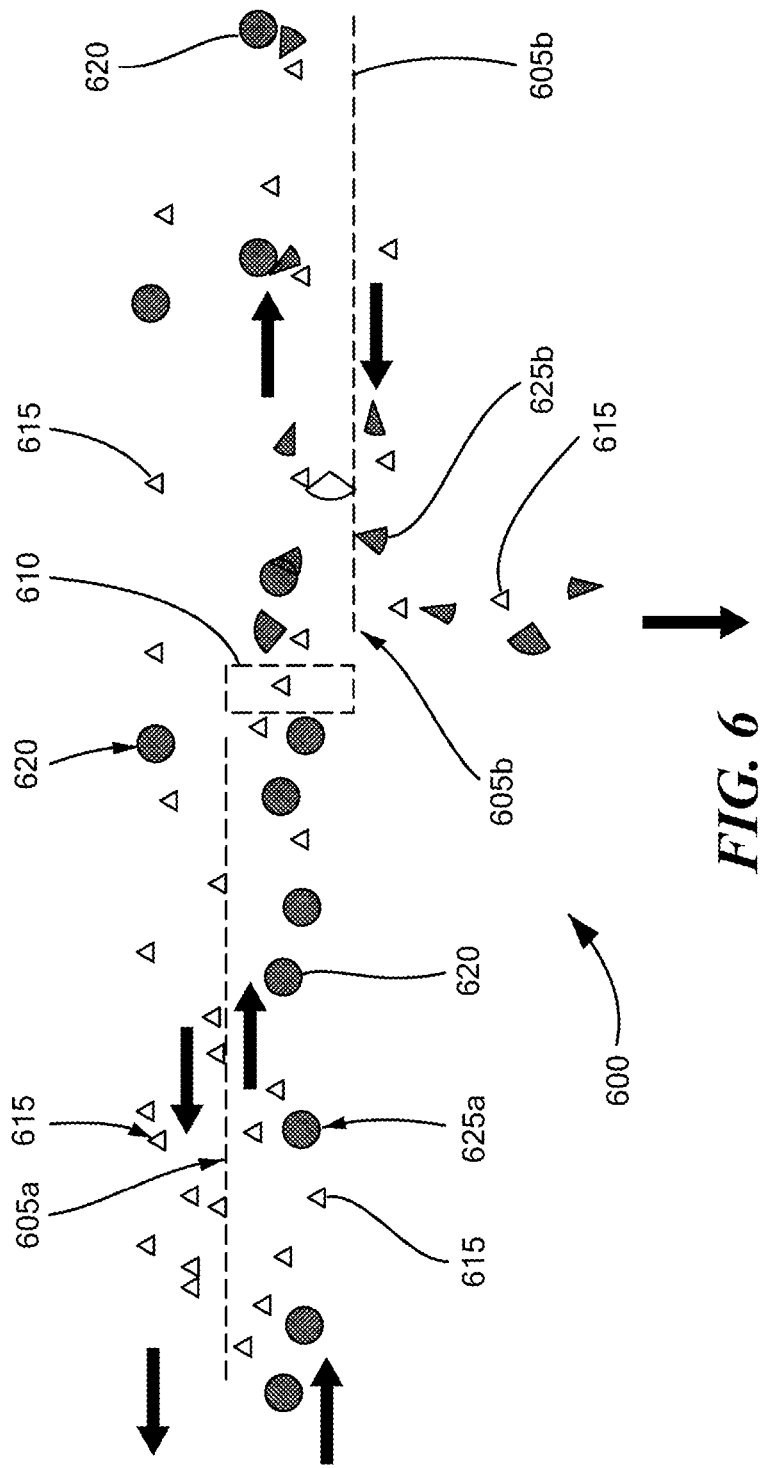

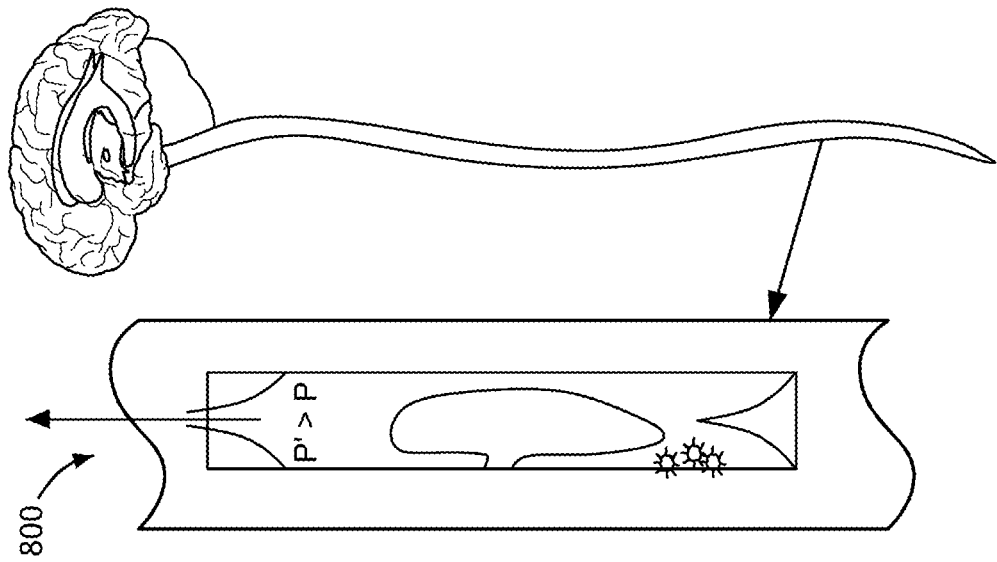
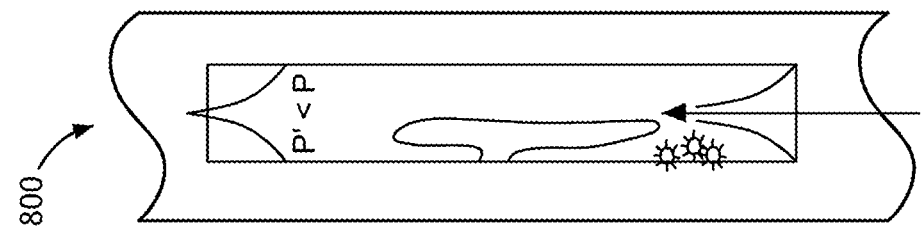
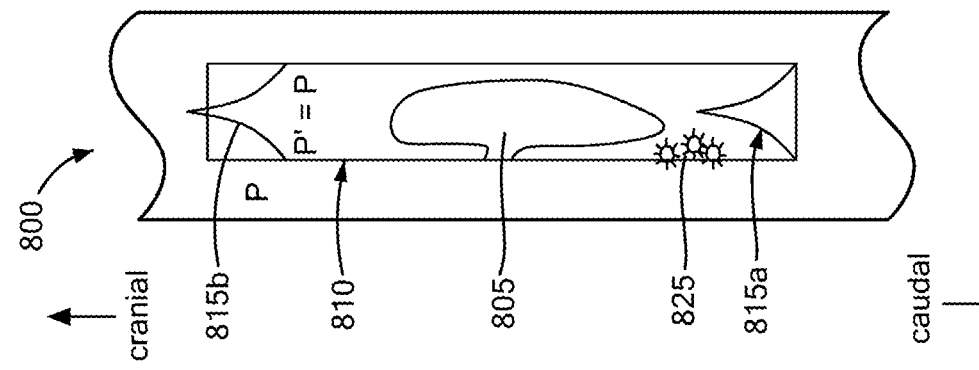
FIG. 8C
FIG. 8B
FIG. 8A

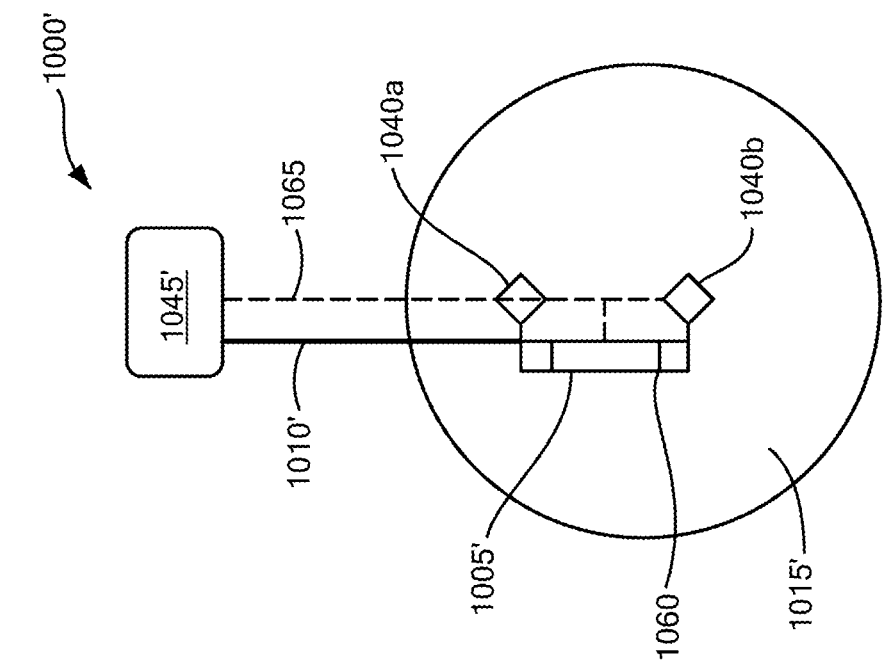
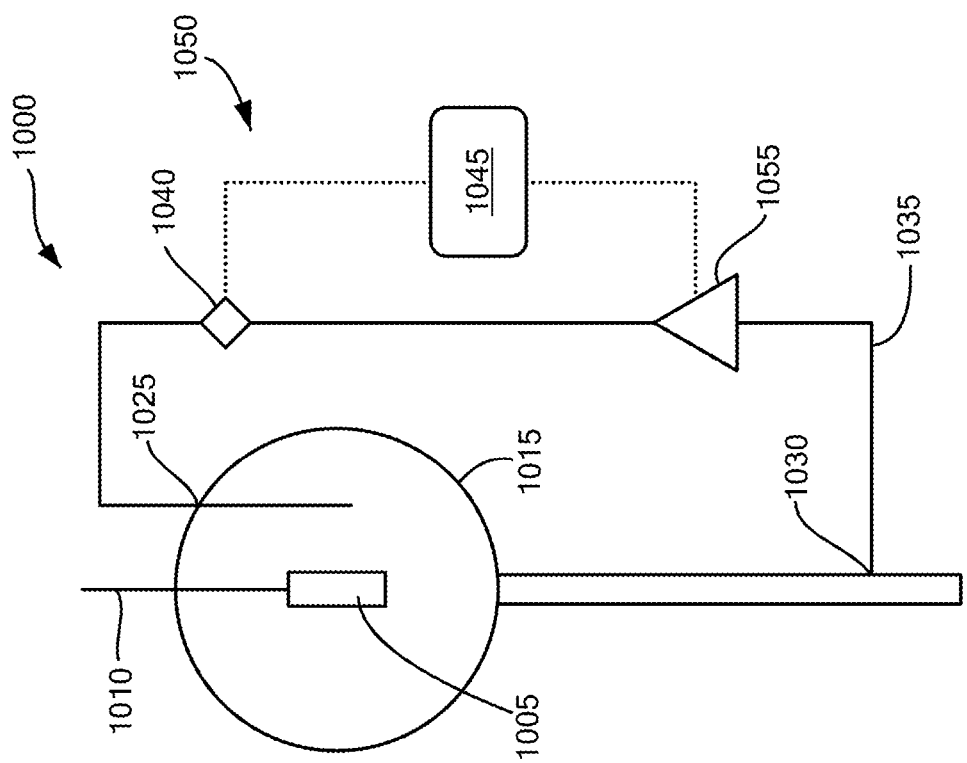
FIG. 10B
FIG. 10A

METHODS OF AMELIORATION OF CEREBROSPINAL FLUID AND DEVICES AND SYSTEMS THEREFOR

CROSS-REFERENCE TO RELATED APPLICATIONS

This application is a continuation of U.S. patent application Ser. No. 17/062,440, filed on Oct. 2, 2020, which is a continuation of PCT Patent Application Number PCT/US20/27683, filed on Apr. 10, 2020, which claims priority to and the benefit of U.S. Provisional Patent Application No. 62/832,486, filed on Apr. 11, 2019, and U.S. Provisional Patent Application No. 62/960,861, filed on Jan. 14, 2020. The disclosures of all of the above noted patent applications are hereby incorporated herein, in their entireties, by reference.

FIELD OF INVENTION

Various embodiments of the present invention provide systems and methods for amelioration of fluid within the subarachnoid space and, more specifically, to methods and systems, whereby an ameliorating agent disposed, placed or located on a structure in fluidic communication with the subarachnoid space of a mammalian subject ameliorates a biomolecule contained within the subarachnoid space.

BACKGROUND

Many neurodegenerative diseases have been tied to the accumulation of biomolecules (e.g., toxic proteins) contained in cerebrospinal fluid (CSF) or other fluids (e.g., interstitial fluid) within the subarachnoid space (SAS) of a mammalian subject. Problematically, these (e.g., toxic) biomolecules may be secreted and transported by the CSF to other cells in the body, which process may occur over the span of years. For example, dipeptide repeat proteins (DPRs) and/or TDP-43 have been implicated in neuronal death in the pathology of amyotrophic lateral sclerosis (ALS, or Lou Gehrig's disease), Alzheimer disease (AD), frontotemporal degeneration (FTD), Parkinson's disease (PD), Huntington's disease (HD), and progressive supranuclear palsy (PSP), to name just a few. Hence, research has focused primarily on the removal of harmful DPRs. Techniques for removing DPRs and/or TDP-43 have included: shunting CSF from the CSF space, diluting the CSF (e.g., with an artificial fluid), administering a drug into the CSF, conditioning the CSF, and/or manipulating CSF flow. However, these conventional techniques often produce complications.

SUMMARY OF INVENTION

As a result, it is desirable to provide in situ and other systems and methods for amelioration of CSF and other fluids in the SAS (e.g., interstitial fluid) by partially or completely implanting the systems or components thereof in vivo (e.g., completely or predominantly within the SAS).

In a first aspect, some embodiments of the present invention relate to a method for treating a mammalian subject suffering from at least one of a pathology, trauma, a neurological disease, a non-neurological disease, or a deficiency characterized by the presence of toxic biomolecules in CSF. In some embodiments, the method includes amelioration of the toxic biomolecules (e.g., via enzymatically digesting the toxic biomolecules and/or by disposing pin1, an exosome, and/or a living cell in a cartridge and circulating the CSF through the cartridge) in the CSF using an ameliorating agent, an amelioration technique, or combinations thereof. In some variations, enzymatically digesting the toxic biomolecules may include using a protease to enzymatically digest the toxic biomolecules. Amelioration of the toxic biomolecules may occur at least partially in: a cerebral ventricular space of the subject, in a cerebral subarachnoid space of the subject, and/or in a lumbar region of the subject.

In some implementations, the method may include the steps of: selecting a patient having at least one symptom of a pathology, trauma, neurological disease (e.g., amyotrophic lateral sclerosis (ALS), Alzheimer disease (AD), frontotemporal degeneration (FTD), progressive supranuclear palsy (PSP), Huntington disease (HD), and Parkinson disease (PD), cancer, intracranial metastatic disease (IMD), diabetes, type-3 diabetes, lupus, poisoning, chronic traumatic encephalopathy (CTE), bacterial meningitis, aneurysms, stroke, cerebral vasospasms, and traumatic brain injury), non-neurological disease, or deficiency; removing a volume (e.g., between about 1 mL and about 200 mL at a flow rate between about 0.1 mL/min and about 100 mL/min) of CSF from a first location (e.g., a location in the lumbar CSF space); treating the volume of CSF with a cartridge to treat (e.g., removing, reducing, altering, sequestering, digesting, neutralizing, or deactivating) the symptom, such as a substance(s) (e.g., tau, cis p-tau, Abeta, TDP-43, SOD1, DPRs, neurofilaments, and alpha-synuclein), for example, by enzymatic activity; and returning the treated volume of CSF to the patient at a second location (e.g., a location in the cervical CSF space or the ventricular CSF space). In some applications, embodiments of the method also include waiting a first length of time after removing the volume of fluid from the patient and/or waiting a second length of time after returning the treated volume of fluid to the patient.

In some implementations, the method may also include measuring a characteristic of the treated volume of CSF using a sensor; and returning the treated volume of CSF to the patient at a second location in a cervical CSF space and/or a ventricular CSF space of the patient. In some variations, due to a bi-directional and/or dual flow feature of the method, in the alternative, a volume of CSF may be removed from a first location in the cervical CSF space and/or the ventricular CSF space of the patient location and the treated volume of CSF to the patient may be returned to a second location in the lumbar CSF space of the patient. Moreover, CSF may reversibly flow through the enzyme cartridge a single instance or multiple instances, to increase residence time in the cartridge and treatment efficacy and effectiveness. Preferably, the treated CSF is returned to the patient at a rate that is substantially the same as a rate at which the volume of CSF is removed. In some implementations, these steps may occur at least partially concurrently. Optionally, the method may include filtering treated CSF with a getter to capture unbound enzyme prior to returning the treated CSF to the patient.

In some variations, the method made also include updating one or more parameters of a set of treatment operational parameters based on a measured CSF characteristic meeting or exceeding a predetermined threshold. The operational parameters may be set to maintain a specific pressure and/or a specific volume.

In some implementations, the method may include repeating, until one or more criteria are satisfied, the removing, treating, and returning steps and/or updating a parameter(s) of a set of treatment operational parameters (e.g., parameters that maintain at least one of a specific pressure, a specific volume change, and a specific flow rate within a CSF space of the patient) based on a measured fluid characteristic meeting or exceeding a predetermined threshold.

In some variations, the volume of CSF removed is greater than or equal to the volume of the treated CSF returned. Preferably, the volume of CSF is returned to the patient at substantially the same rate at which the volume of CSF is removed from the patient.

In a second aspect, some embodiments of the present invention relate to a CSF ameliorating system for use in fluidic communication with (e.g., implanted (i.e., completely or partially) within) a mammalian subject. In one embodiment, the system includes a substrate (e.g., a cartridge) and an ameliorating agent. The ameliorating agent may be an enzyme disposed on and/or an enzyme decorated on an interior surface of the cartridge. Alternatively, the ameliorating agent may include pin1, an exosome, and/or a living cell disposed in the cartridge.

In one implementation, the ameliorating agent modifies or degrades the biomolecule present in the CSF by enzymatic digestion and, in some variations, the enzyme used for enzymatic digestion may be a protease (e.g., trypsin; elastase; cathepsin; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin E, S, B, K, L1; Tissue Type A; heparinase; granzymes, including granzyme A; meprin alpha; pepsin; endothiapepsin; kallikrein-6; kallikrein-5; and combinations thereof.

Exemplary embodiments of the substrate may include a substrate that is collapsible and/or flexible to facilitate catheter-based implantation within the subject; a substrate that includes a plurality of cilia (e.g., cilia projections that extend from an outer shell portion, fibers and/or brush fibers that are retractable and/or extendable from within the substrate); beads (e.g., superparamagnetic beads) disposed within or on the substrate (e.g., a container); a dialysis membrane catheter; a tubular device containing the biomolecular ameliorating agent; and/or a plurality of appendages.

In some applications, the system also includes a subcutaneous port(s) for sampling CSF; introducing, removing, or replenishing the ameliorating agent; introducing or removing the substrate; introducing a drug; and/or chronically maintaining a drug. In another application, the system may also include one or more CSF fluid loops having an access port(s) (e.g., a first access port and a second access port) to augment CSF flow across the substrate, as well as one or more of: a sensor(s) (e.g., temperature sensor, a pressure sensor, a pH sensor, a UV sensor, an IR sensor, a turbulence sensor, a Raman scattering sensor, dynamic light scattering sensor, a constituent concentration sensor, a flow sensor, and combinations thereof) located within the CSF loop; a pump (s) (e.g., a peristaltic pump, a rotary vane pump, an Archimedes screw, an air bladder, a pneumatic bladder, a hydraulic bladder, a displacement pump, an electromotive pump, a passive pump, an autopump, a valveless pump, a bi-directional pump, and combinations thereof); a valve(s) (e.g., a one-way valve, a bicuspid valve, a tricuspid valve, a ruby valve, and combinations thereof); and/or an actuator(s) located within the CSF loop. Preferably, a system controller (e.g., an open loop controller, a closed loop controller, a PID controller, a PID threshold controller, a system identification algorithm, and combinations thereof) may be operatively coupled to one or more of the sensor(s), the pump(s), and/or the actuator(s).

In some variations, the system may also include a stent and/or a pump (e.g. with a porous wall) and/or an actuator, such that the biomolecular ameliorating agent is decorated on an interior surface of the pump and, more specifically, the biomolecular ameliorating agent is retained by the porous wall.

In some applications, the system also includes one or more of: a control system; a CSF direction system; one or more of a cervical catheter, a lumber catheter, or a ventricular catheter; and sensors for measuring or sensing CSF components and/or CSF properties. The control system may maintain pressure and/or flow of CSF within the mammalian subject. In some variations, the control system has a programmable memory, a data handling system, and a communications subsystem, while the CSF direction system has a pump; tubing; T-valves, anti-backflow valves, and/or shutoff valves; and access ports and/or subcutaneous access ports.

In some embodiments, treating the volume of CSF may include filtering the volume of CSF using at least one of: size filtration, ionic filtration, tangential flow filtration, countercurrent tangential flow filtration, ultrafiltration, notch filtration, series filtration, or cascade filtration. In other embodiments, treating the volume of CSF may include: removing waste, subjecting the volume of CSF to enzymatic digestion, subjecting the volume of CSF to bioaffinity interactions with or without use of an antibody, subjecting the volume of CSF to ultraviolet radiation, subjecting the volume of CSF to heat or cold or a temperature change, introducing the volume of CSF to an electromagnetic field(s), subjecting the volume of CSF to a pressure change, subjecting the volume of CSF to a pH change, and/or subjecting the volume of CSF to a manipulation agent(s) (e.g., magnetic beads, nanoparticles, optical tweezers, and combinations thereof) alone or in combination with a bioaffinity agent(s).

In some applications, the method may also include: maintaining a reduced toxic biomolecule content in the CSF after an initial toxic biomolecule content in the CSF is diminished; charge or size-filtering the CSF to filter out the toxic biomolecules; antibody or nanobody treatment of the CSF to filter out the toxic biomolecules; a combination of enzymatic and charge or size filtering methods to filter out the toxic biomolecules; and/or augmenting naturally occurring (e.g., focused) flow of the CSF.

In some implementations, the ameliorating agent may be introduced into the CSF within a subarachnoid space in a subject. In other implementations, the ameliorating agent may be disposed on a solid, a collapsible, or a flexible structure, which may be implanted in the subject (e.g., by catheter-based implantation). In some variations, the structure includes one or more of: a substrate, a cilium, cilia extending from a substrate, a fiber, fibers extending from a substrate, an appendage, appendages extending from a substrate, a fenestration, a bead, a plurality of beads, a bistable monolithic structure, an outcropping appendage, a stent, a catheter, a cartridge, a slurry, and combinations thereof.

In some embodiments, the structure includes cilia on a surface (e.g., a hydraulically-activatable surface, a pneumatically-activatable surface, and/or a shape memory surface) that, in some variations, may include an outer shell surrounding an inner core. With such a composition, the method may further include: inflating the outer shell on which the cilia are formed; inflating the inner core, such that CSF located between the inner core and the outer shell is forced past the cilia; and deflating the inner core and the outer shell.

In other embodiments, the structure may include fibers. With such a composition, the method may include extending the fibers from within a delivery device into the CSF and retracting the fibers back into the delivery device.

In yet another embodiment, the structure may include a monolithic bistable structure with appendages formed thereon. With such a composition, the method may include expanding the monolithic bistable structure to deploy the appendages into the CSF and to outcrop from the monolithic bistable structure and deflating the monolithic bistable structure to retract the appendages and to provide a mixing motion in the CSF.

In some embodiments of the method, the amelioration technique includes introducing an ameliorating agent outside a subarachnoid space in the subject and permitting circulation of CSF (e.g., using an active or passive pump) past the ameliorating agent. In some implementations, the embodiment includes returning treated CSF to the subarachnoid space. In some applications, circulating CSF and returning treated CSF may include transporting CSF (e.g., using catheters) via a plurality of catheter insertion locations accessing the subarachnoid space; transporting CSF (e.g., using a multi-lumen catheter arrangement) via a single catheter insertion location accessing the subarachnoid space; and/or active circulation (e.g., by active or passive pumping) to maintain a controlled fluid flow. In some implementations, circulating CSF includes disposing the ameliorating agent into a catheter or a cartridge and flowing CSF through the catheter or cartridge.

In a third aspect, some embodiments of the present invention relate to a CSF ameliorating system implantable (e.g., completely or partially) within, so as to be in fluidic communication with, a mammalian subject. In some embodiments, the system is operable to provide a focused flow of the CSF and is configured to include: flow controllers, catheters, pumps, and/or structures to modify fluid flow. Optionally, the system may also include catheters located at distinct fluid access points to the subarachnoid space (e.g., in the lateral ventricle and the lumbar sac, in the cisterna *magna* and the lumbar sac, in the cisterna *magna* and the frontal lobe, in the lateral temporal subarachnoid spaces, and/or in the cervical subarachnoid space and the lumbar sac). In some implementations, one or more passive pumps, internal active pumps, and/or passive flow modifiers may be implanted substantially within the subarachnoid space.

In a fourth aspect, some embodiments of the present invention relate to a CSF ameliorating system implantable (e.g., completely or partially) within, so as to be in fluidic communication with, a mammalian subject. In some embodiments, the system is configured to provide a focused flow of the CSF and includes a substrate; an ameliorating agent disposed on and/or within the substrate; and one or more of flow controllers, catheters, pumps, and/or structures to modify fluid flow.

In a fifth aspect, some embodiments of the invention relate to a method for treating a mammalian subject suffering from at least one of a pathology, trauma, a neurological disease, a non-neurological disease, or a deficiency characterized by the presence of toxic biomolecules in CSF. In some embodiments, the method includes amelioration of the toxic biomolecules (e.g., via enzymatically digesting the toxic biomolecules and/or by disposing pin1, an exosome, and/or a living cell in a cartridge and circulating the CSF through the cartridge) in the CSF using an ameliorating agent, an amelioration technique, or combinations thereof. In some variations, enzymatically digesting the toxic biomolecules may include using a protease to enzymatically digest the toxic biomolecules. Amelioration of the toxic biomolecules may occur at least partially in: a cerebral ventricular space of the subject, in a cerebral subarachnoid space of the subject, and/or in a lumbar region of the subject. In some applications, the method may include reversibly flowing the CSF through the enzyme cartridge In yet another embodiment of the method, the amelioration technique includes circulating CSF in a flow (e.g., using an auto-bladder pump to actively transport the CSF) from a first location in a subarachnoid space to a second location in the subarachnoid space. In some variations, the flow remains substantially within the subarachnoid space. In some applications, the method also includes enabling the CSF to circulate outside of the subarachnoid space or circulating CSF at a natural flow rate. Circulation may be from a first location having a low concentration of biomolecule to a location having a high concentration of biomolecule or from a first location having a high concentration of biomolecule to a location having a low concentration of biomolecule.

In another embodiment, the method includes augmenting (e.g. a phase, a direction, and/or an amplitude of a CSF flow) the naturally occurring (e.g. focused) flow of the CSF. In some applications, the method may also include circulating ameliorating agent through the CSF in the subject.

In yet another embodiment, the method may include circulated ameliorating agent through the CSF in the subject. In various applications, ameliorating agent may be circulated through the CSF flowing at natural flow levels, ameliorating agent may be circulated through the CSF outside of a subarachnoid space in the subject, and/or ameliorating agent may be circulated through the CSF substantially within the subarachnoid space in the subject. In some variations, circulating the ameliorating agent through the CSF within the subarachnoid space may include applying the ameliorating agent to a plurality of beads, introducing the beads into the CSF within the subarachnoid space (e.g., by containing the beads within a dialysis membrane catheter or a porous bag, by introducing the beads in a slurry, by containing the beads in a tubular device, and/or by containing the beads in a multi-lumen catheter), and imparting movement to the beads. Optionally, beads may be added or removed using a syringe.

In some applications, when using a multi-lumen catheter, the method may include introducing the beads from a supply reservoir into a first lumen of the multi-lumen catheter, circulating the beads through the first lumen and through a second lumen of the multi-lumen catheter, and introducing the beads from the second lumen into a receiving reservoir. Moreover, circulating the ameliorating agent through CSF outside of the subarachnoid space may include applying the ameliorating agent to a plurality of beads, introducing the beads into the CSF outside of the subarachnoid space, and circulating the beads. In some variations, the first and second lumens of the multi-lumen catheter include pores sized such that CSF biomolecules may pass through the pores while preventing the beads from passing through the pores. In other variations, the multi-lumen catheter is operable to permit countercurrent flow.

In a sixth aspect, some embodiments of the present invention relate to a method of treating a mammalian subject suffering from neurological or non-neurological pathologies, neurological or non-neurological trauma, or neurological or non-neurological deficiencies. In some embodiments, the method includes circulating CSF in a focused flow in a subject. In some applications, amelioration of the toxic biomolecules in the CSF using an ameliorating agent, an amelioration technique, or combinations thereof. In other implementations, no ameliorating agent is utilized. In some implementations, circulating CSF in a focused flow includes: circulating CSF at natural flow levels, enabling CSF flow outside of the subarachnoid space, limiting CSF flow only within the subarachnoid space, and/or using a passive pump.

In a seventh aspect, some embodiments of invention relate to a kit for use in amelioration of a fluid drawn from a mammalian subject. In some embodiments, the kit includes a ventricle line portion that is removably attachable to a first location on the subject, a lumbar line portion that is removably attachable to a second location on the subject, a circulation system in fluidic communication between the ventricle line portion and the lumbar line portion, monitoring hardware including a cartridge in operational communication with the circulation system, wherein the cartridge contains an ameliorating agent for amelioration of the fluid, and a pumping device for drawing the fluid, circulating the fluid, and returning the fluid to the subject. In some implementations, the ventricle line portion may include a ventricular catheter, a catheter adapter(s) removably attachable to the ventricular catheter, a subcutaneous access port, and a subcutaneous access needle. In some implementations, the lumbar line portion may include a lumbar catheter, a catheter adapter(s) removably attachable to the lumbar catheter, a subcutaneous access port, and a subcutaneous access needle. Optionally, the ventricle line portion and/or the lumbar line portion may include a peritoneal catheter.

BRIEF DESCRIPTION OF DRAWINGS

Various features and advantages of the various embodiments and implementations of aspects of the present invention, as well as the invention itself, can be more fully understood from the following description of the various presented embodiments, when read together with the accompanying schematic drawings, in which:

FIG. 1A shows a schematic of a passive substrate having a plurality of cilia decorated with an ameliorating agent after an outer shell is inflated, in accordance with some embodiment of the present invention;

FIG. 1B shows a schematic of the passive substrate of FIG. 1A after an inner core is inflated, in accordance with some embodiments of the present invention;

FIG. 1C shows a schematic of the passive substrate of FIG. 1B after the inner core and outer shell are deflated, in accordance with some embodiments of the present invention;

FIG. 2A shows a schematic of an at-rest (deflated) state of a monolithic bistable structure having a plurality of ameliorating agent-coated cilia formed on a plurality of appendages, in accordance with some embodiments of the present invention;

FIG. 2B shows a schematic of an inset view of a gap between a pair of appendages from FIG. 2A, in accordance with some embodiments of the present invention;

FIG. 2C shows a schematic of an expanded state of the monolithic bistable structure of FIG. 2A, in accordance with some embodiments of the present invention;

FIG. 6 shows a schematic of a system that combines an enzymatic filter and size filters, in accordance with some embodiments of the present invention;

FIG. 8A shows a schematic of a first stage of a passive pump for driving fluid through the pump using normal pressure fluctuations in the SAS fluid, in accordance with some embodiments of the present invention;

FIG. 8B shows a schematic of a second stage of the passive pump of FIG. 8A for driving fluid through the pump using normal pressure fluctuations in the SAS fluid, in accordance with some embodiments of the present invention;

FIG. 8C shows a schematic of a third stage of the passive pump of FIG. 8A for driving fluid through the pump using normal pressure fluctuations in the SAS fluid, in accordance with some embodiments of the present invention;

FIG. 10A shows a schematic of a first ameliorating system having a bulk flow system, in accordance with some embodiments of the present invention;

FIG. 10B shows a schematic of a second ameliorating system having a bulk flow system implanted substantially within the SAS, in accordance with some embodiments of the present invention;

DETAILED DESCRIPTION

Figure 3:
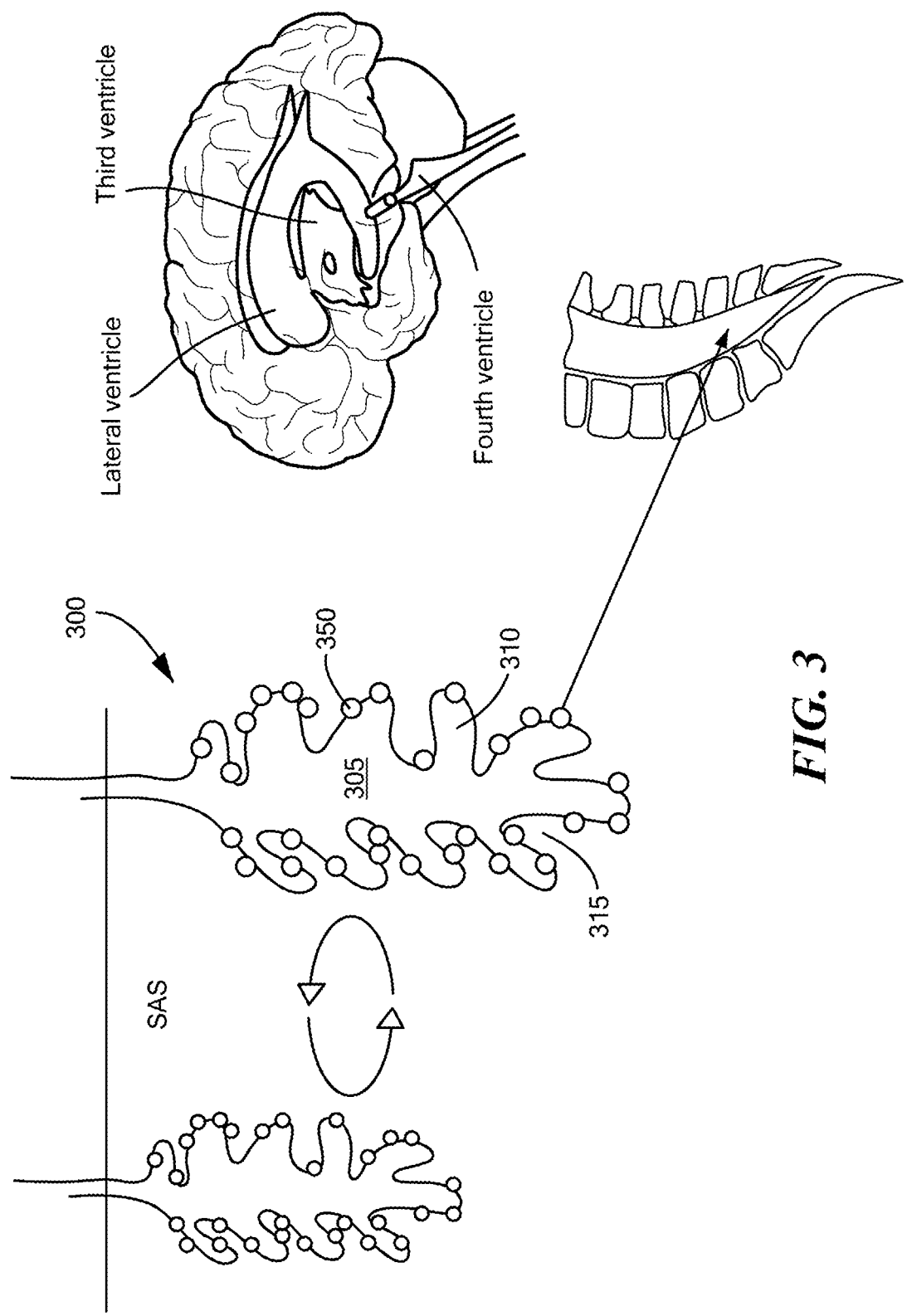
FIG. 3 shows a schematic of a fenestrated flexible structure decorated with an ameliorating agent, in accordance with some embodiments of the present invention.

Although embodiments of the invention will be described primarily in terms of treating neurological diseases in a fluid and, more specifically, in terms of amelioration of cerebrospinal fluid (CSF) from a mammalian subject, the system, methods, and techniques described herein are equally applicable to non-neurological diseases and disorders, as well as applications and conditions (e.g., cancer, intracranial metastatic disease (IMD), diabetes, type-3 diabetes, lupus, poisoning, chronic traumatic encephalopathy (CTE), bacterial meningitis, aneurysms, stroke, cerebral vasospasms, traumatic brain injury, rheumatoid arthritis, drug overdose, certain traumas, etc.). Furthermore, embodiments of the invention also apply to conditions and applications in living cells. For example, certain embodiments and applications or implementations of the invention can provide an access point to deliver living cells or exosomes to the fluid (e.g., CSF) and nervous system. More specifically, living cells or other organisms (e.g., yeast, bacteria, viruses, and so forth) may be placed in an external (ex corpore) cartridge providing secretory products that may benefit the health of, for example, the central nervous system. CSF may be passed through the cartridge containing the living cells.

Definitions

As used in this description and the accompanying claims, the following terms shall have the meanings indicated, unless the context otherwise requires or makes clear a different meaning:

Biomolecule refers to any molecule that may be produced by a living system (i.e., an organism) or that is similar to such. For the purpose of illustration rather that limitation, a biomolecule may include RNA, DNA, proteins, peptides, lipids, carbohydrates, polysaccharides, nucleic acids, oligonucleotides, antisense oligonucleotides, polynucleotides, amino acids, enzymes, antibodies, nanobodies, molecular imprinted polymers, primary metabolites, secondary metabolites, and natural products;

Fluid refers to any flowable biological medium, such as flowable medium resident in the subarachnoid space or elsewhere in a subject, and including cerebrospinal fluid (CSF), interstitial fluid (ISF), blood, sweat, tears, semen, glymph, urine, breast milk, and the like;

Cerebrospinal fluid space refers to volume interior to the blood brain barrier, including the subarachnoid space;

Subject or patient refers to a mammal (e.g., man or animal) undergoing medical therapy, diagnosis, monitoring, research, or care;

Ex corpore refers to occurring outside of a mammalian body and may be used interchangeably herein with the terms extracorporeal and ex-vivo; and In situ refers to occurring within a mammalian body and may be used interchangeably with the term in-vivo.

Amelioration

Embodiments of the present invention provide systems and methods for amelioration of a fluid in the subarachnoid space (SAS) (e.g., a cerebrospinal fluid (CSF), an interstitial fluid (ISF), blood, and the like) of a mammalian subject, generally referred to herein as CSF, unless otherwise particularly distinguished (e.g., referred to as solely CSF). Representative systems may be completely or partially implanted within the body of the mammalian subject. Within the body, the systems and/or components thereof may also be completely or partially implanted within the SAS. The methods may include steps that may occur entirely in-vivo or that may include some steps that occur extracorporeally.

Amelioration, for the purpose of illustration rather than limitation, may include changing the physical parameters of the fluid, as well as digestion, removal, immobilization, reduction, and/or alteration to become more acceptable and/or inactivation of certain entities, including: target molecules, proteins, agglomerations, viruses, bacteria, cells, couples, enzymes, antibodies, substances, and/or any combination thereof. For example, in some embodiments and applications of the present invention, amelioration may refer to removing toxic proteins from or conditioning one or more of the blood, interstitial fluid, or glymph contained therein, or other fluid, as well as the impact that this removal has on treating diseases or conditions that affect various bodily functions, (i.e., improving the clinical condition of the patient). Moreover, amelioration may be performed by any one of: digestion, enzymatic digestion, filtration, size filtration, tangential flow filtering, countercurrent cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photo-acoustical interactions, chemical treatments, thermal methods, and combinations thereof. Advantageously, various embodiments or implementations of the present invention may reduce levels of toxicity and, once reduced, facilitate maintaining the reduced levels over time.

The extent of amelioration, as reflected by the concentration of the target biomolecules, may be detected through a variety of means. These include optical techniques (e.g., Raman, coherent Stokes, and anti-Stokes Raman spectroscopy; surface enhanced Raman spectroscopy; diamond nitrogen vacancy magnetometry; fluorescence correlation spectroscopy; dynamic light scattering; and the like) and use of nanostructures such as carbon nanotubes, enzyme linked immunosorbent assays, surface plasmon resonance, liquid chromatography mass spectrometry, circular proximity ligation assays, and the like.

Amelioration may include the use of a treatment system (e.g., UV radiation, IR radiation), as well as a substance, whose properties make it suitable for amelioration.

Amelioration of CSF or ameliorated CSF—which terms may be used interchangeably herein—refers to a treated volume of CSF in which one or more target compounds have been partially, mostly, or entirely removed. It will be appreciated that the term removed, as used herein, can refer not only to spatially separating, as in taking away, but also effectively removing by sequestering, immobilizing, or transforming the molecule (e.g., by shape change, denaturing, digestion, isomerization, or post-translational modification) to make it less toxic, non-toxic or irrelevant.

Ameliorating agent refers to any material or process capable of amelioration of a fluid, including enzymes, antibodies, or antibody fragments, nucleic acids, receptors, anti-bacterial, anti-viral, anti-DNA/RNA, protein/amino acid, carbohydrate, enzymes, isomerases, compounds with high-low biospecific binding affinity, aptamers, exosomes, ultraviolet light, temperature change, electric field, molecular imprinted polymers, living cells, and the like.

Amelioration Via Enzymatic Digestion

Amelioration of biomolecules within the CSF may also be by enzymatic digestion, such that, in some embodiments and applications, the ameliorating agent modifies or degrades the biomolecule in the CSF. To that end, an enzyme-substrate pair may be selected by means of a panel and counter panel search. For example, the panel of candidate enzymes to digest the biomolecules may be graded for stability, commercial availability, and relevant mechanism of interaction, while the counter panel may ensure that candidate enzymes would not affect substances in the CSF that the enzyme should not alter. Alternatively, the enzyme may be discovered through a microbial screen, such as a mutant hunt or a nitrogen vitality assay. In yet another embodiment, the enzyme may be selected through a biomolecular engineering computational model.

Methods of amelioration and the amelioration chemistry are described in International Patent Application Numbers PCT/US2019/042880 and PCT/US2019/042879, both entitled "Methods of Treating Neurological Disorders" and filed on Jul. 22, 2019, the disclosures of which are hereby incorporated herein by reference in their entireties.

In some embodiments, the agent for use in the ameliorating system may include: trypsin; elastase; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin, including the cathepsins E, S, B, K, or L1; Tissue Type A; heparinase; granzymes, including granzyme A; meprin alpha; pepsin; endothiapepsin; kallikrein-6; kallikrein-5; and combinations thereof. In other embodiments, pin1, exosomes, and/or living cells may be used as ameliorating agents.

Modification of Toxic Proteins

Various applications of the invention provide for methods of treating a neurological disorder or related condition characterized by the presence of a toxic protein in CSF, the method including: contacting the CSF of a subject in need thereof in situ or otherwise with an effective amount of a post-translational modifying protein capable of modifying the toxic protein, such that the concentration of the toxic protein is reduced.

In some embodiments, the substrate, target molecule, or substance may include: TDP43 (e.g., a misfolded TDP-43 protein, e.g., a mutant TDP-43 protein), of beta-amyloid (any species or form) or tau (or any number of hyper phosphorylated tau isoforms (e.g., tau protein aggregates, tau protein tangles, tau oligomers, hyperphosphorylated tau proteins, soluble tau proteins, tau dimers, cis pTau)) proteins, of reactive oxidative species, inflammatory mediators (e.g., cytokines, including TNF-a, IL-1, IL-2, IL-6, IL-12, interferon-y, etc.), alpha-synuclein proteins (including peptides or oligomers), insoluble superoxide dismutase-1 (SODI) (e.g., mutant or misfolded wild-type SOD1 protein), glutamate, neurofilament protein, and anti-GMI ganglioside antibodies, anti-AGM1-gangliosides antibodies, and sulfatides, blood cells (e.g., erythrocytes), oxyhemoglobin, endothelin, inflammatory mediators, bacterial or viral entity, tumor necrosis factor-alpha (TNFa) and IgG, cells and inflammatory mediators including but not limited to C5a, TNF a, I L 2, IL-6, interferon-γ, IgG, and endotoxins, T cells, B cells, anti-myelin antibodies and inflammatory mediators including but not limited to TNF a, IL 2, IL-6, interferon-γ, endothelin and enolase, DPRs, circulating tumor cells. In certain embodiments, the toxic protein is a mutant FUS/TLS protein. In certain embodiments, the toxic protein is in a toxic form.

The microtubule associated protein tau is a major component of the neurofibrillary tangles (NFTs) associated with AD and tauopathies that are characterized by hyperphosphorylation and aggregation of tau. Tau is an intrinsically unstructured protein due to its very low hydrophobic content containing a projection domain, a basic proline-rich region, and an assembly domain. Tau is known to carry various post-translational modifications, such as acetylation, deamidation, glycation, glycosylation, isomerization, methylation, nitration, phosphorylation, proteolysis, sumoylation and ubiquitylation. Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of two N-terminal insert regions and of the second, third and tenth exons of tau results in six tau isoforms of varying length in the CNS. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, whereas only 3R tau is expressed at the fetal stage. In tauopathies, mutations altering the splicing of tau transcript and the ratio of 3R to 4R tau isoforms are sufficient to cause neurodegenerative disease. In addition to the isoforms of full-length tau proteins, certain tau fragments (e.g., fragments resulting from endogenous protease cleavage) may also exhibit propensity to polymerize or aggregate, ability to facilitate polymerization or aggregation of another tau isoform or fragment, and/or ability to propagate tau polymerization or aggregation to other cells, thereby resulting in neurotoxicity. Such tau fragments include but are not limited to fragments 14-441, 26-230, 1-314, 26-44, 1-44, 1-156, 45-230, 243-441, 256-441, 256-368, 1-368, 1-421, 151-421, 1-391, and X-441 wherein X is any integer from 182 to 194 (amino acid positions numbered according to the sequence of the 2N4R isoform). In addition to these tau fragments, certain other fragments, such as fragments 124-441 and 1-402 (amino acid positions numbered according to the sequence of the 2N4R isoform), may be useful as biomarkers for diagnosing neurological disorders or monitoring patients' progression or response to treatment. Post-translational modifications of tau, such as phosphorylation and isomerization (cis or trans isomeric form), also greatly affect the ability of tau to aggregate. For example, hyperphosphorylation of tau at serine and threonine residues preceding proline (pSer/Thr-Pro) results in insolubility and leads to neurofibrillary tangles (NFTs). Phosphorylation of tau specifically at Thr231-Pro enables binding of the prolyl isomerase Pin1, which catalyzes conversion between the cis and trans forms. Phosphatases, such as PP2A, catalyze dephosphorylation of tau only in the trans form. In view of the above, tau in human brain tissue can exist in a variety of different lengths and morphologies and with multiple post-translational modifications. As used herein, the term "tau" includes various isoforms and fragments of tau protein with one or more post-translational modifications, and in any folding status. As tau progresses from normal to NFT it passes through a 'soluble' state in which the protein may be hyperphosphorylated, mislocalized, conformationally changed and/or oligomeric but not yet fibrillar.

Post-Translational Modifying Proteins

In some implementations, embodiments of the invention provide methods of treating a neurological disorder or related condition characterized by the presence of a toxic protein in CSF, the method including: contacting the CSF of a subject in need thereof with an effective amount of a post-translational modifying protein capable of modifying the toxic protein such that the concentration of the toxic protein is reduced.

In some variations, the embodiment also provides for compositions that include CSF of a subject having a neurological disorder or related condition characterized by the presence of a toxic protein in a toxic or pre-toxic form in CSF and a post-translational modifying protein capable of modifying the toxic protein such that the concentration of the toxic protein is reduced.

The selective alteration of a toxic protein in a toxic or pre-toxic form by the post-translational modifying protein of embodiments of the present invention is accomplished by a combination of substrate selectivity (post-translational modifying proteins that preferentially recognize the toxic protein in the toxic or pre-toxic form of the protein), active-site specificity (post-translational modifying proteins that have specificity for cleaving the peptide bonds of the residue motifs encountered in the toxic protein in the toxic or pre-toxic form), substrate affinity (based on binding kinetics) and enzyme efficiency (rate of enzyme reaction). In certain embodiments of the invention, the post-translational modifying protein is a mammalian, microbial (e.g., fungal, bacterial, or viral), or plant protein.

In other aspects and embodiments of the invention, the post-translational modifying protein may be a phosphatase, an isomerase, a ubiquitin-activating enzyme (E1), a ubiquitin-conjugating enzyme (E2), a ubiquitin ligase (E3), a kinase, an acetylase, a deacetylase, a glycosylase, or a deglycosylase.

Phosphatases

A phosphatase is an enzyme that removes a phosphate group from a phosphorylated amino acid residue of a substrate protein. In certain variations of the embodiments of this invention, the post-translational modifying protein is a phosphatase selected from the list comprising: PP1, PP2A, PP2B, PP4, PP5, PP6, PP7, PP2C, VHR, DUSP1, DUSP2, DUSP3, DU5P4, DUSP5, DUSP6, DUSP7, DUSP8, DUSP9, DUSP10, DUSP11, DUSP12, DUSP13, DUSP14, DUSP15, DUSP16, DUSP17, DUSP18, DUSP19, DUSP20, DUSP21, DUSP22, DUSP23, DUSP24, DUSP25, DUSP26, DUSP27, DUSP28, PHP, PPP1CA, PPP1CB, PPP1CC, PPP2CA, PPP2CB, PPP3CA, PPP3CB, PPP3CC, PPP4C, PPP5C, PPP6C, CDC14A, CDC14B, CDC14C, CDKN3, PTEN, SSH1, SSH2, SSH3, CTDP1, CTDSP1, CTDSP2, CTDSPL, DULLARD, EPM2A, ILKAP, MDSP, PGAM5, PHLPP1, PHLPP2, PPEF1, PPEF2, PPM1A, PPM1B, PPM1D, PPM1E, PPM1F, PPM1G, PPM1H, PPM1J, PPM1K, PPM1L, PPM1M, PPM1N, PPTC7, PTPMT1, SSU72, and UBLCP1.

Isomerases

Isomerases are enzymes that catalyze the conversion of a molecule from one isomeric structure to another. Intramolecular bonds are broken and formed during isomerization, resulting in a molecule with identical molecular formula but different bond connectivity or spatial arrangement. In certain implementation of the various embodiments, the post-translational modifying protein is an isomerase selected from the list comprising: FK506-binding protein 4 (FKBP52), FK506-binding protein 51 (FKBP51, also known as FKBP5), FK506-binding protein (FKBP12), peptidylprolyl cis/trans isomerase NIMA-interacting 1 (Pin1), alanine racemase, methionine racemase, lactate racemase, tartrate epimerase, ribulose-phosphate 3-epimerase, UDP-glucose 4-epimerase, methylmalonyl CoA epimerase, hydantoin racemase, Maleate isomerase, Maleylacetoacetate isomerase, Maleylpyruvate isomerase, Linoleate isomerase, Furylfuramide isomerase, Peptidylprolyl isomerase, Farnesol 2-isomerase, 2-chloro-4-carboxymethylenebut-2-en-1,4-olide isomerase, Zeta-carotene isomerase, Prolycopene isomerase, Beta-carotene isomerase, Triose-phosphate isomerase, Ribose-5-phosphate isomerase, Phenylpyruvate tautomerase, Oxaloacetate tautomerase, Steroid Delta-isomerase, L-dopachrome isomerase, Protein disulfide-isomerase, Prostaglandin-D synthase, Allene-oxide cyclase, Lysolecithin acylmutase, Precorrin-8X methylmutase, Phosphoglucomutase, Phosphopentomutase, Beta-lysine 5,6-aminomutase, Tyrosine 2,3-aminomutase, (hydroxyamino) benzene mutase, Isochorismate synthase, Methylaspartate mutase, Chorismate mutase, Muconate cycloisomerase, 3-carboxy-cis,cis-muconate cycloisomerase, Tetrahydroxypteridine cycloisomerase, Inositol-3-phosphate synthase, Carboxy-cis,cis-muconate cyclase, Chalcone isomerase, Chloromuconate cycloisomerase, (+)-bornyl diphosphate synthase, Cycloeucalenol cycloisomerase, Alpha-pinene-oxide decyclase, Dichloromuconate cycloisomerase, Copalyl diphosphate synthase, Ent-copalyl diphosphate synthase, Syn-copalyl-diphosphate synthase, Terpentedienyl-diphosphate synthase, Halimadienyl-diphosphate synthase, (S)-beta-macrocarpene synthase, Lycopene epsilon-cyclase, Lycopene beta-cyclase, Prosolanapyrone-III cycloisomerase, and D-ribose pyranase. In certain embodiments, the isomerase is Pin1.

Ubiqutinating Enzymes

Ubiquitination is a post-translational modification, wherein the small regulatory protein ubiquitin is bound to a target lysine residue of a protein substrate. Ubiquitination includes multiple steps, activation (performed by ubiquitin-activating enzyme E1), conjugation (performed by a ubiquitin-conjugating enzyme E2), and ligation (performed by a ubiquitin ligase E3).

In certain applications of the various embodiments, the post-translational modifying protein is a ubiquitinating enzyme selected from the list consisting of: an E1 ubiquitin-activating enzyme, e.g., UBA1, UBA2, UBA3, UBA5, UBA6, UBA7, ATG7, NAE1, SAE1; an E2 ubiquitin-conjugating enzyme, e.g., UBE2A, UBE2B, UBE2C, UBE2D1, UBE2D2, UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2O, UBE2Q1, UBE2Q2, UBE2R1 (CDC134), UBE2R2, UBE2S, UBE2T, UBE2U, UBE2V1, UBE2V2, UBE2W, UBE2Z, ATG3, BIRC6, UFC1; and an E3 ubiquitin-ligase, e.g., AFF4, AMFR, ANAPC11, ANKIB1, AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, ITCH, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, MDM2, MDM4, MECOM, MEX3A, MEX3B, MEX3C, MEX3D, MGRN1, M1B1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1 B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, NF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1, SYVN1, TMEM129, TOPORS, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, CIAR, ZBTB12, ZFP91, ZFPL1, ZNF280A, ZNF341, ZNF511, ZNF521, ZNF598, ZNF645, ZNRF1, ZNRF2, ZNRF3, ZNRF4, ZSWIM2, ZXDC.

Ameliorating Agent Introduced without Circulation of Agent

CSF may be (e.g., chronically, intermittently, or the like) treated in several ways in accordance with various embodiments of systems and methods of the invention. For example, CSF may be presented with a high flow rate past a stationary or substantially stationary ameliorating agent that is completely implanted within the mammalian subject, but outside of the SAS. For example, the untreated CSF may leave the SAS, may be ameliorated by the agent outside of the SAS, and may then be returned to the SAS. Typically, for the purpose of transporting the CSF outside of the SAS and/or the body and returning it to the SAS, such an approach may require use of multiple catheters (and multiple insertion locations) and/or use of a multi-lumen catheter (and optionally only a single insertion location). CSF flow may occur naturally, by active pumping, or by passive pumping. The advantages of such an approach include: it is less invasive to the SAS, access to the structure associated with the stationary ameliorating agent is facilitated, and it provides a greater space for the stationary ameliorating agent and any pump elements. This approach involves active circulation of the CSF and CSF fluid flow that requires careful control.

In an alternative approach, an ameliorating agent may be located within the SAS on a structure (e.g., a substrate, such as a solid substrate that is immobilized locally) that may be collapsible or flexible and untreated CSF may be circulated past the ameliorating agent. In some applications, it may be desirable that the ameliorating agent remains stationary or substantially stationary. In other applications, the ameliorating agent may be intentionally actuated. The term substantially stationary implies that the ameliorating agent is not actively moved, however, fluctuations of movement of or in the structure may be caused by the physiological CSF motion.

Typically, CSF flow may occur naturally; however, in some applications, it may be desirable to actively pump or passively pump the CSF to enhance the ameliorating activity and efficiency. Depending on the circulation method implemented and/or the system or device used, CSF flow may remain entirely within the SAS. In some implementations, however, CSF may be transported outside of the SAS, from one portion of the SAS and returned to another portion of the SAS, which may require one or two or more catheter insertion locations.

In various implementations, to reduce the likelihood of infection, the structure associated with the ameliorating agent and/or system components (e.g., subcutaneous ports and reservoirs, active or passive pumps, and so forth) may be implanted under the epidermis, within or outside of the SAS. Subcutaneous ports and reservoirs may be provided in the systems to facilitate: sampling CSF; introducing or removing a (e.g., solid) substrate; introducing, removing, or replenishing/refreshing the ameliorating agent; and/or administering drugs (e.g., introducing and chronically maintaining) into the CSF (e.g., by a bolus or continuously).

In the absence of an active circulation of the agent, an in situ ameliorating element may also reduce the target biomolecule (e.g., DPR) concentration in the CSF space. Assuming bulk flow is slow (e.g., about 0.5 mL/min), the amelioration effect is dominated by pulsatile flow, which may be due to respiratory or cardiac cycles. Assuming that the enzyme device has an active cross-section in the back-and-forth (i.e., pulsatile) flow that is 10% of the flow cross-sectional area and assuming one collision or interaction between a biomolecule and the enzyme device will ameliorate the biomolecule, then the probability that the molecule will be ameliorated (i.e., converted) in n passes is:

$$P(n) = 1 - (1 - 0.1)^n.$$

Accordingly, for $P(n) > 95\%$, $n > \ln(0.05)/\ln(0.9) = 28$, or exposure time $(t) > n \times 3 \text{ sec} = 85 \text{ sec}$.

A method of localized fluid flow across elements (e.g., cilia) that have been decorated with an ameliorating agent is shown schematically in FIGS. 1A through 1C. In some embodiments, the (e.g., flexible or collapsible, solid) structure or substrate 100 having an ameliorating agent decorated thereon may be introduced into the SAS, without requiring circulating an ameliorating agent. In some applications, the structure or substrate 100 may be implanted into the SAS via a catheter. The CSF may be selectively circulated (e.g., naturally, by actively pumping the CSF, and/or by passively pumping the CSF) past the stationary or substantially stationary ameliorating agent. Hence, CSF flow may be at or beyond natural CSF flow rates. Active and passive pumping, as well as the natural circulation, may take place wholly within the SAS or the CSF may be routed in and out of the SAS. The source and power for the hydraulic or pneumatic actuation may be located outside of the SAS. The surfaces and structures may be made of any suitable compliant and resilient biocompatible material, including polymer, elastomer, thermoplastic elastomer (TPE), etc. Although various embodiments are described in conjunction with hydraulically- or pneumatically-actuated surfaces, the structure may, alternatively or additionally, include a shape memory surface.

In some implementations, the structure or substrate 100 may include an inner core 10a (FIGS. 1A and 1C), 10b (FIG. 1B) and an outer shell 20a (FIG. 1C), 20b (FIGS. 1A and 1B), each of which has a deflated or contracted state (a) and an inflated or expanded state (b). A plurality of (e.g., hair-like or fiber-like) cilia 25 may be integral with or fixedly attached to (e.g., an outer, peripheral surface of) the outer shell 20a, 20b. Advantageously, in operation, varying amounts of an ameliorating agent 30 may be decorated on or attached to each of the cilia 25 and/or the core and the shell. The outer shell 20a, 20b may also include an inlet/outlet port 35, as well as a plurality of openings 40. The inlet/outlet port 35 is in fluid communication with a source (e.g., hydraulic, pneumatic, and so forth) that is capable of selectively expanding and contracting the outer shell 20a, 20b, respectively, by introducing a fluid into and removing a fluid from the inside of the outer shell 20a, 20b. The plurality of openings 40 are structured and arranged to provide fluid communication between the inner and outer peripheral surfaces of the outer shell 20a, 20b.

The inner core 10a, 10b may also include an inlet/outlet port 45 that also is in fluid communication with a source (e.g., hydraulic, pneumatic, and so forth) that is capable of selectively expanding and contracting the inner core 10a, 10b, respectively, by introducing fluid into and removing a fluid from the inside of the inner core 10a, 10b.

In a first step of operation, from an at-rest state in which both the inner core 10a and the outer shell 20a are contracted or deflated (FIG. 1C), an inflating fluid may be introduced (e.g., via the inlet/outlet port 35) into the contracted or deflated outer shell 20a, causing it the inflate or expand and creating a void space 15 between the contracted or deflated inner core 10a and the expanded outer shell 20b (FIG. 1A). The void space 15 contains initially- or partially-treated CSF. More particularly, as the contracted or deflated outer shell 20a expands or inflates, CSF flows into the void space 15 through the openings 40 in the expanding outer shell 20b and across the cilia 25 decorated with an ameliorating agent 30, increasing the likelihood that the ameliorating agent 30 will enzymatically digest biomolecules within the CSF.

In a next step, (FIG. 1B), an inflating fluid may be introduced (e.g., via the inlet/outlet port 45) into the contracted or deflated inner core 10a, causing it to inflate or expand. Advantageously, as the contracted or deflated inner core 10a expands, the initially- or partially-treated CSF in the void space 15 is forced through the openings 40 in the expanded outer shell 20b. As the CSF exits the openings 40, the untreated CSF flows across the cilia 25 decorated with an ameliorating agent 30, increasing the likelihood that the ameliorating agent 30 will enzymatically digest biomolecules within the CSF.

In a next step (FIG. 1C) the inflating fluid previously introduced into the expanded inner core 10b and into the expanded outer shell 20b may be expelled from the expanded inner core 10b and the expanded outer shell 20b, causing each to deflate or contract to an at-rest state exemplified by a contracted or deflated inner core 10a and a contracted or deflated outer shell 20a. Advantageously, as the expanded outer shell 20b deflates or contracts, CSF flows across the cilia 25 decorated with an ameliorating agent 30, increasing the likelihood that the ameliorating agent 30 will enzymatically digest biomolecules within the CSF.

Another embodiment of a method of and system for localized fluid flow across elements (e.g., cilia) that have been decorated with an ameliorating agent is shown in FIGS. 2A through 2C. In some embodiments, the (e.g., flexible or collapsible, solid) structure or substrate 200 may be introduced into the SAS, without requiring circulating an ameliorating agent. In some applications, the structure or substrate 200 may be implanted into the SAS via a catheter. The CSF may be selectively circulated (e.g., naturally, by actively pumping the CSF, and/or by passively pumping the CSF) past the stationary or substantially stationary ameliorating agent. Active and passive pumping, as well as the natural circulation, may take place wholly within the SAS or the CSF may be routed in and out of the SAS. The source and power for the hydraulic or pneumatic actuation may be located outside of the SAS. Although the various embodiment of the invention are described in conjunction with hydraulically- or pneumatically-actuated surfaces, the structure may, alternatively or additionally, include a shape memory surface. Passive pumping may include a peristaltic or other forward displacement pump or may use pressure changes within the body to power circulation of CSF in the embodied system. In some implementations, the structure or substrate 200 may include a monolithic bistable substrate 205a, 205b having a plurality of appendages 210 that form a plurality of invaginated 210a and extroverted 210b structures between structure body 215. As shown in FIG. 2B, a plurality of cilia 220 may be integral with or fixedly attached to the outer peripheral surface of the appendages 210, so as to project from the outer peripheral surface of the extroverted appendages 210b, as well as to the peripheral surface of each invaginated appendage 210a and to the structure body 215, so as to cover the pockets formed thereby. Advantageously, in operation, varying amounts of an ameliorating agent may be decorated on or attached to each of the appendages 210 and body 215, including the cilia 220.

The structure or substrate 200 may also include an inlet/outlet port 225 to provide fluid communication between the bistable substrate 205a, 205b and a (e.g., hydraulic, pneumatic, and so forth) source that is capable of selectively expanding and contracting the bistable substrate 205a, 205b, respectively, by introducing a fluid into and removing a fluid from the inside of the substrate 205a, 205b.

From an at-rest state (FIG. 2A) in which the bistable substrate 205a is deflated or substantially deflated, in a first step (FIG. 2C), an inflating fluid may be introduced (e.g., via the inlet/outlet port 225) into the bistable substrate 205a, causing it to inflate or expand 230. Advantageously, as the bistable substrate 205b and the appendages 210b expand 230, the expanding substrate 205b and expanding appendages 210b mix the CSF, exposing a greater volume of the CSF to cilia 220 (FIG. 2B) decorated with an ameliorating agent, increasing the likelihood that the ameliorating agent will enzymatically digest biomolecules within the CSF.

In a next step, fluid previously introduced to expand the substrate 205b and appendages 210b may be expelled, causing the substrate 205b to deflate or contract 235 to an at-rest state (FIG. 2A). Once again, as the bistable substrate 205a and the appendages 210a contract 235, the contracting substrate 205a and contracting appendages 210a mix the CSF, exposing a greater volume of the CSF to cilia 220 decorated with an ameliorating agent, increasing the likelihood that the ameliorating agent will enzymatically digest biomolecules within the CSF. Thus, the numerous expansion and contraction cycles of the structure or substrate 200 produce a mixing motion of the CSF, further increasing interaction between the CSF and the ameliorating agent-coated cilia 220, as well as the likelihood that the ameliorating agent will enzymatically digest biomolecules within the CSF.

A further embodiment of a method of localized fluid flow across elements (e.g., fenestrations) that have been decorated with an ameliorating agent is shown in FIG. 3. In some embodiments, the (e.g., flexible or collapsible, solid) structure or substrate 300 may be introduced into the SAS, without requiring the circulation of an ameliorating agent. In some applications, the structure 300 may be implanted into the SAS via a catheter. The CSF may be selectively circulated (e.g., naturally, by actively pumping the CSF, and/or by passively pumping the CSF) past the stationary or substantially stationary ameliorating agent. Hence, CSF flow may be at or beyond natural CSF flow rates. Active and passive pumping, as well as the natural circulation, may take place wholly within the SAS or the CSF may be routed in and out of the SAS. The source and power for the hydraulic or pneumatic actuation may be located outside of the SAS. The surfaces and structures may be made of any suitable compliant and resilient biocompatible material, including polymer, elastomer, thermoplastic elastomer (TPE), etc. Although various embodiments and implementations of the invention are described in conjunction with hydraulically- or pneumatically-actuated surfaces, the structure may, alternatively or additionally, include a shape memory surface.

In some implementations, the structure of substrate 300 may include a substrate 305 having a plurality of appendages (i.e., fenestrations 310) and gaps 315. Advantageously, varying amounts of an ameliorating agent 350 may be decorated on or attached to each of the fenestrations 310.

In operation, after the substrate 305 has been introduced into the SAS, the substrate 305 may be alternatingly expanded and contracted as previously described. The numerous expansion and contraction cycles of the structure 300 produce a mixing motion of the CSF, further increasing interaction between the CSF and the ameliorating agent 350 decorated on the fenestrations 310, as well as the likelihood that the ameliorating agent will enzymatically digest biomolecules within the CSF. Alternatively, or in addition, the substrate 305 may be vibrated or slowly rotated/twisted, back and forth, to produce micromotions. The back and forth rotational or vibrational micromotions may also increase the interaction between the CSF and the ameliorating agent 350 decorated on the fenestrations 310, as well as the likelihood that the ameliorating agent will enzymatically digest biomolecules within the CSF. Advantageously, the structure 300 may be fabricated from a single material and/or a single piece of the material, reducing a risk of mechanical failure.

Figures 4A, 4B:
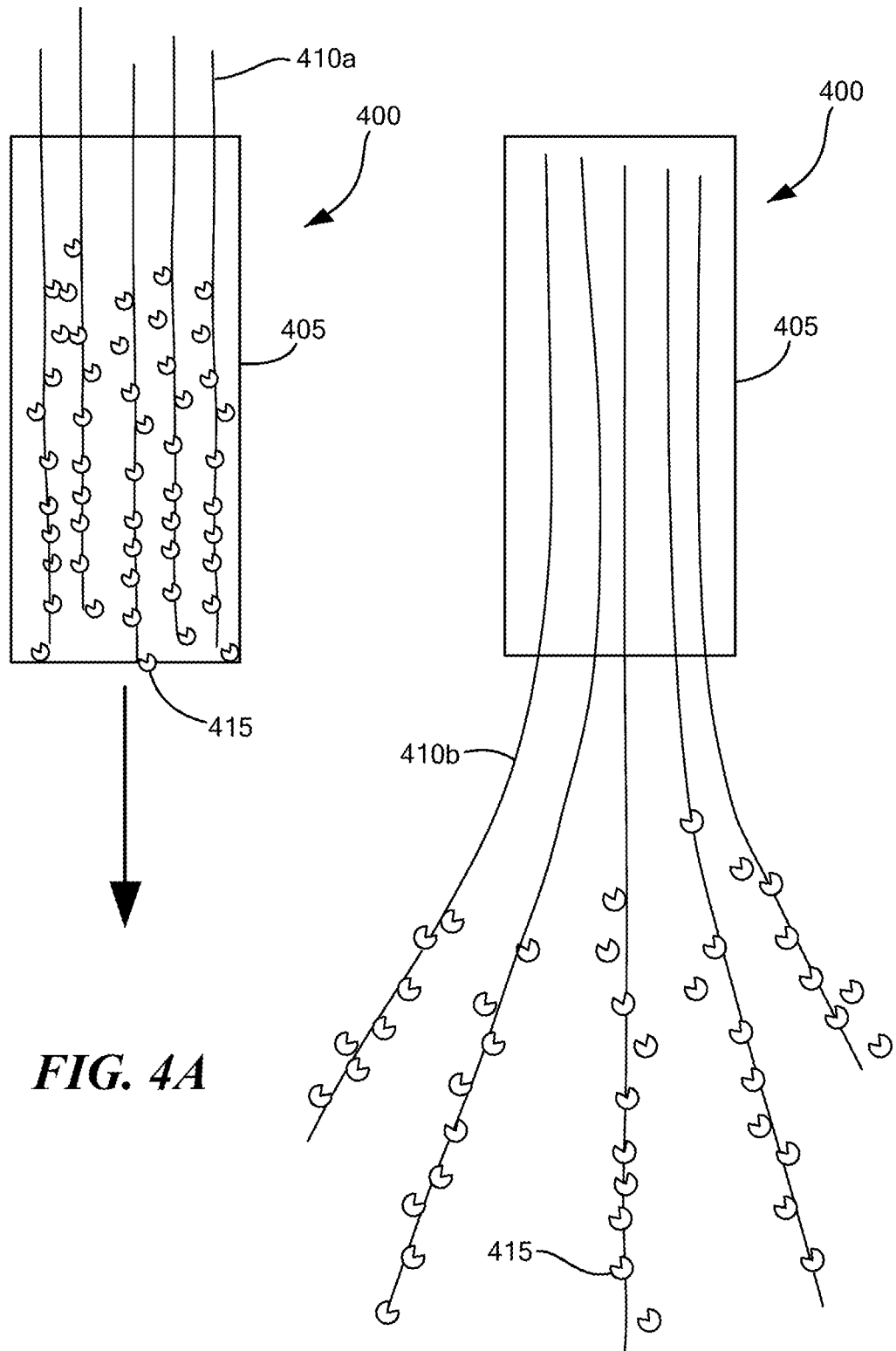
FIG. 4A shows a schematic of a tubular structure (e.g., a catheter) containing a plurality of retracted fibers decorated with an ameliorating agent, in accordance with some embodiments of the present invention.
FIG. 4B shows a schematic of the tubular structure of FIG. 4A with the fibers decorated with an ameliorating agent extending out into the CSF space, in accordance with some embodiments of the present invention.

Still another system or device for and method of localized fluid flow across elements (e.g., extendable fibers) that have been decorated with an ameliorating agent is shown in FIGS. 4A and 4B. In some applications, the structure or substrate 400 may be implanted into the SAS via a catheter. The CSF may be selectively circulated (e.g., naturally, by actively pumping the CSF, and/or by passively pumping the CSF) past the stationary or substantially stationary ameliorating agent. Hence, CSF flow may be at or beyond natural CSF flow levels (e.g., flow rate). Active and passive pumping, as well as the natural circulation, may take place wholly within the SAS or the CSF may be routed in and out of the SAS. The source and power for the hydraulic or pneumatic actuation may be located outside of the SAS. The surfaces and structures may be made of any suitable compliant and resilient biocompatible material, including polymer, elastomer, thermoplastic elastomer (TPE), etc. Although some embodiments or applications of the invention are described in conjunction with hydraulically- or pneumatically-actuated surfaces, the structure may, alternatively or additionally, include a shape memory surface.

In some embodiments, the structure 400 may include a (e.g., tubular) structure or casing (e.g., a catheter 405), containing a plurality of hair-like fibers 410a, 410b (e.g., brush fibers). Advantageously, the fibers 410a, 410b are retractable and extendable, such that, when the catheter 405 is being introduced into or withdrawn from the SAS, the fibers 410a may remain in a retracted state (FIG. 4A); but, when subjected to CSF flow (FIG. 4B), the retracted fibers 410*a* can deploy, extending out from the catheter 405 into the SAS. Optionally or alternatively, the structure or casing 400 may also be vibrated or rotated/twisted to create micromotions to facilitate local CSF motion across the extended fibers 410*b*.

Advantageously, varying amounts of an ameliorating agent 415 may be decorated on or attached to each of the fibers 410*a*, 410*b*, such that, when the fibers 410*b* are extended into the CSF space, the extended fibers 410*b* provide a large volume for interacting with the CSF, increasing interaction between the CSF and the ameliorating agent 415, as well as the likelihood that the ameliorating agent 415 will enzymatically digest biomolecules within the CSF.

Although the above embodiments have been described such that the corresponding structures have been completely implanted within the SAS, those of ordinary skill in the art can appreciate that some portions of the structures may be implanted within the SAS, while other portions may be implanted within the body of mammalian subject but outside of the SAS. Such an arrangement would require CSF to be circulated from the SAS, through the structure that is implanted outside of the SAS, and then returned back into the SAS. The source and power for the hydraulic or pneumatic actuation may be located outside of the SAS.

Figure 5:
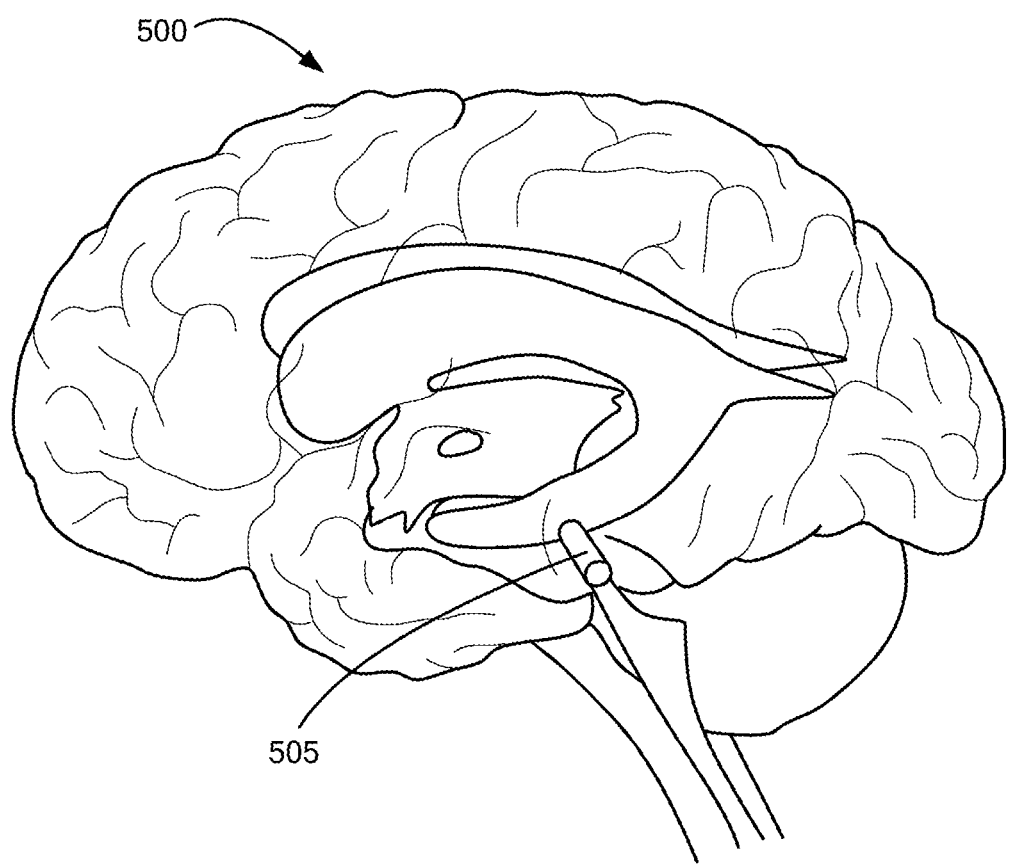
FIG. 5 shows schematic of a coated stent placed in a cerebral aqueduct, in accordance with some embodiments of the present invention.

A further method of localized fluid flow using a structure that has been decorated with an ameliorating agent is shown in FIG. 5. In some embodiments, an embodied structure 505 may be introduced (i.e., completely implanted) into the SAS (e.g., in the cerebral aqueduct, near the fourth ventricle, and so forth), without requiring circulating an ameliorating agent. Instead, CSF may be selectively circulated in the presence of the ameliorating agent naturally, by actively pumping the CSF, and/or by passively pumping the CSF. Active and passive pumping of the CSF, as well as the natural circulation of the CSF, may take place wholly within the SAS or the CSF may be routed in and out of the SAS.

As shown in FIG. 5, in some implementations, the structure 500 may include a stent 505 having an inner peripheral surface to which an ameliorating agent may be coated, decorated, or otherwise applied to. Placing the stent 505 within the SAS in a location that experiences relatively high CSF flow (e.g., in the cerebral aqueduct, near the fourth ventricle, and so forth) increases interaction between the CSF and the ameliorating agent, as well as the likelihood that the ameliorating agent will enzymatically digest biomolecules within the CSF.

In another implementation, the structure 500 may include a thin sheet (e.g., planar, contoured, helical, etc.) on which an ameliorating agent may be coated or otherwise applied. Placing the coated sheet within the SAS in a location that experiences relatively high CSF flow (e.g., over the motor cortex, in a SAS cistern, and so forth) increases interaction between the CSF and the ameliorating agent, as well as the likelihood that the ameliorating agent will enzymatically digest biomolecules within the CSF.

Enzymatic Digesting and Size Filtering

Referring to FIG. 6, an exemplary embodiment of a system 600 that combines enzymatic digesting (i.e., using an enzymatic digester) and size filtering is shown. In some applications, the system 600 may include a plurality of size-charge filters 605*a*, 605*b* in combination with a structure containing an ameliorating agent 610 (e.g., an enzymatic digester).

The loop-flow embodiment shown in FIG. 6 takes advantage of countercurrent exchange. In operation, untreated CSF having the highest concentrations of small components 615, large non-toxic biomolecules 620, and large biomolecules 625*a* may enter the system 600 flowing in a first direction (e.g., to the right) away from the highest concentrations.

After the high concentration, untreated CSF enters the system 600, it encounters a first size-charge filter (e.g., a porous wall) 605*a*, separating the high concentration, untreated CSF traveling in a first direction from lower concentration, filtered and treated CSF traveling in a second, and opposite direction. The size of the openings in the first porous wall 605*a* may be selected to allow the small components 615 to pass the filter, which occurs as the small components 615 typically flow from the higher concentration to the lower concentration. As the small components 615 filter across the first porous wall 605*a*, some of the smaller components 615 are separated (i.e., filtered away) from the large non-toxic biomolecules 620 and the large biomolecules 625*a*. The filtered, small components 615 may flow out of the system 600 with treated CSF.

In a next step, the filtered CSF may encounter or come into contact with an ameliorating agent 610 (e.g., in an enzymatic digester). Whereas the ameliorating agent 610 may be selected so as to have little or no effect on the remainder of the small components 615 or on the large non-toxic biomolecules 620, by design, the agent 610 ameliorates (e.g., enzymatically digests) the large toxic biomolecules 625*a*, causing a reduction in the size of these ameliorated biomolecules 625*b*.

As the treated CSF continues to flow to the right, out of the enzymatic digester and the ameliorating agent 610, the treated CSF encounters a second size-charge filter (e.g., porous wall) 605*b* to separate ameliorated biomolecules 625*b* from the large non-toxic biomolecules 620 that are unaffected by the enzymatic digestion. The size of the openings in the second porous wall 605*b* may be selected to allow the ameliorated biomolecules 625*b* to pass across the filter 605*b*, which occurs as the ameliorated biomolecules 625*b* tend to flow from the higher concentration to the lower concentration. Some small components 615 may also filter across the second porous wall 605*b*. Those small components 615 and the ameliorated biomolecules 625*b* that were filtered out by the second porous wall 605*b* may be discharged (e.g., as waste) to the bladder or other location. The treated CSF, containing some of the small components 615 and the large non-toxic biomolecules 620, may then exit the system 600 to the left (e.g., in a counter current flow pattern).

Figure 17:
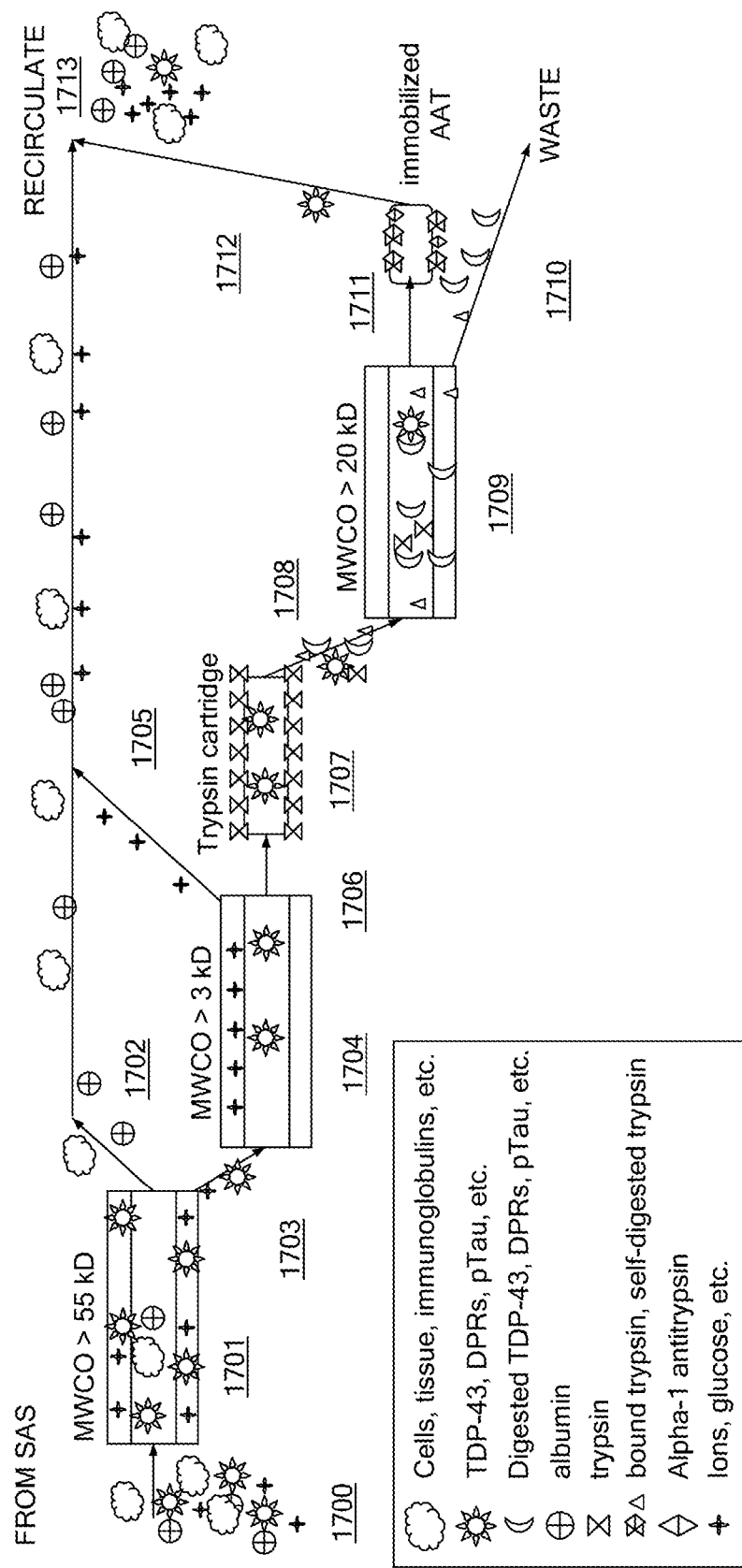
FIG. 17 shows a schematic of a three-stage tangential flow filtration subsystem integrated with an enzymatic cartridge and follow-on getter, in accordance with some embodiments of the present invention.

Referring to another filtration system depicted in FIG. 17, there shown is a schematic of an embodiment of tangential flow filtration stages in combination with an enzymatic cartridge 1707. The system 1700 shows a fluid (e.g., CSF) withdrawn from the subarachnoid space (SAS) of the patient by means of a catheter and circulated to the filtration subsystem 1700. The fluid at this point comprises multiple potential components, including cells, tissue fragments, immunoglobulins, targeted toxic proteins of interest (e.g., TDP-43, dipeptide repeat proteins (DRPs), phosphorylated tau, and so forth), albumin, glucose, ions, and other species. The CSF enters a first stage of tangential flow filtration (TFF) 1701 wherein the CSF is separated into a retentate 1702 and permeate 1703 stream by a membrane with a high molecular weight cutoff (MWCO). For example, in the first stage, a MWCO of about 55 kDa would pass cells and albumin, but filter smaller proteins, glucose, and ions. The permeate 1703 may then be passed to the second stage TFF 1704 having a lower MWCO (e.g., about 3 kDa). The second stage 1704 filters as permeate 1705 smaller species such as ions and glucose, whereas larger proteins are retained as retentate 1706. The retentate 1706 may then be passed to an enzymatic cartridge 1707. In this cartridge 1707, an enzyme (e.g., trypsin) digests the target protein and passes the fragments in the output 1708. Advantageously, to increase the residence time and, accordingly, the exposure of the retentate 1706 to the enzyme (e.g., trypsin) disposed in and/or decorated on the cartridge 1707, the flow of CSF may follow a dual flow pattern through the cartridge 1707, i.e., the mobile phase may be passed in bi-directional flow across the stationary phase a single time or repeatedly. In this pattern, the CSF is aspirated and then ejected in one or more cycles before passing to the output. In this variation, the output port of the cartridge 1707 may be the same as the input port of the cartridge 1707.

The output 1708 of the enzymatic cartridge 1707 may then be passed to a third TFF stage 1709 with a MWCO sufficient to separate the digested fragments from whole protein.

The digested fragments, potentially including self-digested trypsin, may then be passed to waste 1710. The retentate stream 1712 potentially contains whole target protein that was undigested and enzyme that came detached from the substrate in 1707. This stream may then be passed to a second cartridge 1711 containing a "getter," for example, immobilized Alpha-1 antitrypsin which serves to capture any free-floating trypsin released from the first cartridge 1707. More specifically, to prevent or minimize loose enzyme previously disposed in and/or decorated on the first cartridge 1707 from reaching the SAS via the treated CSF, the getter may be located downstream of the first cartridge 1707, such that the getter grabs or captures loose or free enzymes contained in the output stream 1712. In some implementations, when the enzyme is trypsin, suitable getter materials may be Alpha-1 antitrypsin AAT; whereas, benzidiamide, benzamidine (e.g. Benzamidine Sepharose 4 Fast Flow (High Sub), G.E. Healthcare Lifescience, Cytiva), and the like may be used more generally for proteases. In some variations, getter materials may be immobilized on surfaces, such as tube lumina, beads, fine mesh, cilia, fiber structures, and so forth. Finally, the output stream 1712 is combined with the other streams 1702 and 1705 into a stream 1713 that is reintroduced and recirculated into the patient. The MWCO of the stages may be adjusted to best suit the desired target species.

Advantageously, this filtration system, by nature of the tangential flow filtration stages will be less susceptible to clogging by tissue and cell debris. Furthermore, the configuration removes the digestion fragments of the toxic proteins from the enzymatic cartridge 1707. Additionally, the second cartridge captures any enzyme that detaches from the first cartridge. Finally, the cartridges have a cleaner feedstream due to the earlier TFF stages.

Fluid Flow and Augmenting Fluid Flow

While, in some implementations of the systems, methods and devices described herein, allowance for natural CSF flow is acceptable, in other implementations, use of active and/or passive pumping techniques may be desirable to control the CSF flow. Pumping techniques may include pumps, valves, actuators, and combinations thereof. For example, pumps may include a peristaltic pump, a rotary vane pump, an Archimedes screw, an air bladder, a pneumatic bladder, a hydraulic bladder, a displacement pump, an electromotive pump, a passive pump, an autopump, a valveless pump, a bi-directional pump, and combinations thereof. Valves may include a one-way valve, a bicuspid valve, a tricuspid valve, a ruby valve, and combinations thereof.

Amelioration techniques that include use of an ameliorating agent (as opposed to those that use a treatment system) can entail an active (or positive) implementation of flow from one location (e.g., within the SAS or from outside of the SAS) to another location that is either within or outside of the SAS. Indeed, by presenting an ameliorating agent with a high circulation of CSF, the interaction between the CSF and the ameliorating agent may be increased, which increases the likelihood that the ameliorating agent will enzymatically digest biomolecules within the CSF. In implementing fluid flow, the CSF may circulate past a stationary or substantially stationary structure decorated or coated with an ameliorating agent, the structure decorated or coated with an ameliorating agent may circulate past the CSF, or both the CSF and the structure decorated or coated with an ameliorating agent may circulate past each other.

In the case of the CSF circulating, such movement may occur as part of the natural flow of the fluid or, in the alternative, the natural flow may be augmented actively or passively. Such active or passive augmentation (i.e., pumping) may occur concurrently, periodically, sequentially, and so forth. Furthermore, as described above, the CSF may be made to circulate completely within the SAS or, in the alternative, the CSF may be transported out of the SAS but later reintroduced into the SAS, after the CSF has circulated past the ameliorating agent.

As previously mentioned, pressure changes and/or volume changes associated with the naturally flowing fluids in the SAS and/or fluids whose flows are artificially augmented should be regulated to avoid or minimize effects that may result in spinal headaches or even death in the subject. Thus, when fluid is removed from the SAS and/or reintroduced into the SAS, the pressure transient may depend, at least in part, on the duty cycle and the flow rate of the procedure involved.

Although, in some applications, turbulent mixing of the CSF may be desirable, conventionally, high levels of fluid motion within the CSF space may also cause discomfort to the subject. Hence, fluid flow—whether actively pumped within the SAS, passively pumped within the SAS, or when pumped out of the SAS and reintroduced back into the SAS—should be controlled to avoid excessive or unwanted mixing of the fluid. Indeed, while some mixing is desirable and beneficial, excessive or unwanted mixing is generally not preferred.

The source and power for actuation associated with system components may be located outside of the SAS. The power required by the pump can be estimated by:

$$P_{h(kW)} = q\,\rho\,g\,z/(3.6\times 10^6),$$

where:
$P_{h(kW)}$=hydraulic power (kW),
q=flow capacity (m$^3$/h),
$\rho$=density of fluid (kg/m$^3$),
g=gravity (9.81 m/s$^2$), and
z=differential head (m).

The required flow capacity (q) is approximately 20 mL/h, or about 20×10$^{-6}$ m$^3$/h. The density ($\rho$) of CSF is about 1.00059×10$^3$ kg/m$^3$. The average spinal length (z) is about 0.5 m. With an efficiency in the pump of 0.6, this gives P=27 µW.

A lithium thionyl chloride battery (e.g., an LTC-EP-200014 battery manufactured by EaglePicher of St. Louis, MO) has a capacity of 8 Ah. Thus, this battery could, in principle, operate for about 8 Ah/(30 µW/3 V)=8×10$^5$ h. System losses would reduce this time value, while natural flows of the CSF would reduce the pump requirements, if not mitigate pump requirements entirely.

Figure 7B:
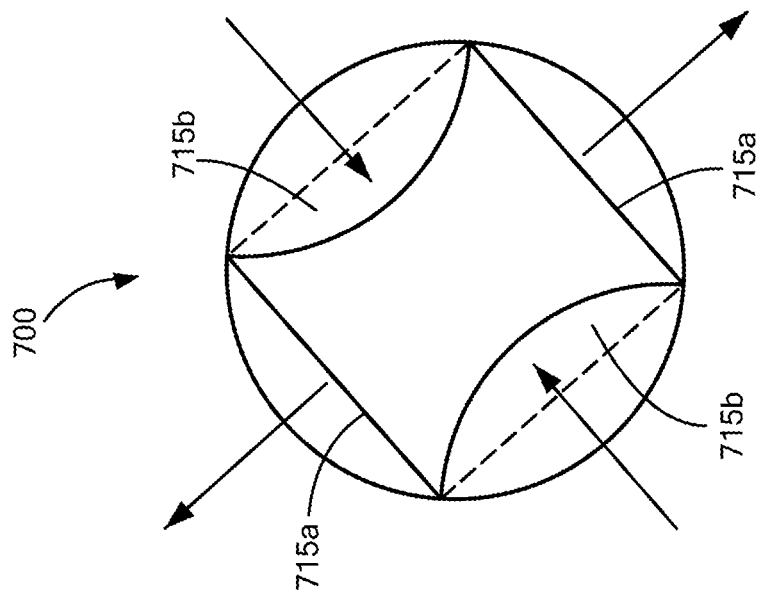
FIG. 7B shows a schematic top view of the peristaltic pump of FIG. 7B.
Figure 7A:
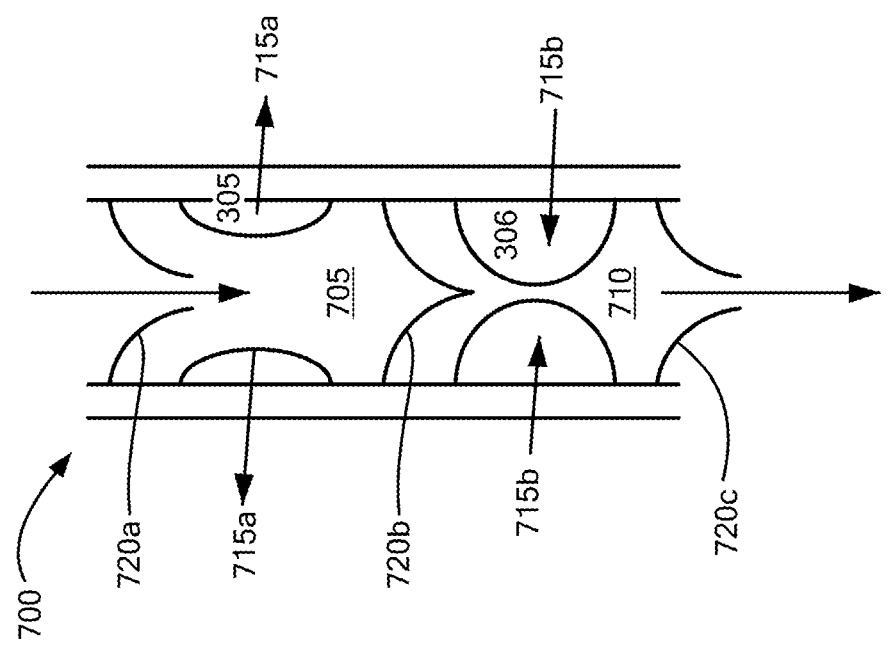
FIG. 7A shows a schematic of a side view of a hydraulic peristaltic pump, in accordance with some embodiments of the present invention.

Referring to FIGS. 7A and 7B, an exemplary monolithic, hydraulically-activated peristaltic pump 700 capable of being implanted within the SAS or elsewhere within the body of the subject is shown. In some embodiments, the pump 700 may include a number of chambers 705, 710 in which are located a pair of opposing selectively inflatable bladders 715a, 715b. The two-chamber pump 700 shown in FIG. 7A includes an antechamber 705 and a post chamber 710, although a greater number of chambers is also possible. Upstream and downstream of each chamber 705, 710 may be a bicuspid valve 720a, 720b, 720c, which may be structured and arranged proximate the bladders 715a, 715b. Advantageously, the one-way nature of the bicuspid valves 720a, 720b, 720c prevents retroflow back into the pump 700 or into a previous chamber 705, 710.

Actuating the bladders 715a, 715b, for example, by alternatingly inflating and deflating the bladders 715a, 715b sequentially causes fluid (e.g., CSF or ISF) to enter the antechamber 705 though a first bicuspid valve 720a. For example, as the bladders 715a in the antechamber 705 are deflated or shrunken from a previously inflated or distended state, the shrinking of the bladder 715a causes a reduction of pressure within the antechamber 705, drawing fluid from outside the antechamber 705 into the antechamber 705 via the first bicuspid valve 720a. As the bladders 715b in the post chamber 710 are contemporaneously deflated or shrunk from a previously inflated or distended state, the shrinking of the bladder 715b causes a reduction of pressure in the post chamber 710, drawing fluid from the antechamber 705 into the post chamber 710 via the second bicuspid valve 720b. In a next cycle, as the bladders 715b in the post chamber 710 are inflated from a previously deflated or shrunken state, the distending of the bladders 715b forces fluid from the post chamber 710 out of the post chamber 710 via the third bicuspid valve 720c.

In some embodiments, a structure having a passive pump that can be completely implanted in the (e.g., cranial or spinal) SAS may be desirable. Referring to FIGS. 8A through 8C, a structure 800 having a passive pump 805 that uses the normal pressure fluctuations in the CSF itself to circulate fluid through the structure 800 is shown. In some variations, the structure 800 may also be connected to an implanted subcutaneous adapter, which would facilitate introduction, maintenance, and removal of the structure 800.

In some applications, the structure 800 may include a cartridge 810 (e.g., a catheter body) having a first opening and a second opening, at which a first, one-way valve 815a and a second, one-way valve 815b are operatively disposed. Each of the openings and one-way valves 815a, 815b are in fluid communication with the CSF space 820.

The cartridge 810 may be rigid or flexible. In some variations, the rigid cartridge 810 may include a plurality of metal spiral or helical structures that may be configured to support a radially patent lumen. Although rigidity is desirable to promote fluid flow into the cartridge 810, the cartridge 810 should remain flexible enough to conform to anatomical contours within the SAS 820. In other variations, the cartridge may be flexible (e.g., elastic), such that as the (e.g., compressed) shape of the cartridge 810 recovers, recovery of the shape may drive the inflow of fluid from the SAS into the cartridge 810.

In some embodiments a passive pump 805 (e.g., an air- or auto-bladder) may be located within the cartridge 810. An ameliorating agent 825 may be decorated on the interior surfaces of the cartridge 810.

Although the structure 800 will be described as having been fully implanted in the spinal SAS, those of ordinary skill in the art can appreciate that it can also be implanted in the cranial SAS. For example, in one implementation, the structure 800 may be implanted in the spinal SAS, extending significantly in the rostrocaudal direction, so that CSF circulates and is ameliorated between the brainstem region and the lumbar region. Advantageously, such a location induces mixing with cerebral SAS fluid, as well as spinal SAS fluid. In another implementation, a structure 800 may be implanted in the cranial SAS, so as to operably induce flow between locations therein (e.g., between the cisterna magna and the frontal lobe, between the two lateral hemispheres, and so forth).

While the operation of a passive pump 805 will be described in a number of stages, in practice, the sequence of steps should be considered as a more continuous process. In a first stage (FIG. 8A), the passive pump 805 within the cartridge 810 may be in an inflated state, such that the pressure (P') within 830 the passive pump 805 is equal to the (e.g., relatively low) pressure (P) in the spinal space 820. As shown in FIG. 8B, as the pressure (P) in the spinal space increases, the increasing external pressure (P) compresses the passive pump 805, causing it to deflate. As the passive pump 805 deflates within the cartridge 810, pressure in the cartridge (P') decreases (i.e., below the external pressure (P)), causing fluid to flow into the cartridge 810 through the first one-way valve 815a, while the second one-way valve 815b remains closed. Advantageously, as untreated CSF enters the cartridge 810 via the first one-way valve 815a, untreated CSF may be exposed to a surface area decorated with an ameliorating agent 825, increasing the likelihood that the ameliorating agent 825 will enzymatically digest biomolecules within the CSF.

When the pressure (P) in the SAS decreases again, the passive pump 805 inflates again, forcing treated CSF from within the cartridge 810 out of the cartridge via the second one-way valves 815b. Because the inflating passive pump 805 creates an overpressure within the cartridge 810, the first one-way valve 815a remains closed.

In another embodiment, the pump 805 may be connected to an external source of pressure variation, either an active gas reservoir or pump, or another location in the anatomy wherein the pressure changes regularly (e.g., the abdominal or pleural cavity). This external source of pressure variation then drives the balloon actuator in the pump.

Figure 8D:
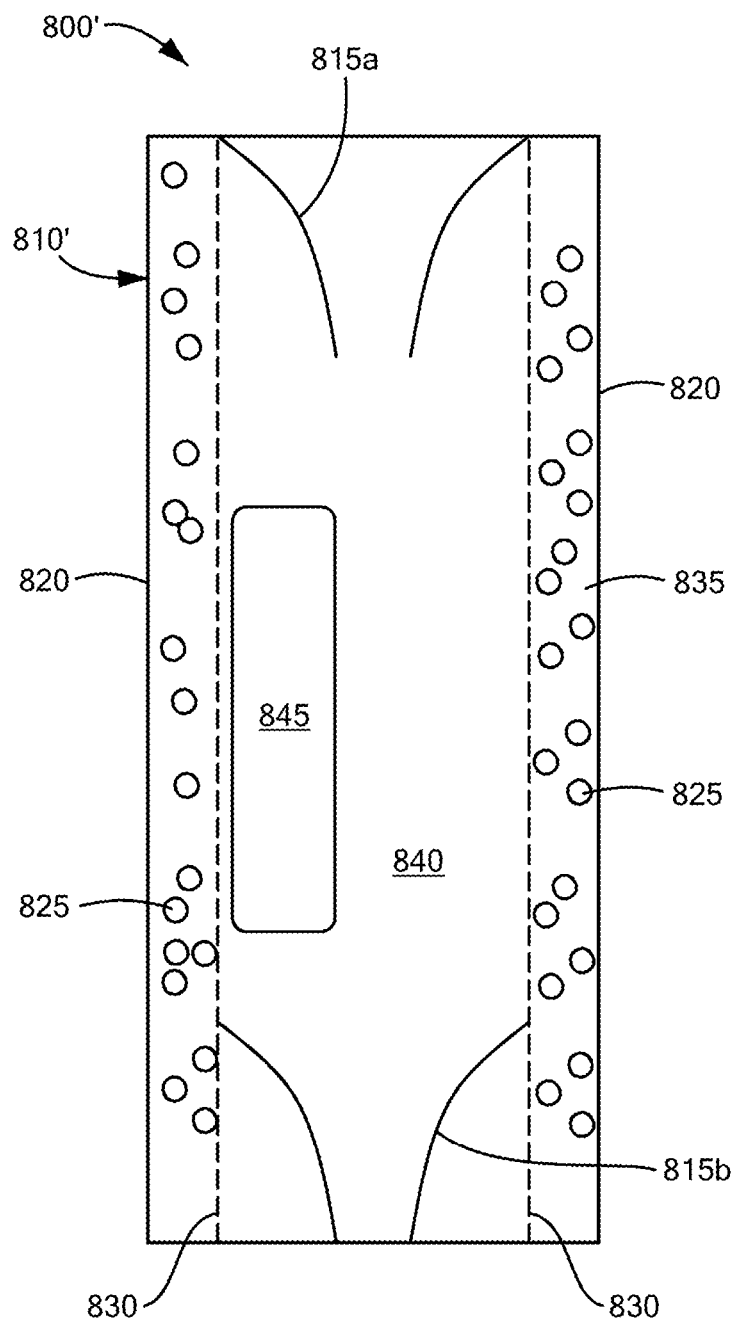
FIG. 8D shows a schematic of a passive pump having a porous divider, in accordance with some embodiments of the present invention.

In yet another embodiment depicted in FIG. 8D, the device 800' is provided with a porous divider 850 that separates the ameliorating agent 825 from CSF circulating through the lumen 830 of the device. Advantageously, this configuration presents a significantly larger surface of ameliorating agent to the CSF than that which could be decorated on the interior surfaces of the cartridge 810.

Referring to FIG. 8D, the embodiment includes a cartridge 810' that includes a porous wall (or divider) 850. The porous wall 850 separates the main lumen 830 from the separate lumen 835. In some variations, the porous wall 850 may be concentric and coaxial with the cartridge 810. However, in some applications, the porous wall 850 may be eccentric with respect to the cartridge 810.

In some implementations, an ameliorating agent 825 may be provided and confined within the separate lumen 835, while CSF is circulated through the main lumen 830. As CSF flows through the main lumen 830, the untreated or partially-treated CSF has an opportunity to interact with the ameliorating agent 825, which, for example, may be decorated on a plurality of beads. Advantageously, the size of the pores in the porous wall 850 is dimensioned to retain and confine the beads coated with the ameliorating agent 825 within the separate lumen 835, while permitting biomolecules to pass through the porous divider 850. A pair of one-way valves 815a, 815b are formed at opposing ends of the cartridge 810, in fluid communication with the CSF space. A passive pump (e.g., an autopump) 805 may be located within the main lumen 830.

The operation of 800' is similar to that of 800, with the distinction that the ameliorating agent 825 is sequestered behind a porous wall 850.

Figure 8E:
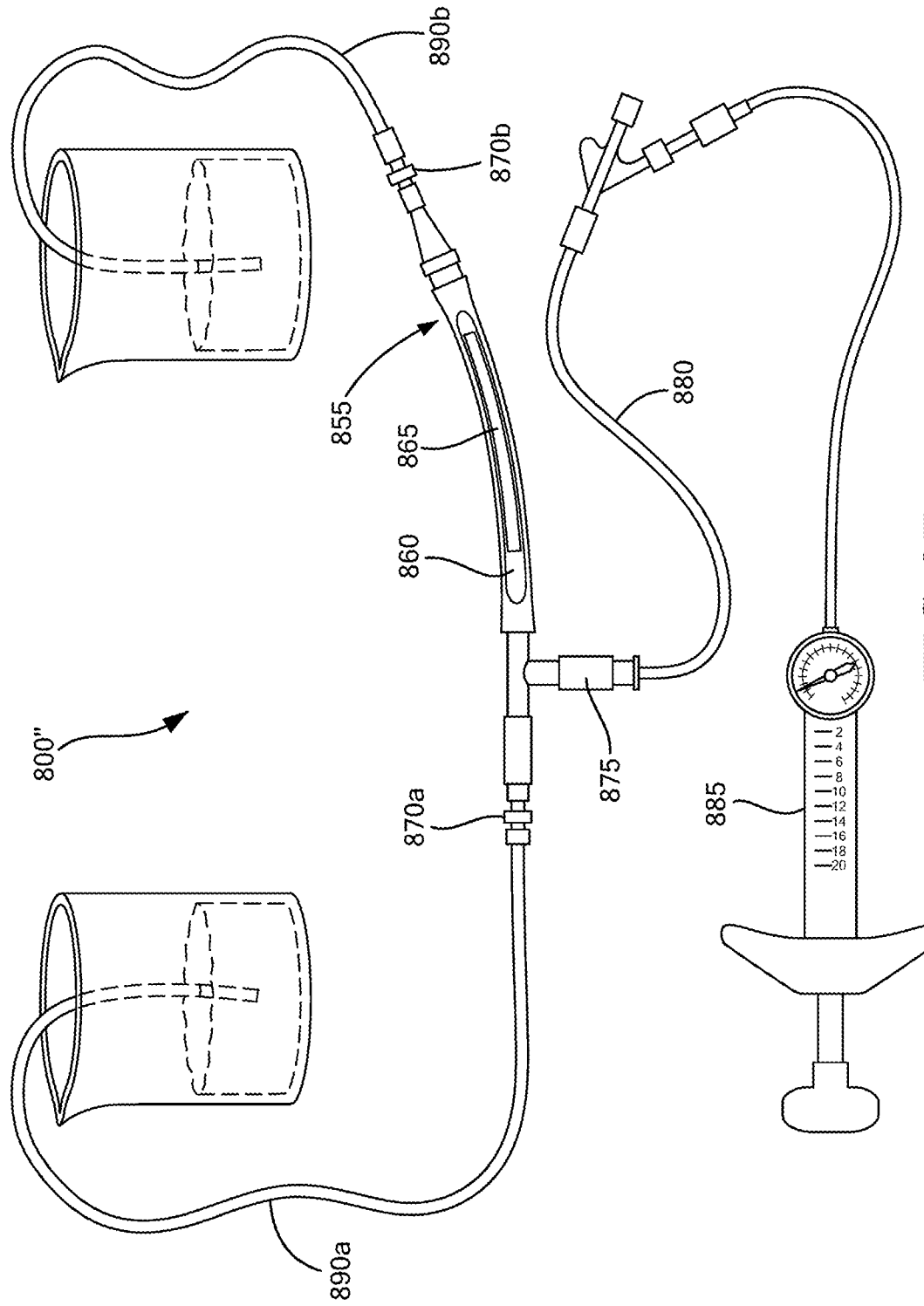
FIG. 8E shows an image of an open-ended balloon catheter pump, in accordance with some embodiments of the present invention.

Referring to FIG. 8E, a laboratory scale embodiment of an open-ended, balloon catheter autopump 800" for continuous ex corpore use is shown to illustrate the principles of the autopump 800". In some implementations, the autopump 800" includes an inflatable balloon 860 disposed within the lumen of a rigid or substantially rigid catheter 855. In some variations, a cartridge 865 may also be disposed within the lumen of the catheter 855. An ameliorating agent may be disposed within the cartridge 865. Alternatively, an ameliorating agent may be adhered to the inner surface of the cartridge 865.

A first check valve 870a may be disposed upstream of the balloon catheter 855 and a second check valve 870b may be disposed downstream of the balloon catheter 855. A T-connection 875 may be disposed upstream of the balloon catheter 855 but downstream of the first check valve 870a. A conduit 880 providing fluid communication between a pressure source 885 and the balloon 860 is disposed in the T-connection 875. The pressure source 885 is an external source of pressure variation, either an active gas reservoir or a pump, that is structured and arranged to selectively or cyclically inflate and deflate the balloon 860 to move CSF through the autopump 800".

In operation, an upstream end 890a of autopump 800" may be inserted into a first location of the mammalian subject to provide fluid communication with the CSF space, while a downstream end 890b of autopump 800" may be inserted into a second location of the mammalian subject to provide fluid communication with the CSF space 820. In some applications, each inflation and deflation cycle of the balloon 860 draws in and expels a volume of CSF, which is then exposed to an ameliorating agent contained in or adhered to a cartridge 865 disposed within or in fluidic communication with the catheter 855. More specifically, as the balloon 860 is deflated (e.g., by the pressure source 885), a pressure differential is created between the catheter 855 lumen and exterior. This pressure differential causes the first (e.g., upstream) check valve 870a to open and the second (e.g., downstream) check valve 870b to remain closed, so that fluid is drawn into the catheter 855 from the upstream end 890a. Once the pressure equilibrates, both check valves 890a, 890b close. Next, as the balloon 860 is inflated (e.g., by the pressure source 885), a pressure differential is created between the catheter 855 lumen and exterior. This pressure differential causes the second (e.g., downstream) check valve 870b to open and the first (e.g., upstream) check valve 870a to remain closed, so that fluid is expelled from and out of the catheter 855 and the cartridge 865 disposed within the catheter 855 towards the downstream end 890b.

Figure 8F:
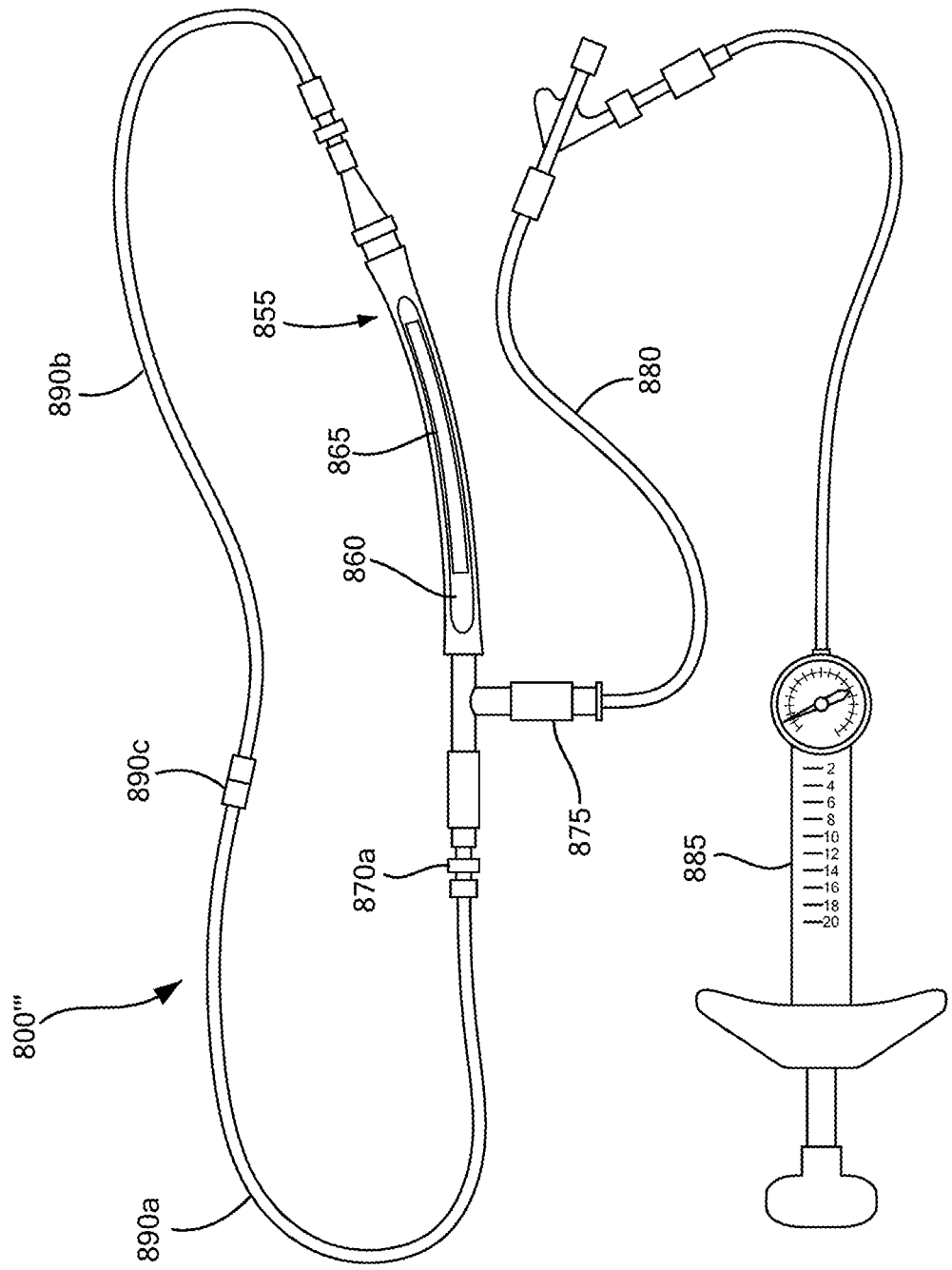
FIG. 8F shows an image of closed-ended balloon catheter pump, in accordance with some embodiments of the present invention.

Referring to FIG. 8F, a laboratory scale embodiment of a closed-ended, balloon catheter autopump 800''' for batch ex corpore use is shown to illustrate the principles of the autopump 800". In some implementations, the autopump 800''' includes an inflatable balloon 860 disposed within the lumen of a rigid or substantially rigid catheter 855. In some variations, a cartridge 865 may also be disposed within the lumen of the catheter 855. An ameliorating agent may be disposed within or in fluidic communication with the cartridge 865. Alternatively, an ameliorating agent may be adhered to the inner surface of the cartridge 865. In operation, after a volume of fluid, i.e., a batch, has been removed from the patient, the volume of fluid may be contained in a closed-loop, in which, due to a dual flow capability, the removed volume of fluid can be introduced and re-introduced, back and forth or sequentially repeatedly, through the cartridge 865 to increase the residence time and the exposure of the removed fluid to the ameliorating agent within the cartridge 865. The treated volume of fluid, i.e., the batch, may then be returned to the patient from the closed-loop once treatment of that batch has been completed. An additional batch of fluid can then be removed from the patient and the batch treatment process repeated.

More specifically, a first check valve 870a may be disposed upstream of the balloon catheter 855 and a second check valve 870b may be disposed downstream of the balloon catheter 855. A T-connection 875 may be disposed upstream of the balloon catheter 855 but downstream of the first check valve 870a. A conduit 880 providing fluid communication between a pressure source 885 and the balloon 860 is disposed in the T-connection 875. The pressure source 885 is an external source of pressure variation, either an active gas reservoir or a pump, that is structured and arranged to selectively or cyclically inflate and deflate the balloon 860 to move CSF through the autopump 800'''.

In operation, the upstream end 890a and the downstream end 890b of autopump 800" are physically attached at junction 890c. In some applications, each inflation and deflation cycle of the balloon 860 draws in and expels a volume of CSF, which is then exposed to an ameliorating agent contained in or adhered to a cartridge 865 disposed within the lumen of the catheter 855. More specifically, as the balloon 860 is deflated (e.g., by the pressure source 885), a pressure differential is created between the lumen of the catheter 855 and exterior. This pressure differential causes the first (e.g., upstream) check valve 870a to open and the second (e.g., downstream) check valve 870b to remain closed, so that fluid is drawn into the lumen of the catheter 855 from the upstream end 890a. Once the pressure equilibrates, both check valves 870a, 870b close. Next, as the balloon 860 is inflated (e.g., by the pressure source 885), a pressure differential is created between the lumen of the catheter 855 and exterior. This pressure differential causes the second (e.g., downstream) check valve 870b to open and the first (e.g., upstream) check valve 870a to remain closed, so that fluid is expelled from and out of the lumen of the catheter 855 towards the downstream end 890b.

The open-ended autopump 800" can be modified with the closed loop of the closed-ended autopump 800''' with suitable valving to access the batch of fluid from the patient, isolate the patient, treat the fluid, then return the treated batch of fluid to the patient.

Figure 13:
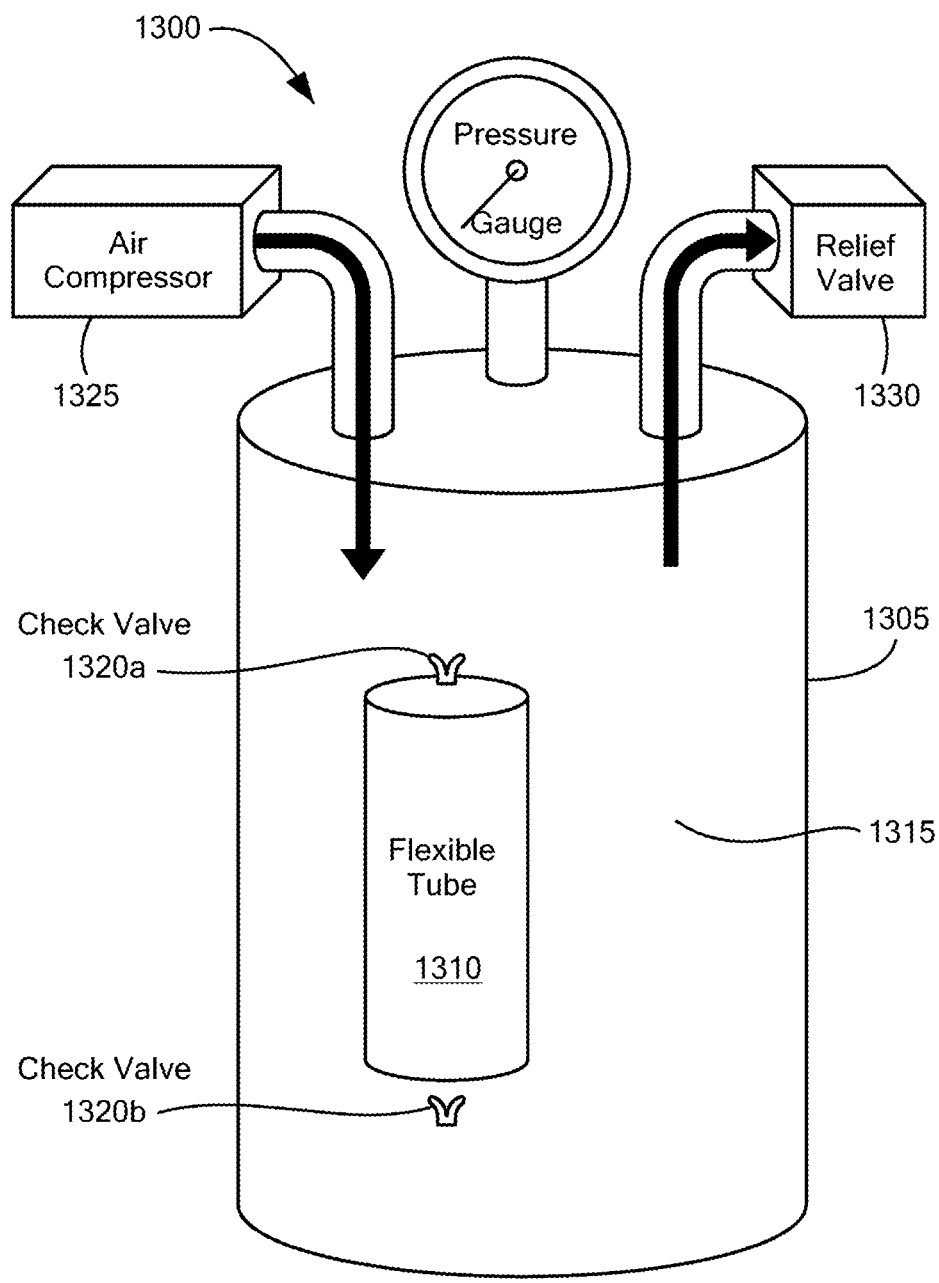
FIG. 13 shows a schematic of a pressurized chamber autopump with a flexible, closed-loop cartridge, in accordance with some embodiments of the present invention.

Referring to FIG. 13, a schematic of a laboratory scale embodiment of an autopump 1300 within a pressurized chamber 1305 is shown. In some implementations, CSF may be introduced into an arrangement that includes a (e.g., flexible tube) cartridge 1310 containing an ameliorating agent. A first conduit 1315 provides fluid communication with a first end of the cartridge 1310 from a location outside the chamber 1305 and a second conduit provides fluid communication with a second end of the cartridge 1310 to a location outside the chamber 1305. A first check valve 1320*a* may be disposed upstream of the cartridge 1310 at the first end and a second check valve 1320*b* may be disposed downstream of the cartridge 1310 at the second end. The cartridge 1310 and may be immersed in a liquid contained within the pressurized chamber 1305.

A pressure-producing source (e.g., an air compressor, a pressure differential device, and the like) 1325 capable of producing a pressure variation may be placed in fluid communication with the inner plenum space of the pressurized chamber 1305. A relief valve 1330 for bleeding off the pressure may also be placed in fluid communication with the plenum space of the pressurized chamber 1305.

In operation, a volume of CSF may be introduced into the cartridge 1310 via the first conduit 1315 via suitable fluidic connections. The pressure-producing source 1325 increases the gas (e.g., air) pressure contained within the pressurized chamber 1305 and the relief valve 1330, when opened, reduces the gas pressure within the pressurized chamber 1305. The increase in gas pressure results in an increase in liquid (e.g., water) pressure, which collapses the flexible cartridge 1310. The collapsing cartridge 1310 drives a volume of CSF out of the cartridge 1310 via second check valve 1320*b* and second conduit. When the pressurized gas is in expelled via the relief valve 1330, the liquid (e.g., water) pressure decreases, causing the flexible cartridge 1310 to expand. The expanding cartridge 1310 draws a new volume of CSF into the cartridge 1310 via the first check valve 1320*a* and first conduit 1315. The cycle can then be repeated.

Figure 14B:
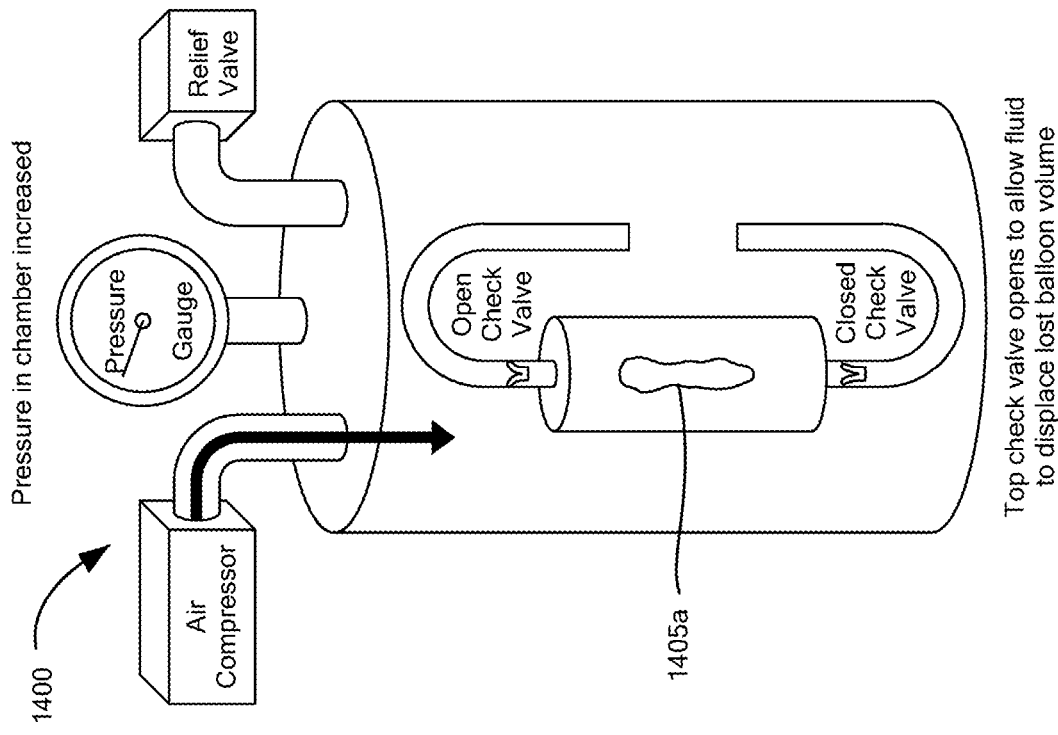
FIG. 14B shows schematic of the pressurized chamber autopump of FIG. 14A with a collapsed balloon due to an increase in surrounding pressure, in accordance with some embodiments of the present invention.
Figure 14A:
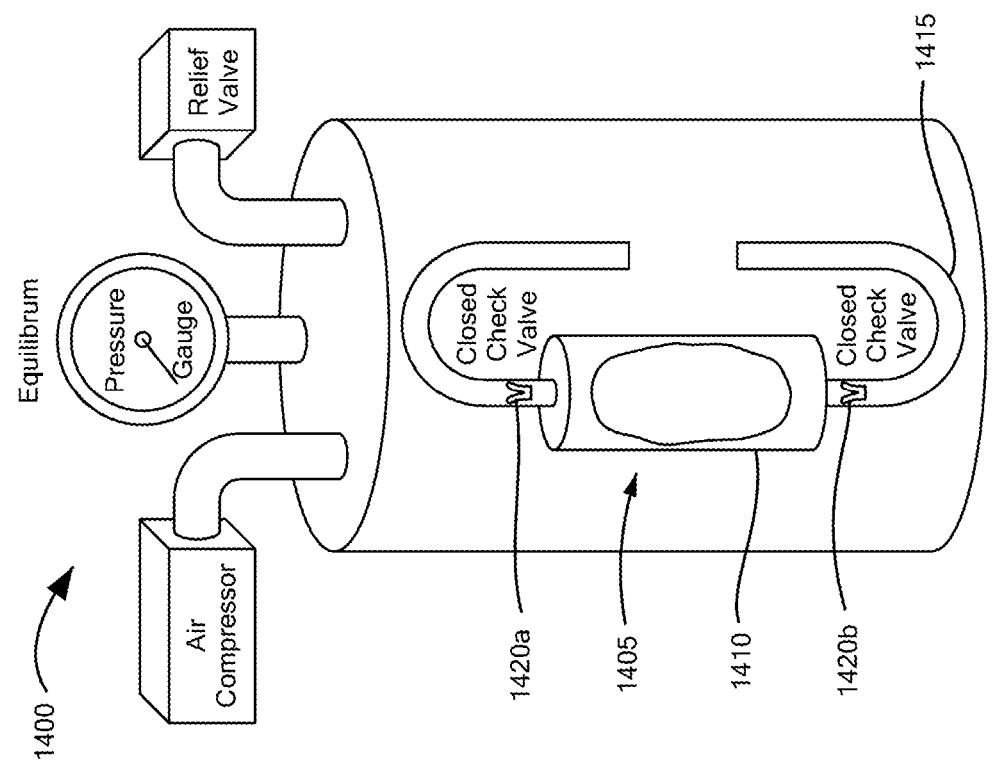
FIG. 14A shows a schematic of a pressurized chamber autopump with a balloon-filled cartridge (at rest), in accordance with some embodiments of the present invention.
Figure 14C:
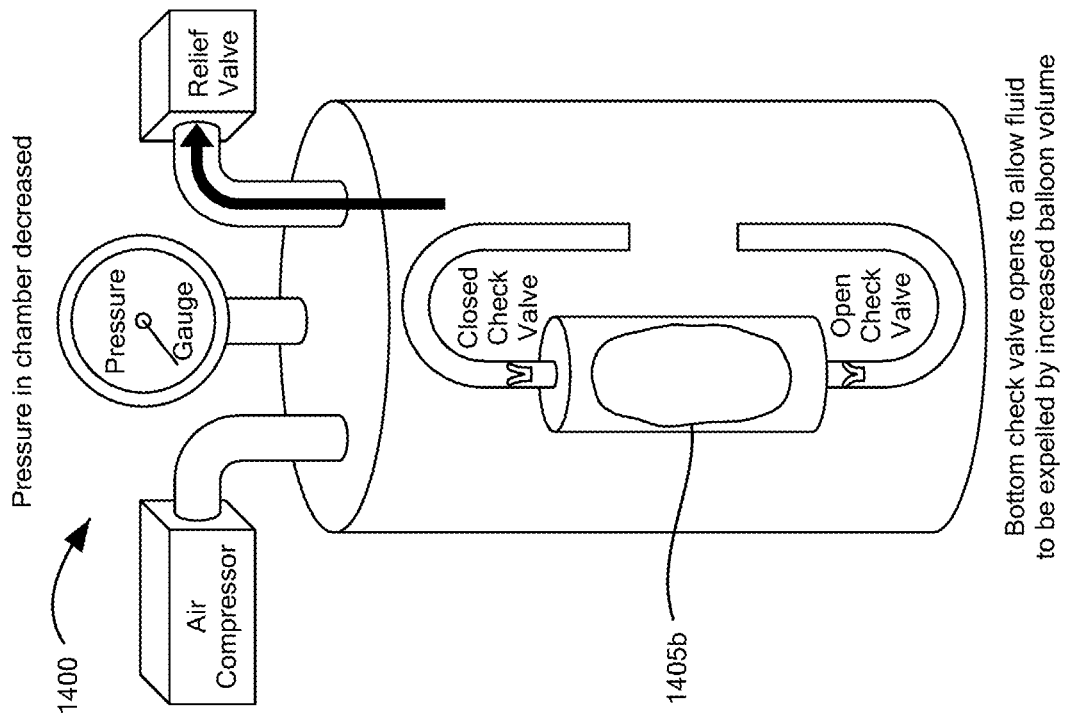
FIG. 14C shows schematic of the pressurized chamber autopump of FIG. 14A with an inflated balloon due to a decrease in surrounding pressure, in accordance with some embodiments of the present invention.

Referring to FIGS. 14A-14C, an embodiment of an autopump 1400 with a balloon 1405 enclosed within the lumen of a cartridge body 1410 is shown. A first check valve 1420*a* may be disposed upstream of the cartridge body 1410 and the balloon 1405 and a second check valve 1420*b* may be disposed downstream of the cartridge body 1410 and balloon 1405. Changes in fluid pressure within the tank cause the balloon 1405 to inflate and distend 1405*b* (FIGS. 14A and 14C) or to collapse or deflate 1405*a* (FIG. 14B). In clinical operation, either end of the autopump 1400 may be disposed at two different locations within the SAS.

In clinical operation, CSF fills the autopump 1400 and further surrounds the device. At lower surrounding CSF pressure, the balloon 1405*b* is distended or inflated (FIG. 14C). At higher surrounding CSF pressure, the balloon 1405*a* is collapsed or deflated (FIG. 14B). As the balloon inflates 1405*b*, the first check valve 1420*a* is closed and the second check valve is opened, causing fluid to be expelled from the cartridge body 1410. As the balloon deflates 1405*a*, the first check valve 1420*a* is opened and the second check valve is closed, causing fluid to be drawn into the cartridge body 1410.

As a result, as fluid pressures in the SAS space alternately increase and decrease, the balloon 1405 will inflate 1405*b* or deflate 1405*a*. This repeated inflation and deflation of the balloon 1405 causes fluid flow unidirectionally past the check valves 1420*a*, 1420*b* thereby implementing a CSF pump 1400 driven by internal pressure fluctuations. In some applications, ameliorating agent may be disposed in the lumen of the cartridge body 1410. Alternatively, in other applications, an ameliorating agent may be disposed within the autopump 1400 or in fluidic series with the autopump 1400.

Figure 9A:
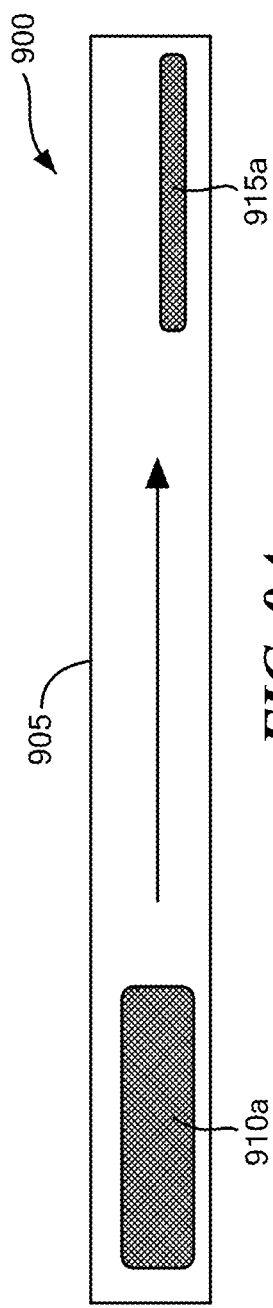
FIG. 9A shows a schematic of a structure for actively pumping fluid from the left bladder towards the right bladder, in accordance with some embodiments of the present invention.
Figure 9B:
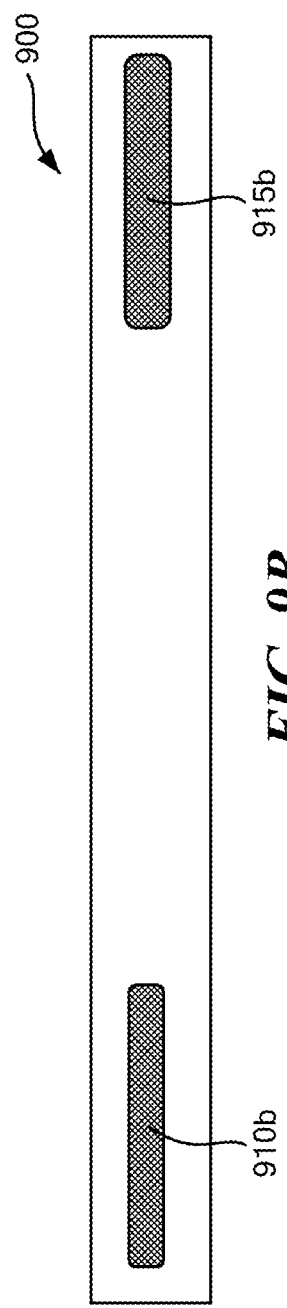
FIG. 9B shows a schematic of the structure of FIG. 9A in an at-rest or intermediate (no-flow) state, in accordance with some embodiments of the present invention.
Figure 9C:
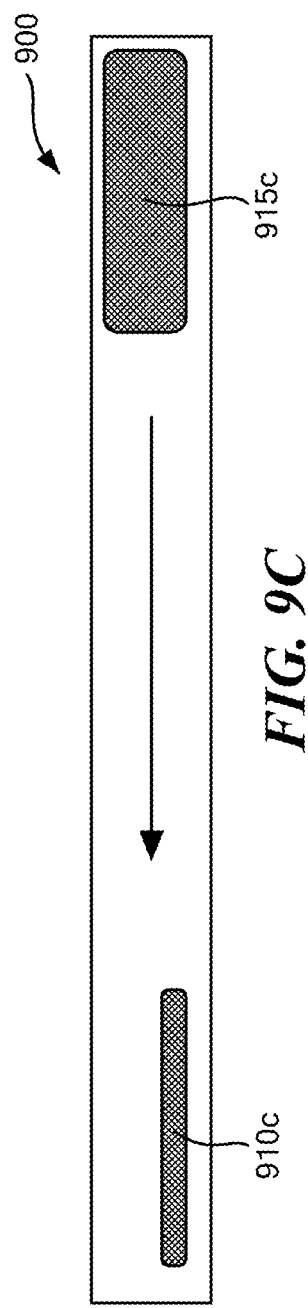
FIG. 9C shows a schematic of the structure of FIG. 9A for actively pumping fluid from the right bladder towards the left bladder, in accordance with some embodiments of the present invention.

Referring to FIGS. 9A through 9C, a completely implantable structure 900 for actively (e.g., hydraulically, pneumatically, and the like) pumping CSF is shown. While the structure will be described for use in combination with the structures 100, 200, 300, 400, 500, 600, 700, 800 previously described, those of ordinary skill in the art can appreciate that an inner surface of the structure 900 could also be decorated with an ameliorating agent, such that as untreated or partially-treated CSF is actively pumped in one direction or another, the untreated or partially-treated CSF may be exposed to a surface area decorated with ameliorating agent, increasing the likelihood that the ameliorating agent will enzymatically digest biomolecules within the CSF.

The principle of operation of the structure 900 uses pulsatile flow actuated hydraulically, pneumatically (e.g., using helium), and so forth. In some embodiments, the structure 900 may include a cartridge 905 containing a pair of bladders 910, 915 disposed at opposing ends of the cartridge 905. Although this embodiment uses a cartridge 905, those skilled in the art can appreciate that a solid cartridge is not necessary and that, in some variations, the pair of bladders 910, 915 may, instead be disposed at two locations with the SAS itself.

From a neutral or at-rest state (FIG. 9B), one of the bladders may be inflated while the other bladder is concurrently deflated. To maintain a no-net volume change condition within the SAS, the inflated bladder may be deflated while the deflated bladder may be inflated. Preferably, the rate and extent of inflation/deflation should not result in pressure or volume changes that exceed or substantially exceed physiological variations, nor should it result in unwanted or excessive turbulence. As previously stated, in some instances, some degree of turbulence is desirable, e.g., to mix treated and untreated/partially-treated CSF.

In order to create a pressure gradient to the right (FIG. 9A), from the neutral or intermediate state, a first bladder 910*b* may be (e.g., hydraulically, pneumatically, and the like) inflated 910*a* while the second bladder 915*b* may be deflated 915*a*. This produces a pressure gradient from the inflated bladder 910*a* to the deflated bladder 915*a*, causing fluid flow from the inflated bladder 910*a* towards the deflated bladder 915*a*. Each of the inflated bladder 910*a* and the deflated bladder 915*a* may then be returned to the at-rest or intermediate state (FIG. 9B), requiring the inflated bladder 910*a* to be deflated to an intermediate pressure 910*b* and the deflated bladder 915*a* to be inflated to an intermediate pressure 915*b*.

In order to create a pressure gradient to the left (FIG. 9C), from the neutral or intermediate state, a second bladder 915*b* may be (e.g., hydraulically, pneumatically, and the like) inflated 915*c* while the first bladder 910*a* may be deflated 910*c*. This produces a pressure gradient from the inflated bladder 915*c* to the deflated bladder 910*c*, causing fluid flow from the inflated bladder 915*c* towards the deflated bladder 910*c*. Each of the inflated bladder 915*c* and the deflated bladder 910*c* may then be returned to the at-rest or intermediate state (FIG. 9B), requiring the inflated bladder 915*c* to be deflated to an intermediate pressure 915*b* and the deflated bladder 910*c* to be inflated to an intermediate pressure 910*b*.

By cycling the structure 900, CSF flow can be actuated and circulated within the SAS in a pulsatile fashion without introducing or extracting fluid in the space. The phase and/or amplitude of the actuated CSF flow may accentuate or diminish the existing pulsatile flow of, for example, the cardiac or respiratory cycles of the subject or, in the alternative, may be independent of both.

In another aspect, in lieu of moving valves, a fixed structure valve, such as are found in piezoelectric microfluidic pumps with a nozzle, may be used. An advantage of valveless pumps is that there are no distinct moving parts to malfunction as there are with pumps with valves. Furthermore, non-linear fluid behavior provides a directionality for the flow.

Control of Flow

In some embodiments, the time-varying flow across the CSF space may be detected (e.g., by sensors) and the flow adjusted to optimize the performance of the system. Exemplary common flow sensors may include a hot wire, a membrane, a Kalman vortex, a Venturi tube, a Pitot tube, a Coriolis flow meter, a Doppler sensor, and so forth.

For example, flow of whatever is being circulated—whether the CSF is being circulated or the structure that is coated or decorated with an ameliorating agent is circulated—may be controlled, for example, to be pulse aware and/or breathing aware. Control parameters may include, for the purpose of illustration rather than limitation: pH, temperature, pressure, local flow rate, mechanical stress, mechanical strain, electrical conductivity, and the like.

The control loop may include an algorithm for an open loop, a feedback loop, a feed forward loop, and so forth. Feedback control may be bang-bang, PID, etc. Advantageously, the system may be analyzed at a system identification level, such that a kernel may be developed. Moreover, in some embodiments, a perturbing actuation (e.g., a pseudorandom binary sequence pressure train) may be imparted to the system for greater control.

In some implementations of the present invention, alarms and safety rails may be established for parameter values. Exemplary alarm and safety rails may include pH (e.g., 7.1-7.7), pressure (e.g., intracerebral pressure (ICP) of 5-15 mm Hg), physiologically-tolerated ranges of temperature (e.g., 34-39 degrees Centigrade), and so forth. In other implementations, a safety bypass for flow may be incorporated into the structure in the event of a clog or a pump failure.

In some embodiments, diagnostic parameters may be gathered in and by the system. For example, these parameters may include physical parameters (e.g., dynamic, kinetic, and chemical parameters) as well as parameters for the purpose of disease diagnosis or disease studies (e.g., using artificial intelligence, big data analyses, and so forth).

Amelioration Systems with a Bulk Flow System

Referring to FIGS. 10A and 10B, embodiments of systems 1000, 1000' for amelioration of CSF that includes a bulk flow system for actuating CSF flow are shown. Actuation may include augmenting the naturally occurring flow of the CSF. Augmentation may include augmenting a phase, a direction, and/or an amplitude of the CSF flow. Advantageously, the bulk flow system may be implanted within the body of the mammalian subject, within or outside of the SAS. In the alternative, substantially all or some portions of the bulk flow system may be implemented ex corpore or outside of the body.

Actuated (e.g., actively or passively pumped) flow may remain entirely within the SAS, may be transported out of the SAS and reintroduced into the SAS, and/or may be transported ex corpore and reintroduced into the SAS. In some implementations, the structure 1005 associated with an ameliorating agent and having its own support catheter 1010 may be completely implanted within the SAS. For the purpose of illustration rather than limitation, the structure 1005 and catheter 1010 are shown as having been implanted within the cerebral SAS 1015 (e.g., a location in the ventricle) rather than in the spinal SAS 1020 (e.g., a location in the lumbar region). Furthermore, for the purpose of illustration rather than limitation, an output port 1025 is created in the cerebral SAS 1015 and an input port 1030 is created in the spinal SAS 1020. In other embodiments, the input port 1030 may be created in the cerebral SAS 1015 and the output port 1025 may be created in the spinal SAS 1020, or both the input port 1030 and output port 1025 may be located in the cerebral SAS 1015 or, alternatively, in the spinal SAS 1020. Each port 1025, 1030 may be implemented using a catheter. In some variations, a single port serving as both an output and an input port may be used (e.g., using a multi-lumen catheter).

A bulk flow system 1050 may provide fluid communication between the ports 1025, 1030. The bulk flow system 1050 may also be completely or partially implanted within the subject. In some applications, the bulk flow system 1050 may include a conduit 1035 through which the CSF flows. CSF flow may remain in vivo or may be transported excorporeally, i.e., outside of the body. One or more sensors 1040 may be provided at discrete locations within the conduit 1035, the bulk flow system 1050, as well as the SAS to provide data signals to a system controller 1045. Typical sensors 1040 may provide data signals of pH, temperature, pressure, flow rate, flow velocity, constituent concentration, UV radiation, IR radiation, turbulence, Raman scattering, dynamic light scattering, and so forth.

While it is permissible that CSF flow through the bulk flow system 1050 may occur at the natural flow rate of the CSF, if active or passive pressure techniques are used, circulation of CSF outside of the SAS may be implemented or augmented using a pump(s) 1055, an actuator(s), a valve(s), and combinations thereof. In some variations, the pump 1055 may include a peristaltic pump, a rotary vane pump, an Archimedes screw, an air bladder, a pneumatic bladder, a hydraulic bladder, a displacement pump, an electromotive pump, a passive pump, an autopump, a valveless pump, a bi-directional pump, and combinations thereof. In other variations, the pump 1055 may be similar in principle to a valveless, synthetic-jet-based micropump, a bladder pump, and the like. In some applications, an algorithm, driver program, or the like executed by the system controller 1045 may control the flow rate and flow velocity of the CSF. The control algorithm may be open loop, feed forward, feedback, and so forth. The system controller 1045 may include an open loop controller, a closed loop controller, a PID controller, a PID threshold controller, a system identification algorithm and so forth.

Referring to FIG. 10B, a bulk flow system 1000' that may be disposed substantially within the SAS 1015' is shown. For the purpose of illustration rather than limitation, the ameliorating agent 1005', which may be placed within a tube or cartridge 1060, has been completely implanted within the cerebral SAS 1015' (e.g., a location in the ventricle). Those skilled in the art can appreciate that, in the alternative, implantation could also occur completely within the spinal SAS (e.g., a location in the lumbar region). In some implementations, flow actuators 1040a, 1040b may be disposed at opposing ends of the cartridge 1060 for the purpose of forcing CSF flow through the cartridge 1060. Although two flow actuators 1040a, 1040b are shown, the flow actuators 1040a, 1040b may also be implemented singly.

A support catheter 1010' and a communication bus 1065 may also be provided. Although the support catheter 1010' and the bus 1065 are shown so as to suggest that they are provided in separate locations, those of ordinary skill in the art can appreciate that a multi-lumen catheter may be used for both the support catheter 1010' and the communication bus 1065 so that both are confined to a single catheter location. In some variations, the communication bus 1065 may be configured to provide electrical and electronic communication between a remote system controller 1045' and the flow actuators 1040*a*, 1040*b*.

Ameliorating Agent Introduced with Circulation of Agent

In some applications, in addition to introducing an enzymatic ameliorating agent into the CSF (e.g., in the SAS), the ameliorating agent also may be circulated through the CSF, rather than remaining stationary or substantially stationary. In some implementations, the ameliorating agent may be completely implanted (e.g., via a catheter) in, for example, the SAS and circulated within the SAS; while, in other implementations, the ameliorating agent may be implanted within the body of the mammalian subject but outside of the SAS, from whence the ameliorating agent may be circulated into and back out of the SAS. As previously mentioned, when an ameliorating agent is introduced without circulation, the CSF may exit the SAS, be circulated past the ameliorating agent, and returned to the SAS.

Figure 11:
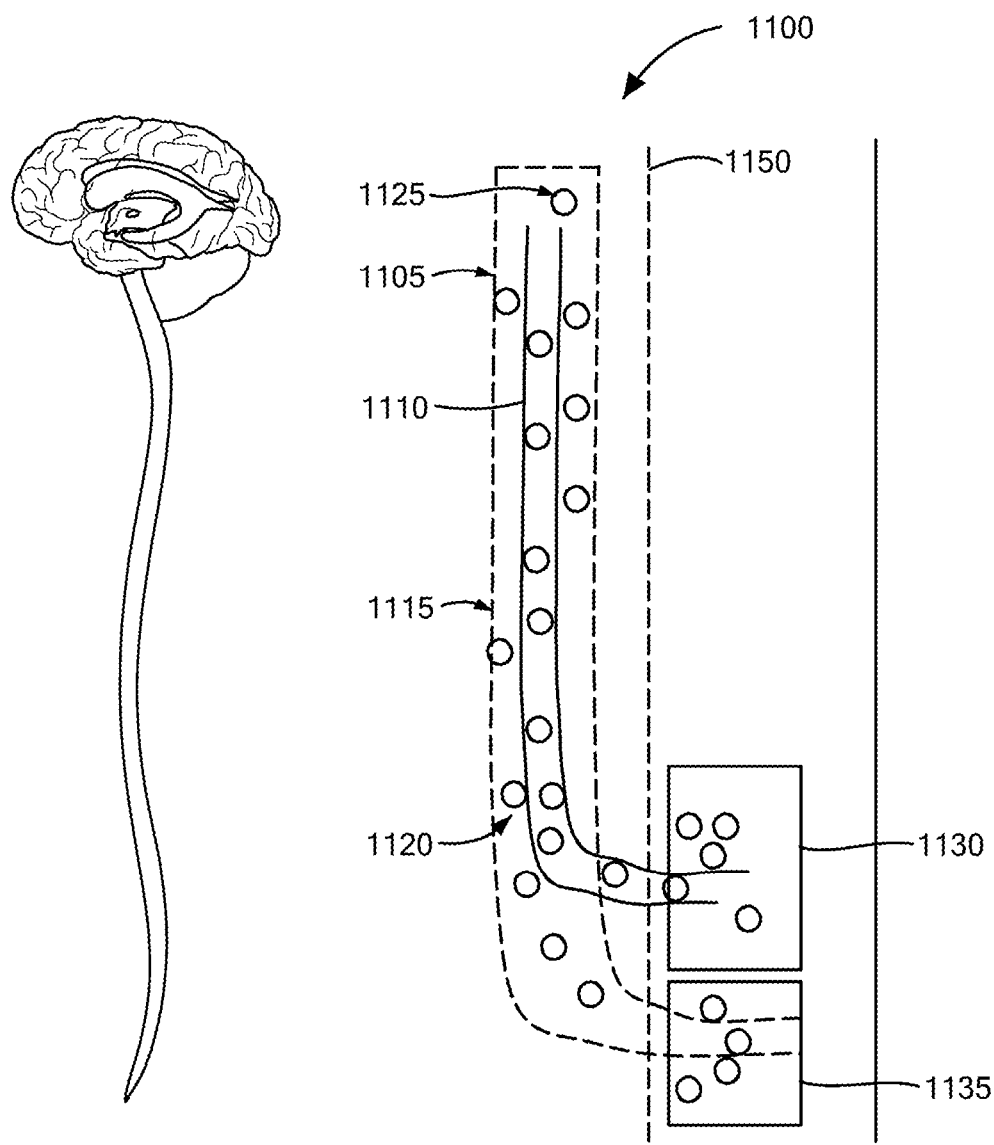
FIG. 11 shows a schematic of a multi-lumen catheter containing a plurality of circulating beads decorated with an ameliorating agent, in accordance with some embodiments of the present invention.

Referring to FIG. 11, in some embodiments, the system or device is implanted below the epidermis 1160, and may include a (e.g., multi-lumen) catheter 1105 that may be completely implanted within the SAS 1150; preferably, in or at a location within the SAS 1150 to allow circulation of a structure or support (e.g., a plurality of superparamagnetic beads) 1125 that have been decorated with an ameliorating agent. A supply reservoir 1130 may be located outside of the SAS, the beads 1125 remaining stationary or substantially stationary, while the CSF may be circulated (e.g., naturally or using active or passive pumping techniques) through the supply reservoir 1130 to increase the exposure and interaction between the CSF and the ameliorating agent-coated beads 1125, as well as the likelihood that the ameliorating agent will enzymatically digest biomolecules within the CSF.

In yet another implementation, an ameliorating agent and the structure or support into which it is injected or to which it is applied (e.g., beads) may be introduced within or substantially within the SAS and circulated through the SAS, in which case, aside from natural fluctuations and flow, the CSF is not intentionally or artificially actuated to motion (e.g., by active or passive pumping). Advantageously, with such an approach, the CSF may remain substantially entirely within the SAS during amelioration, which is desirable.

Although the embodied structure 1100 will be described for an embodiment that contains the beads 1125 within a slurry and circulates the slurry through a multi-lumen catheter 1105 (e.g., mechanically, osmotically, by actively or passively pumping, by gas-actuated bellows, and so forth), those of ordinary skill in the art can appreciate that the magnetic properties of superparamagnetic beads 1125, for example, may, in some applications, assist in actuating circulation of the beads 1125. Indeed, by placing a magnetic field within a receiving reservoir, the superparamagnetic beads 1125 may be magnetically circulated through the SAS 1150 as the resulting magnetic forces attract the beads 1125. In some variations, the multi-lumen catheter 1105 may include an inner lumen 1110 structured and arranged within an outer lumen 1115. For example, a closed-tip, multi-lumen catheter 1105 (e.g., a spinal catheter or a dialysis membrane catheter) may be used. Advantageously, a multi-lumen catheter 1105 requires a single catheter insertion location.

Preferably, the outer lumen 1115 may be porous, with pore sizes that are large enough to permit biomolecules in the CSF (e.g., diameters of about 10-100 nm) to pass through the porous membrane but small enough to contain the beads 1125 (e.g., diameters greater than 1 μm). The diameters of some superparamagnetic beads may range between about 1 and 3 μm (e.g., LODESTAR beads manufactured by AGILENT® Technologies of Santa Clara, CA are about 2.7 μm in diameter); however other beads may have much larger diameters (e.g., 45-165 μm for SEPHAROSE® 4B beads manufactured by SIGMA-ALDRICH® Corporation of St. Louis, MO).

In some implementations, beads 1125 that have been decorated with an ameliorating agent may be introduced (e.g., via an access port in the catheter, using a syringe and needle) into a supply reservoir 1130 that may be completely implanted in the subject inside or preferably outside of the SAS 1150. From the supply reservoir 1130, beads 1125 may then be introduced (e.g., mechanically, osmotically, by magnetic attraction, by actively or passively pumping, by gas-actuated bellows, and so forth) into the inner lumen 1110. Beads 1125 circulate through the inner lumen 1110, down the length of the catheter 1105, then enter a space 1120 between the inner lumen 1110 and the outer lumen 1115 before returning to a receiving reservoir 1135. While flowing in the space 1120 between the inner lumen 1110 and the outer lumen 1115, the circulating beads 1125 encounter untreated or partially-treated CSF. Indeed, untreated or partially-treated CSF containing biomolecules passes freely through the porous outer lumen 1115 into the space 1120 where it encounters the beads 1125, increasing interaction between the CSF and the ameliorating agent-coated beads 1125, as well as the likelihood that the ameliorating agent will enzymatically digest biomolecules within the CSF. Advantageously, during bead 1125 circulation, the CSF may remain within the SAS 1150. CSF may flow naturally into and out of the catheter 1105 or, in some applications, the CSF may be actively or passively pumped while it is in the SAS 1150.

Beads 1125 may circulate side-by-side or coaxially, similar to a continuous countercurrent tangential chromatography configuration. Beads 1125 that have passed through the catheter 1105 and have been exposed to untreated or partially-treated CSF may be removed (e.g., via an egress port, using a syringe and needle) from the receiving reservoir 1135. As previously mentioned in connection with the supply reservoir 1130, the receiving reservoir 1135 may also be completely implanted in the subject inside or preferably outside of the SAS 1150.

An upper value of the required volume of ameliorating agent-coated beads may be estimated by assuming the DPR concentration is less than the concentration of the most prevalent CSF neuroprotein (albumin), which has a concentration of about 69,000 g/mol, which, at $4 \times 10^{-6}$ mol/L, equates to a concentration of about 300 mg/L. In contrast, the concentration of the least prevalent CSF neuroprotein (protein 14-3-3) may be eight to ten orders of magnitude less than that of albumin. The concentration of all neuroproteins in CSF may fall in the range of $10^{-12}$ to $10^{-1}$ g/L.

Assuming an average bead diameter of 100 μm, a concentration of $2 \times 10^{-7}$ mol/L (that of transferrin), a CSF volume of 0.15 L, and a CSF production rate of 0.02 L/hr, the volume of beads required is about 250 mL/week. Hence, there may be about $1.5 \times 10^6$ beads/mL.

In illustrative embodiments, there may be about 1 trillion functional reactive groups per bead and a capacity of about 1 billion affinity-bound proteins per bead; hence, for the assumed concentration, CSF volume, and CSF production rate, there are about $2 \times 10^{19}$ molecules to be captured per year. That number of molecules requires $2 \times 10^{10}$ beads at 250 mL/week (about 12 L/yr.).

In contrast, superparamagnetic beads have an average bead diameter of about 1-3 μm, which is to say about two orders of magnitude less than the diameter used in the above calculation. Where r corresponds to the radius of the bead, the ratio of surface area (A) to volume (V) is given by the equation:

$$A/V = 4\pi r^2/4/3\pi r^3 = 3/r$$

Accordingly, for a 100-fold decrease in the radius (r) of the beads, the ratio will increase by about 100. Accordingly, a few tens of mL of beads are required per week to clean out even an albumin-like concentration of toxins. In contrast, instead of antibodies, if enzymes were used, a much smaller bead volume may be required, since enzymes remain active after an interaction. Indeed, the required volume with an enzyme depends on the activity of the enzyme (e.g., the k_m and k_cat), the flow rate, and the desired CSF component conversion rate.

As an alternative to using and circulating beads through untreated CSF in the SAS, a thread-like structure that has been decorated with an ameliorating agent may be introduced into a supply reservoir 1130 (e.g., on a spool-like structure) and threaded through the inner lumen 1110 and the outer lumen 1115 to the receiving reservoir 1135, where the end of the thread-like structure may be wound (e.g., on another spool-like structure) to draw the thread-like structure decorated with ameliorating agent through the untreated CSF. Drawing the thread-like structure through the catheter 1105 increases the exposure and interaction between the CSF and the ameliorating agent-coated thread-like structure, as well as the likelihood that the ameliorating agent will enzymatically digest biomolecules within the CSF. Multiple threads (e.g., a yarn structure) can be employed and the substrate or agent support.

Focused Flow of CSF without an Ameliorating Agent

In some embodiments, a focused and increased flow, e.g., from a first location in the SAS having a relatively low concentration of toxic biomolecules towards a second location in the SAS having a relatively high concentration of toxic biomolecules, may be desirable. Alternatively, transport from a first location with a high concentration of toxic biomolecules to a second location with a lower concentration of toxic biomolecules may be desirable. For example, focused CSF flow may be desirable and effective within the SAS, outside of the SAS, across the central nervous system, and/or from motor neurons in the middle of the brain or in the middle of the spinal cord. Preferably, flow from the first location to the second location may be increased to provide effective treatment without the need for an ameliorating agent. Instead, the flow itself may be tailored to transport biomolecules from a stagnant location to another location in which natural, physiological degradation of the biomolecules is occurring more effectively. A focused or increased flow may also be desirable to or from regions within the SAS having a higher density of ameliorating agent from or to regions within the SAS having a lower density of ameliorating agent. Augmentation of the natural CSF flow may be possible using an auto bladder pump and the like. CSF flow is characterized not only by a strong pulsatile flow driven by cardiac and respiratory oscillations, but also by a bulk circulation. Spinal CSF oscillatory motion has a watershed at approximately the level of the heart. The CSF must have a bulk flow, since obstruction of the ventricular pathways leads to hydrocephalus. Caudal and cephal movement of the CSF is observed, but the mechanism for this flow is controversial; however, bidirectional bulk motion (about 1 cm/min) of the CSF in the spinal volume may be explained by nonlinear cumulative effects of convective acceleration. CSF from the lumbar region proceeds to the cranial vault in about 15-20 min and the time to refresh the entire CSF volume in the spinal canal volume is a few hours. Additionally, CSF movement in the cranial volume has different flow rates, ranging from 4 mm/s to 5 cm/s, across various portions of the cerebral SAS. As CSF flow is a key component of the subject's natural process of toxic biomolecule clearance, abnormalities in CSF flow may then be a contributor to neurodegenerative pathogenesis. In particular, changes in flushing for specific regions in the SAS may reduce the clearance of toxic compounds and thus be implicated in the etiology of many neurotoxic protein mediated diseases. Thus, in some embodiments of this invention, a flow pattern is devised to advantageously address non-uniform distributions of neurotoxic proteins. Additionally, a system of tailored flow with spatial discrimination may be utilized to deliver medicaments, as well as to clear out toxic components from the CSF.

A focused flow of the CSF may be imparted by means of active and/or passive pumping mechanisms. If a specific flow pattern is desired to address a known disease situation and location, a system of catheters and pumps with various flow rates may be implanted to accomplish the desired focused flow pattern. For instance, if in a diseased state the CSF circulation is impaired in the frontal lobe, active pumps could provide increased flow to that area. This may be beneficial in and of itself, but may also be combined with an amelioration agent. The reasoning for a specific flow pattern to accommodate putative sources and sinks of toxic proteins drive the design of the flow system. Three-dimensional flow fields can be calculated using computational fluid mechanics methods. Example novel circulation paths include cistern to cistern, ventricle to cistern, and cistern to lumbar. In addition, multiple concurrent circulation paths may be implemented. Flow may be actuated by passive pumps, as described elsewhere in this specification, or active pumps, or a combination thereof. Aspects of focused flow are illustrated in FIGS. 12A to 12D.

Figure 12B:
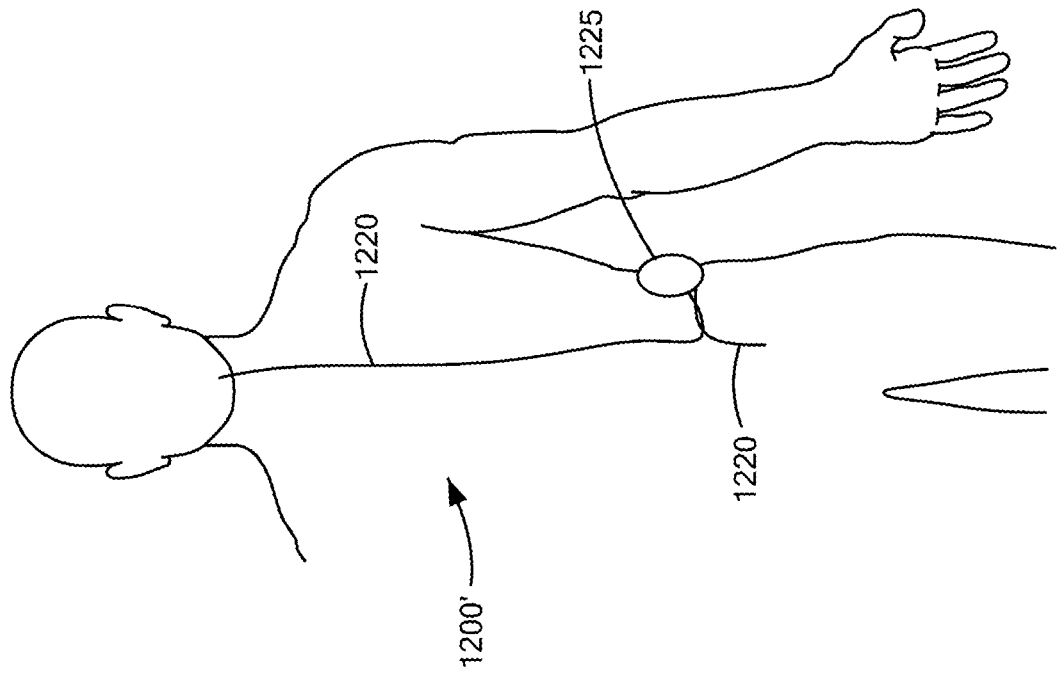
FIG. 12B shows a schematic of a first system for imparting a focused flow from the ventricular region to the lumbar region, in accordance with some embodiments of the present invention.
Figure 12A:
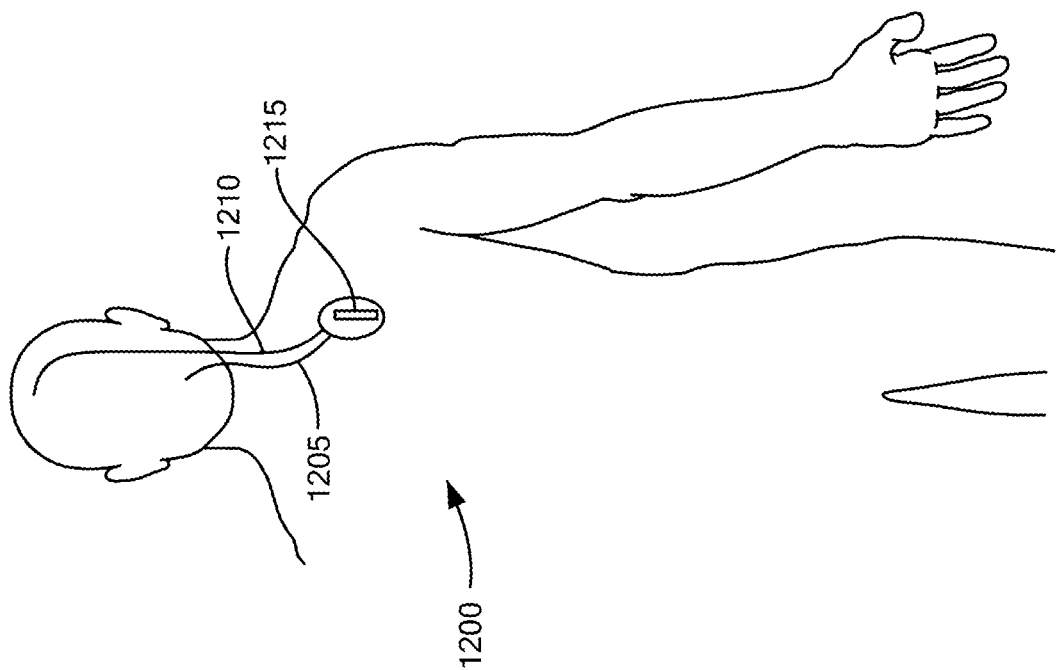
FIG. 12A shows a schematic of a system for imparting a focused flow across the motor cortex, in accordance with some embodiments of the present invention.

For example, FIG. 12A depicts a system that imparts a focused flow across the motor cortex. This system 1200 may include a first catheter 1205 implanted in the cisterna magna, a second catheter 1210 implanted in the cerebral SAS, e.g., above the motor cortex, and a passive (e.g., flow-through) pump 1215 that will expose CSF passing or transported through the pump 1215 to an ameliorating agent. In some implementations, an ameliorating agent is not required. The pump 1215 may be implanted within or outside of the SAS.

FIG. 12B depicts a system 1200' that imparts a focused flow in the spinal canal. The system may include a first catheter 1220*a* implanted in the lumbar-to-cervical region of the spinal SAS in combination with an implanted (e.g., active or passive) pump 1225 that will expose CSF passing or transported through the pump 1225 to an ameliorating agent. Again, in some implementations, an ameliorating agent is not required. The pump 1225 may be implanted outside of the SAS and, in some variations, may include a subcutaneous access port. Advantageously, flow may be rostrocaudal or the reverse. The opposing catheter 1220*b* may continue the CSF flow circuit within the SAS.

Figure 12D:
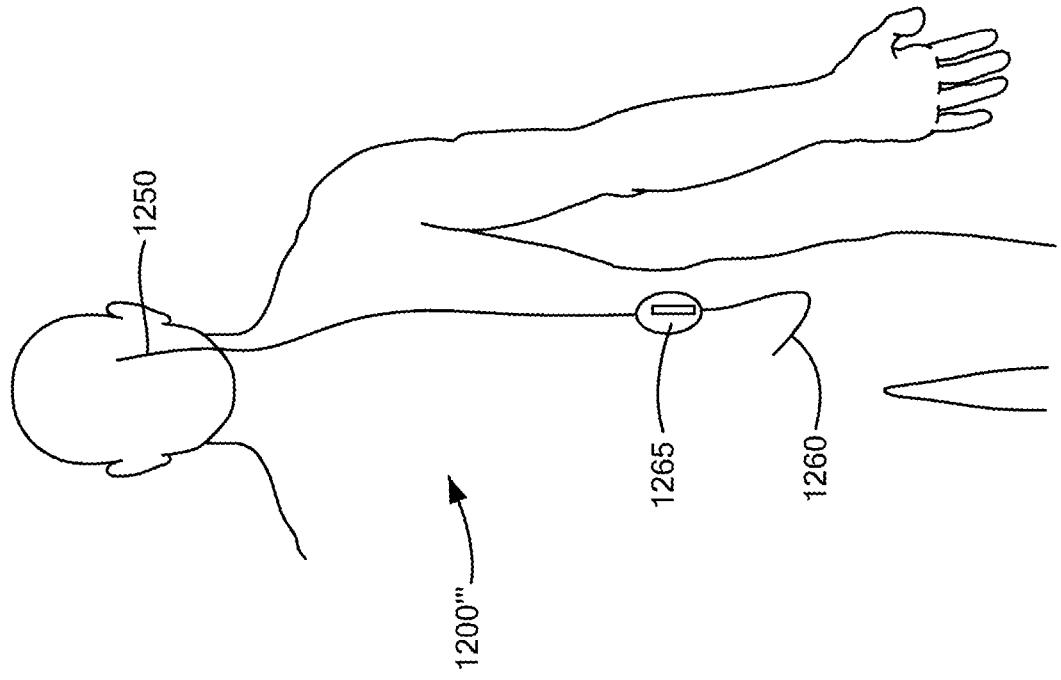
FIG. 12D shows a schematic of a third system for imparting a focused flow from the ventricular region to the lumbar region, in accordance with some embodiments of the present invention.
Figure 12C:
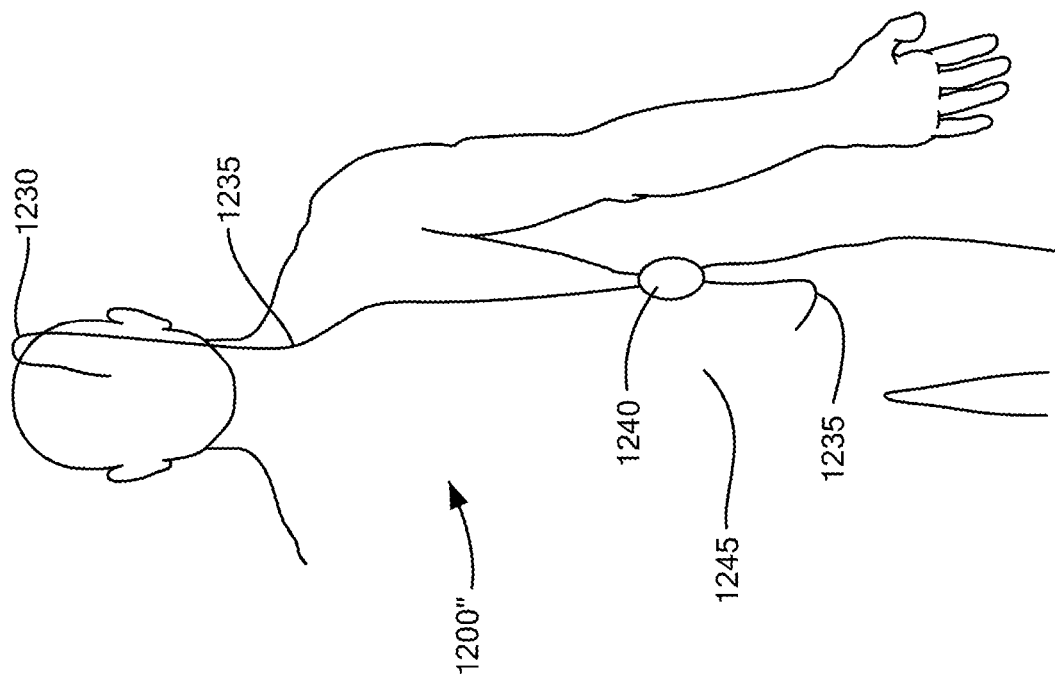
FIG. 12C shows a schematic of a second system for imparting a focused flow from the ventricular region to the lumbar region, in accordance with some embodiments of the present invention.

FIG. 12C depicts a system 1200" that imparts focused flow from the ventricles to the lumbar sac. The system may include a first catheter (e.g., a ventricular catheter) 1230, a (e.g., subcutaneous) catheters 1235*a* and 1235*b*, and a third (e.g., lumbar/intrathecal) catheter 1245 in combination with an implanted (e.g., active or passive) pump 1240 that will expose CSF passing or transported through the pump 1240, i.e., from the second catheter 1235*a* to the third catheter 1245 (or vice versa), to an ameliorating agent. The pump 1240 may be implanted outside of the SAS and, in some variations, may include a subcutaneous access port. Advantageously, flow may be rostrocaudal or the reverse.

FIG. 12D depicts a system 1200' that may include a first catheter (e.g., a ventricular drain) 1250, a lumbar puncture access (e.g., to the spinal volume) 1260, and a waste shunt 1270 (e.g., to the bladder) in combination with an implanted (e.g., active or passive) pump 1265 that exposes CSF passing or transported through the pump 1265 from the first catheter 1250 to the lumbar puncture access 1260 (or vice versa), to an ameliorating agent. The pump 1265 may be implanted within the SAS. Advantageously, flow may be rostrocaudal or the reverse. This system, in an embodiment, may be used with the filtration unit described in FIG. 6. These systems (FIG. 12) utilize the architecture of two common procedures (ventricular shunt to peritoneum for hydrocephalus and a lumbar drug infusion spinal tap).

Filtration Methods

In some implementations, amelioration may be accomplished by means of various filtering techniques, or combinations thereof, including, but not limited to, dead-end (common syringe filters), depth filters, affinity filters, tangential flow filters, countercurrent cascade ultrafilters, and continuous countercurrent tangential chromatography.

In one aspect of the invention, the CSF is ameliorated by a filter or cartridge containing a transforming agent. This treatment may be episodic or continuous. This encourages toxic proteins from the interstitial space to migrate into the blood volume and then into the CSF, or directly into the CSF in the perivascular space. Once toxic proteins are in the CSF, the circulating system removes, degrades, or otherwise makes the proteins non-toxic. The entire system then has the effect of creating a high clearance rate of toxic proteins from the brain parenchyma. In another aspect of certain embodiments of the invention, the CSF may be ameliorated by a filter or cartridge containing a transforming agent thereby encouraging toxic proteins from the interstitial space to migrate directly into the CSF. Once toxic proteins are in the CSF, the circulating system removes, degrades, or otherwise makes non-toxic these proteins. The entire system then has the effect of a high clearance of toxic proteins from the brain parenchyma. In one embodiment of the invention, the filter is of the following type: dead end filter, tangential filter, continuous chromatographic processes, such as periodic countercurrent chromatography (PCC), multicolumn countercurrent solvent gradient purification (MCS GP), and continuous countercurrent tangential chromatography (CCTC), or single-pass tangential flow filtration (SPTFF), or combination thereof.

In an embodiment of the present invention, the filtration method used by the filters is based on one or more of: (1) electromechanical methods including, but not limited to: radiofrequency, electromagnetic, ultraviolet radiation, acoustic wave, piezoelectric, electrostatic, nano-, molecular/biologic force, atomic force, and ultrasonic filtration and ultrafiltration based methods; (2) biochemical/physicochemical properties and/or temperature methods including, but not limited to: size-exclusion, pore flow, solution diffusion, protein size or secondary, tertiary or quaternary structure, diffusion, hydrophobic/hydrophilic, anionic/cationic, high/low binding affinity, chelator, magnetic or nanoparticle-based systems, and various neurochemical filtration systems; and (3) biospecific affinity methods including, but not limited to, specific antibodies, immunotherapy-based, immuno-modulatory, ex-vivo immunotherapy using immobilized antibodies or antibody fragments, nucleic acids, receptors, anti-bacterial, anti-viral, anti-DNA/RNA, protein/amino acid, carbohydrate, enzymes, isomerases, compounds with high-low biospecific binding affinity based systems.

In some embodiments, filtration is based on enzymatic digestion through the use of one or more enzymes that may include: trypsin; elastase; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin, including the cathepsins E, S, B, K, or L1; Tissue Type A; heparinase; granzymes, including granzyme A; meprin alpha; pepsin; endothiapepsin; kallikrein-6; kallikrein-5; and combinations thereof.

In other embodiments, filtration is based on affinity methods relying on cell surface markers of the group: EpCAM, Notch1, HER2+, EGFR, heparanase, and Notch1.

Tangential Fluid Flow

In some embodiments, species of interest such as proteins or other biological moieties are separated from a mixture containing them by subjecting the mixture to tangential-flow filtration (TFF). In some embodiments, the filtration process is employed to retain solutes having a molecular weight between about 1 kDa and about 1000 kDa. As used herein, the term tangential-flow filtration or TFF refers to a process in which the fluid mixture containing the components to be separated by filtration is recirculated at high velocities tangential to the plane of the membrane to increase the mass-transfer coefficient for back diffusion. In such filtrations a pressure differential is applied along the length of the membrane, causing the fluid and filterable solutes to flow through the filter. This filtration is suitably conducted as a batch process as well as a continuous-flow process. For example, the solution may be passed repeatedly over the membrane while that (e.g., CSF) fluid which passes through the filter is continually drawn off into a separate unit or the solution is passed once over the membrane and the (e.g., CSF) fluid passing through the filter is continually processed downstream.

Advantageously, TFF can fractionate by particle size, whereby the filter cake is prevented or inhibited from forming thus permitting long operation times. Furthermore, in some embodiments, alternating tangential flows may be used to dislodge blocks. Of particular advantage, TFF overcomes the polarization concentration effect found in conventional filtration, wherein a polarized layer of solutes acts as an additional filter in series with the original ultrafilter, and provides significant resistance to the filtration of solvent. In TFF, the feed stream is recirculated at high velocities tangential to the plane of the membrane to increase the mass-transfer coefficient for back diffusion. This fluid flow pattern enhances transport of the retained solute away from the membrane surface and back into the bulk of the feed. The fluid flowing in a direction parallel to the filter membrane acts to clean the filter surface continuously and prevents clogging by non-filterable solutes. In another similar embodiment, a rotary filtration device containing an outer and inner cylinder, where the inner cylinder is rotated to create a vortex to obtain high velocity without a change in pressure. In TFF, a pressure differential gradient, called transmembrane pressure (TMP), is applied along the length of the membrane to cause fluid and filterable solutes to flow through the filter.

In one implementation, the high-performance tangential-flow filtration process described herein involves passing the mixture of the species to be separated through one or more filtration membranes in an apparatus or module designed for a type of tangential-flow filtration under certain conditions of TMP and flux. In particular, the TMP is held at a range in the pressure-dependent region of the flux v. TMP curve, namely, at a range that is no greater than the TMP value at the transition point. Thus, the filtration is operated at a flux ranging from about 5% to about 100% of transition point flux. Furthermore, the filtration is carried out such that the TMP is approximately constant with time or decreases throughout the filtration.

The maintenance of the TMP within this pressure-dependent region results in a decrease in retention of molecules with molecular weights lower than the membrane rating and improves the overall selectivity of the system for the species desired to be purified, thereby overcoming the barrier of the concentration polarization layer. As a result, the species of interest are selectively retained by the membrane as the retentate, while the smaller species pass through the membrane as the filtrate, or the species of interest pass through the membrane as the filtrate and the contaminants in the mixture are retained by the membrane. It is noted that the TMP does not increase with filtration time and is not necessarily held constant throughout the filtration. The TMP may be held approximately constant with time or may decrease as the filtration progresses. If the retained species are being concentrated, then it can be preferred to decrease the TMP over the course of the concentration step.

A preferred aspect herein is to utilize more than one membrane having the same pore size, where the membranes are placed so as to be layered parallel to each other, preferably one on top of the other. Preferably the number of membranes for this purpose is two, though additional membrane(s) can be added.

While the TMP need not be maintained substantially constant along the membrane surface, it may be preferred to maintain the TMP substantially constant. Such a condition is generally achieved by creating a pressure gradient on the filtrate side of the membrane. Thus, the filtrate is recycled through the filtrate compartment of the filtration device in the same direction and parallel to the flow of the mixture in the retentate compartment of the device. The inlet and outlet pressures of the recycled material are regulated such that the pressure drop across the filtrate compartment equals the pressure drop across the retentate compartment.

Certain embodiments of the invention also contemplate a multi-stage cascade process, wherein the filtrate from the above process is passed through a filtration membrane having a smaller pore size than the membrane of the first apparatus in a second tangential-flow filtration apparatus. The filtrate from this second filtration may be recycled back to the first apparatus and the process may be repeated. In this cascade process, the second filtration typically is a conventional filtration, wherein the flux is held at a level greater than about 100% of transition point flux; also, generally, the TMP is not held substantially constant along the membrane.

In a more preferred embodiment of the cascade process, both stages involve tangential-flow ultrafiltration, wherein the pore size is from 1 to 1000 kDa. In a three-stage cascade process the filtrate from the second filtration is passed through a filtration membrane having a pore size that is less than that of the second membrane in a third tangential-flow filtration apparatus, the filtrate from this third filtration is recycled back to the first filtration apparatus, and the process is repeated. If only two high-performance filtrations are desired in the cascade process, then the third stage may be conventional, i.e., the flux is held at a level greater than about 100% of transition point flux in this third stage. In a more preferred embodiment of this three-stage cascade process, all three stages involve tangential-flow ultrafiltration.

An exemplary method may be for filtering materials from CSF of a human or animal subject. An exemplary method may include withdrawing a volume of fluid comprising CSF from a CSF-containing space of a subject using a filtration system. An exemplary method may include filtering the volume of fluid into permeate and retentate using a first filter of the filtration system, wherein the first filter comprises a tangential flow filter. An exemplary method may include returning the permeate to the CSF-containing space of the subject. An exemplary method may include filtering the retentate using a second filter of the filtration system. An exemplary method may include returning the filtered retentate to the CSF-containing space of the subject.

In some implementations, the second filter of the filtration system includes a dead-end filter or a depth filter. For example, the method may include filtering the retentate using a plurality of second filters of the filtration system operating in parallel. In some examples, the method further includes, prior to returning the permeate and prior to returning the filtered retentate, combining the permeate and the filtered retentate at a combiner and returning the combined permeate and the filtered retentate to the CSF-containing space of the subject, thereby returning the permeate and returning the filtered retentate. An exemplary system may include a combiner having an intake coupled to the permeate outlet and the outlet of the second filter. The combiner may be configured to combine the fluid filtered by the second filter and the retentate, wherein the combiner has an outlet for returning fluid to a CSF-containing space of the subject. In some variations, the system may further include a third filter having an intake coupled to the second retentate outlet and the combiner is coupled to the permeate outlet, the second permeate outlet, and an outlet of the third filter and configured to combine the retentate, the second retentate of the second filter, and the fluid filtered by the third filter. In some examples, the second filter comprises a plurality of dead-end or depth filters arranged in parallel. In some examples, the plurality of dead-end filters or depth filters in parallel are self-regulating, such that as one of the dead-end filters or depth filters becomes full or clogged, pressure increases resulting in more waste fluid being directed to one or more other dead-end filters or depth filters.

In some applications, the combiner may include a check-valve configured to resist back flow into the second filter. In some variations, the method may further include calculating a waste rate of the filtration system and modifying one or more parameters of the system to maintain a waste rate of less than a threshold. In some examples, the threshold is based on a predicted rate of natural CSF production in the subject. In some examples, the threshold is 0.25 milliliters of CSF per minute. In some examples, the threshold is 0.20 milliliters of CSF per minute. In some examples, the second filter of the filtration system includes a tangential flow filter configured to filter the retentate into a second permeate and a second retentate, and returning the filtered retentate to the CSF-containing space of the subject includes returning the second permeate to the CSF-containing space of the subject. In some examples, the method further includes filtering the second retentate using a third filter of the filtration system and returning the filtered second retentate to the CSF-containing space of the subject.

Substrate Countercurrent Cascade Ultrafiltration

Another embodiment of the present invention is directed to counter flow cascade separation systems. In some implementations, a counter flow cascade separation system may include a series of interconnected stages in which each stage includes a diafilter that accepts a flow stream. The diafilter in each stage is preferentially permeable for a target solute and the diafilter preferentially passes the solute to a permeate flow while preferentially retaining remaining solutes in a retentate flow. Each stage also includes an ultrafilter that accepts from the diafilter the permeate flow, wherein the ultrafilter is selectively permeable to the solvent but not to the remaining solutes contained in the permeate flow. Stages of the system are interconnected so that each stage beyond a first stage accepts an intermixed flow stream formed by combining retentate flow and permeate flow from different stages. The target solute is separated by counter flow cascade through the interconnected series of stages.

In some preferred embodiments, the system may include three interconnected stages. Various preferred systems recycle solvent collected by ultrafilters and route that solvent back to a flow stream. In certain embodiments, these systems include at least one stage that further comprises a macroporous membrane capable of distributing solvent evenly over the diafilter.

Continuous Countercurrent Tangential Chromatography (CCTC)

Another embodiment of the present invention is directed to a system for continuous, single-pass countercurrent tangential chromatography having multiple single-pass modules. A single-pass binding step module is used for binding (e.g., permanently, semi-permanently, or transiently) product from an unpurified product solution with a resin slurry. A single-pass washing step module is used for washing impurities from the resin slurry. A single-pass elution step module for eluting an output of the washing step module is used as purified product solution. A single-pass regeneration step module is used for regenerating the resin slurry. Preferably, the resin slurry flows in a continuous, single-pass through each of the single-pass modules. One or more of the single-pass modules include two or more stages with permeate flow directed countercurrent to resin slurry flow within that single-pass module.

In some applications, the system includes multiple single-pass modules having one or more stages and each stage including interconnected tangential flow filters and static mixers. In a preferred embodiment, the single-pass modules include at least two stages and each stage includes interconnected tangential flow filters and static mixers. The chromatography resin flows through each module in a single pass, while similar operations (e.g., binding, washing, elution, regeneration, and equilibration) to a regular chromatographic process are performed on the resin. The buffers for these operations are pumped into the module in a countercurrent direction to the flow of resin; permeate solutions from later stages are recycled back into previous stages. This creates concentration gradients in the permeate solutions of the tangential flow filters in the countercurrent direction to resin flow.

Ex Corpore System and Method for Amelioration

Figure 15A:
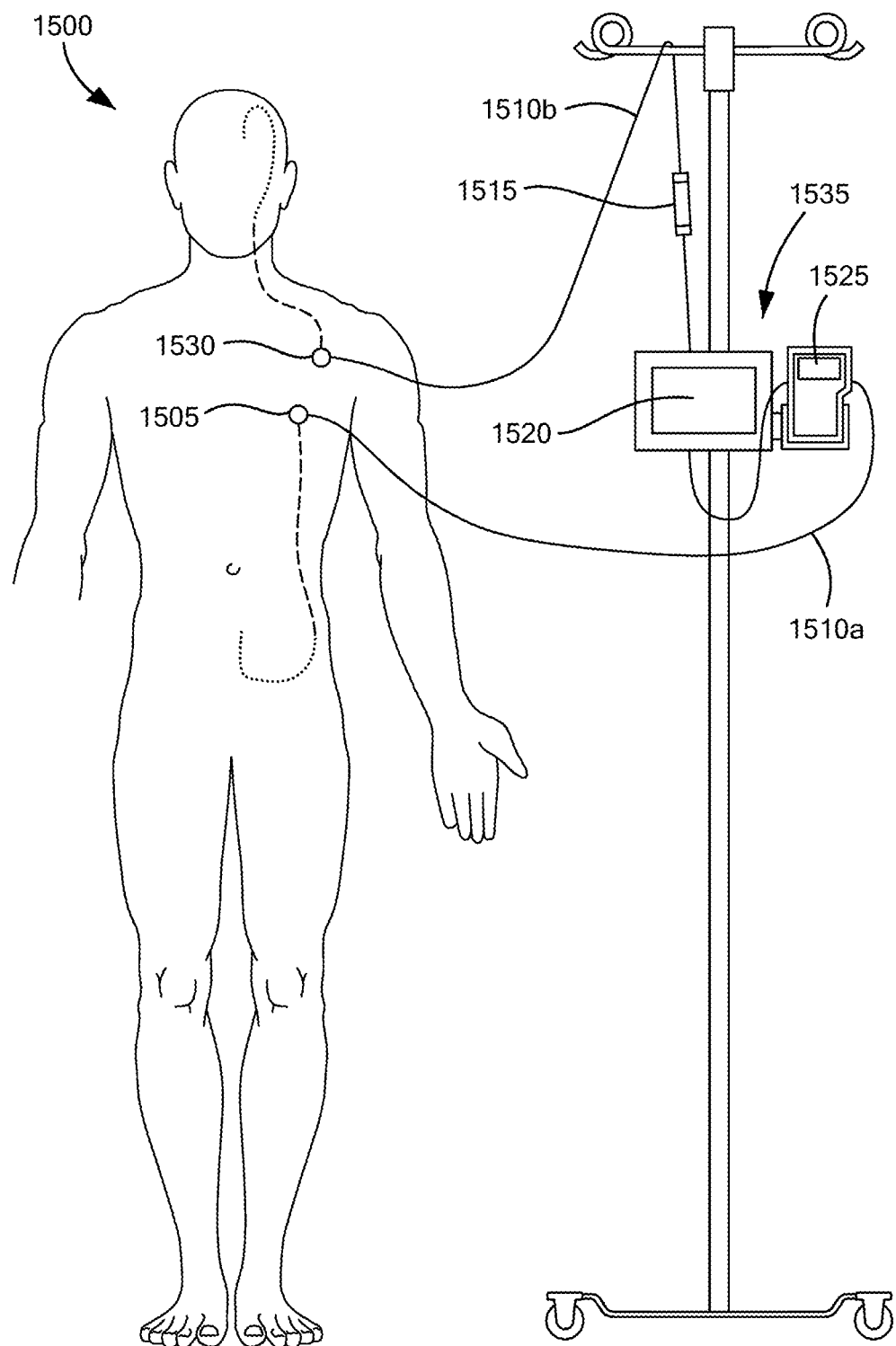
FIG. 15A shows a schematic of an exemplary system for ex corpore amelioration of a fluid (e.g., CSF) in accordance with some embodiments of the present invention.
Figure 15B:
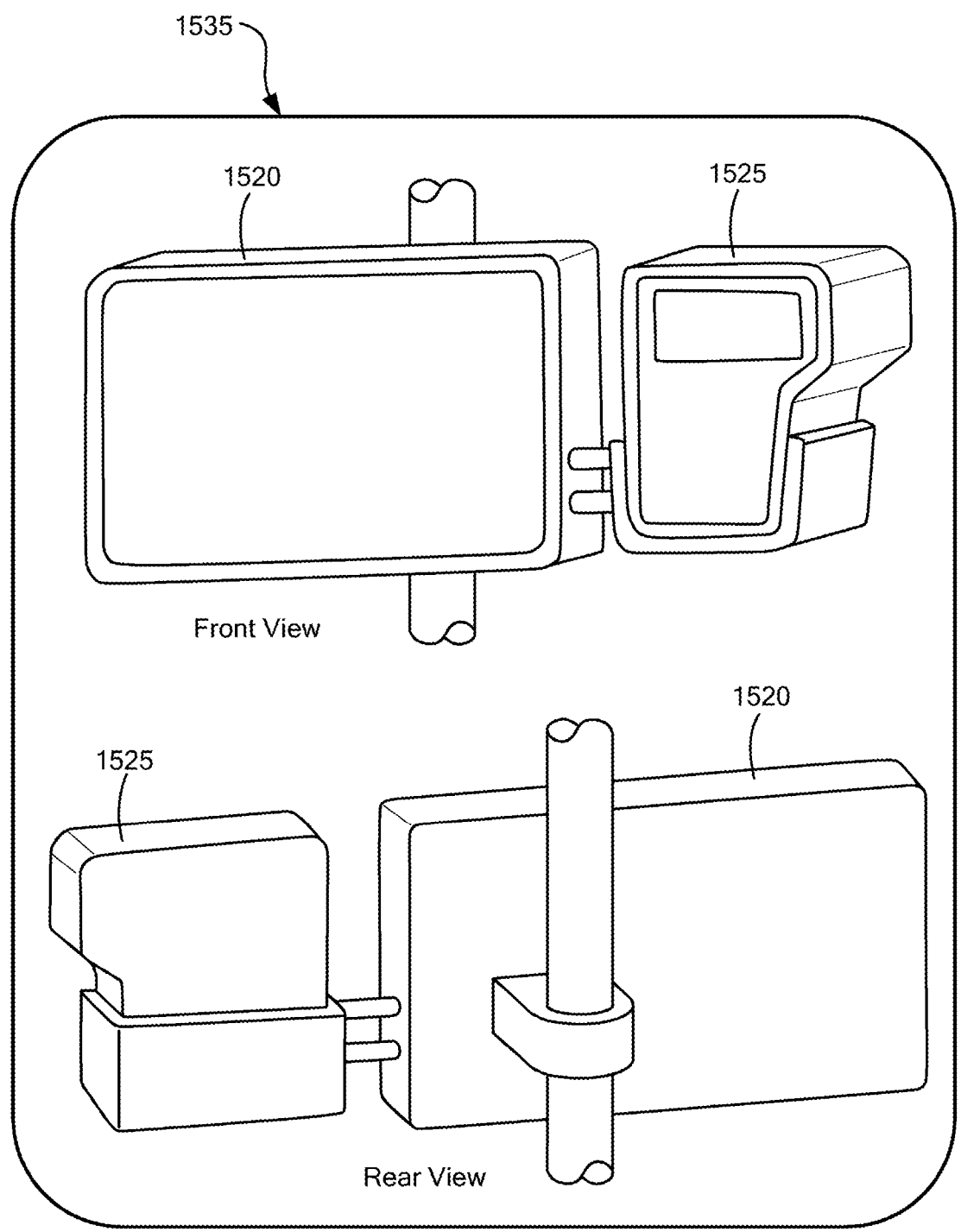
FIG. 15B shows schematic of front and rear views of a control system and a pump system for the system shown in FIG. 15A, in accordance with some embodiments of the present invention.
Figure 15C:
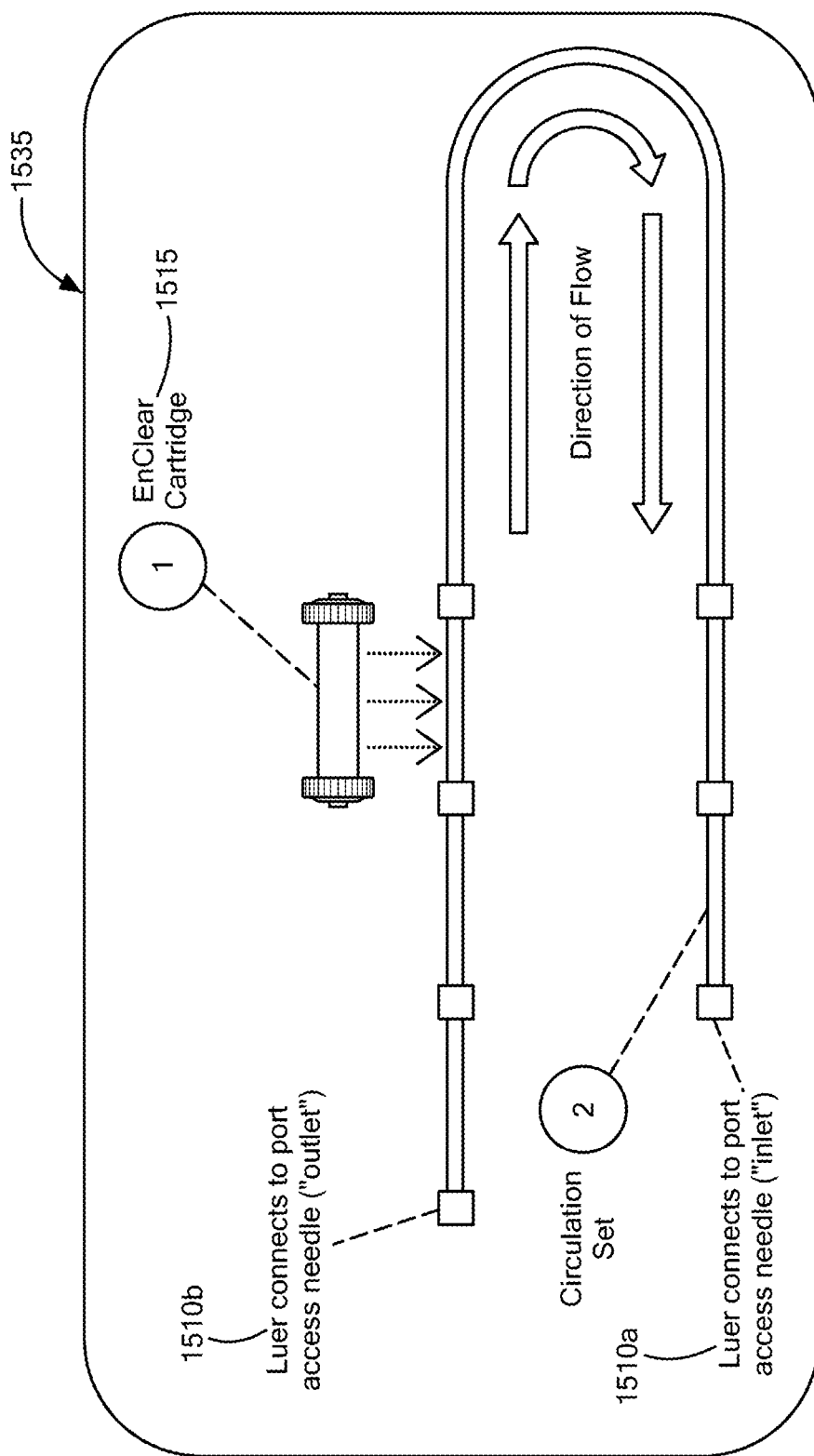
FIG. 15C shows a schematic view of a fluid direction system for the system shown in FIG. 15A, in accordance with some embodiments of the present invention.

An ex corpore system for amelioration of CSF removed from a mammalian subject is shown in FIGS. 15A through 15C. More specifically, FIGS. 15A through 15C show a partially-implantable system 1500 that includes a cartridge 1515 and a fluid communication system 1535, disposed outside of the body, that may be used to remove substances, such as (e.g., toxic) proteins, cells, and the like, that have negative impact on and are symptomatic of a disease. Applications include, for the purpose of illustration rather than limitation: neurodegenerative diseases, stroke, and immune mediated diseases, such as lupus.

Figure 16:
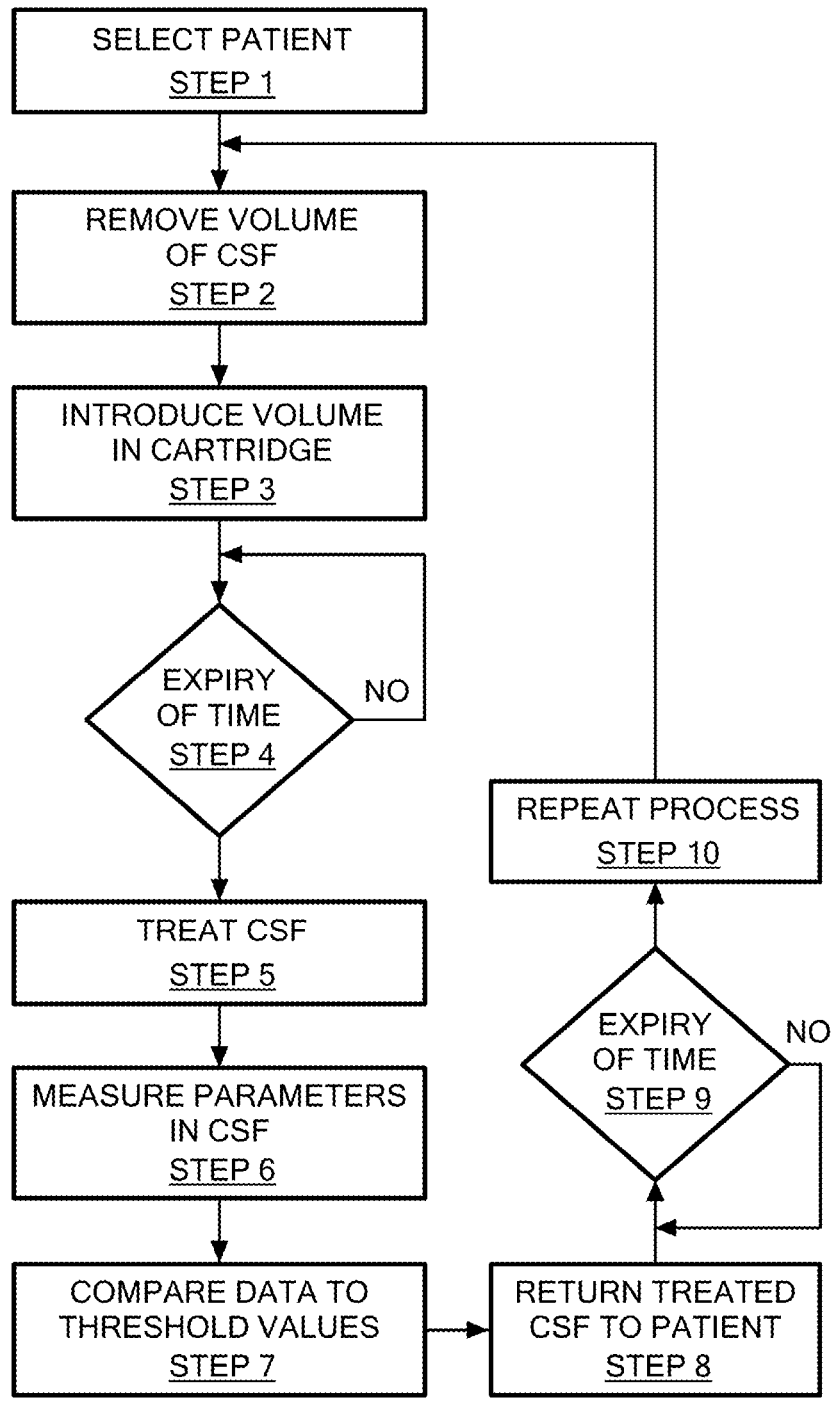
FIG. 16 shows a flow chart of a method for ex corpore amelioration of CSF using the system shown in FIG. 15A, in accordance with some embodiments of the present invention.

Referring to FIG. 16, in conjunction with FIGS. 15A through 15C, a method of amelioration of the symptoms of a (e.g., neurological or non-neurological) disease is shown. In a first step, a medical professional(s) selects a patient for treatment who displays one or more of the symptoms of a particular disease (STEP 1). For the purpose of illustration, rather than limitation, these diseases may include: amyotrophic lateral sclerosis (ALS), Frontotemporal Degeneration (FTD), Progressive supranuclear palsy (PSP), Alzheimer disease (AD), Parkinson disease (PD), Huntington disease (HD), Guillain-Barré Syndrome (GBS), meningitis, cerebral vasospasm, a drug overdose, and so forth.

At a first location 1505 in the mammalian subject, an outlet port access needle (e.g., a lumbar catheter) may be introduced (e.g. via a subcutaneous access port) into the SAS space of the subject (e.g., in a lumbar CSF space) from which a volume of CSF may be removed (STEP 2). In some implementations, the volume of CSF removed may range from between about 1 mL to about 200 mL and the flow rate of removal may range from between about 0.1 mL/min to about 100 mL/min. The removal flow rate may be controlled by a pumping device 1525, such as any of those active or passive pumps described herein. The removed volume of CSF may be transported, e.g., via a conduit 1510a, to and introduced into a cartridge 1515 (STEP 3) for treatment in the presence of an ameliorating agent, ameliorating technique, and/or ameliorating process. In some variations, treatment (STEP 5) may begin immediately, while, in other variations, treatment may begin after expiry of a predetermined period of time (STEP 4). The predetermined period or time, or first waiting period, may range from short (measured in milliseconds to minutes) to long (measured in one or more hours) to accommodate pump recycle times, cartridge pressure buildup, and/or physiological re-equilibrium times. In some variations, the process may be continuous or substantially continuous.

Once the removed volume of CSF is introduced into the cartridge 1515, the removed volume of CSF may be treated (STEP 5) (e.g., to remove, neutralize, digest convert, sequester, and the like) to ameliorate the biomolecules or toxic proteins (e.g., tau, cis ptau Abeta, TDP-43, SOD1, DPRs, neurofilament, alphasynuclein, and the like) contained or believed to be contained in the removed volume of CSF. Preferably, the cartridge 1515 contains an ameliorating agent for treating the biomolecules or toxic proteins. The ameliorating agent may be decorated on, deposited on, attached to, adhered to, and the like to the inner surfaces of the cartridge 1515; may be decorated on, deposited on, attached to, adhered to, and the like to beads (e.g., porous, chromatography resin beads, and the like) that are disposed within the cartridge 1515; and so forth. As previously described, in some applications, the ameliorating agent may include pin1, living cells, exosomes, an enzyme (e.g., trypsin; elastase; cathepsin; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin E, S, B, K, L1; Tissue Type A; heparinase; granzymes, including granzyme A; meprin alpha; pepsin; endothiapepsin; kallikrein-6; kallikrein-5; and combinations thereof) for treating (e.g., by enzymatic digestion) for example, biomolecules or toxic proteins, such as tau, cis ptau Abeta, TDP-43, SOD1, DPRs, neurofilament, alphasynuclein, and the like.

Once the removed volume of CSF has been treated within the cartridge 1515 (STEP 5), the treated volume of CSF may be returned, via a return conduit 1510b, to the mammalian subject (STEP 8). More specifically, the treated volume of CSF may be returned to the mammalian subject (STEP 8) at a second location 1530, for example, using an inlet port access needle (e.g., a cervical catheter, a ventricular catheter, and the like) that introduces the treated volume of CSF (e.g. via a subcutaneous access port) into the SAS space of the subject (e.g., into the cervical CSF space, into the ventricular CSF space of the subject, and so forth). Preferably, the pumping device 1525 is further structured and arranged to return the treated volume of CSF to the mammalian subject (STEP 8) at the same or substantially the same flow rate as the rate of the removed volume of CSF. Treating the removed volume of CSF may include a dual flow capability, such that, after removing a volume of CSF from the patient (STEP 2) and before returning the treated CSF to the patient (STEP 8), the volume of CSF may be introduced and reintroduced bi-directionally or repeatedly sequentially into the cartridge 1515 to increase the residence time and exposure of the removed CSF to the ameliorating agent in the cartridge 1515. Although the various steps of the method are described sequentially, those of ordinary skill in the art can appreciate that these steps may and likely will occur concurrently or partially concurrently when the method is being practiced as the various volumes of CSF pass through the various stages of the embodied method.

The systems and methods described herein are optionally bidirectional, such that at the first location 1505, an outlet port access needle (e.g., cervical catheter, a ventricular catheter, and the like) may be introduced (e.g. via a subcutaneous access port) into the SAS space of the subject (e.g., into the cervical CSF space, into the ventricular CSF space of the subject, and so forth) from which a volume of CSF may be removed (STEP 2). Once the removed volume of CSF has been treated within the cartridge 1515 (STEP 5), the treated volume of CSF may be returned, via a return conduit 1510b, to the mammalian subject (STEP 8) at a second location 1530, for example, using an inlet port access needle (e.g., a lumbar catheter) that introduces the treated volume of CSF (e.g. via a subcutaneous access port) into the SAS space of the subject (e.g., in a lumbar CSF space).

In some variations, at least one sensing device may be disposed in the return conduit 1510b, after the cartridge 1515, to capture a measurable characteristic of the treated volume of CSF (STEP 6) as the treated volume of CSF is being returned to the mammalian subject (STEP 8). Optionally, sensing device(s) may be disposed in the upstream conduit 1510a. Exemplary characteristics of the treated volume may be captured using sensing devices that are configured to measure one or more of: volume, pressure, temperature, pH, flow rate, and the like. Advantageously, data from the sensing device(s) may be transmitted to a control system 1520 (e.g., a microprocessor) that, inter alia, receives and handles the data and, moreover, compares the sensed data provided by the sensing device(s) to predetermined threshold values that are stored in a memory contained in the control system 1520 (STEP 7). Due to concerns about the adverse effects of a treated volume of CSF being returned to the SAS space at, for example, a physiologically-unacceptable flow rate, pressure, temperature, volume, and so forth (i.e., at a rate, pressure, temperature, volume, and so forth that might cause harm or discomfort to the mammalian subject), the control system's 1520 comparison of existing conditions to the predetermined threshold values, may be used, by the control system 1520, to control, using a communication subsystem, the flow of the treated volume of CSF, so as to ensure that the operational parameters of the returned CSF are physiologically acceptable. These comparisons and the sensed data may be used to update a parameter of a set of operation parameters. For example, if the sensor detects a rise in pressure, the pump rate may be reduced or, in some instances, reversed.

Once a treated volume of CSF has been returned to the SAS space of the mammalian subject (STEP 8), the method may be repeated (STEP 10) until amelioration goals are obtained. In some implementations, a second period of time must pass (STEP 9) before repeating the method (STEP 10). The second period of time, or the second waiting period, may be short (measured in milliseconds to minutes), long (measured in one or more hours), or a combination of variable lengths. For example, a physician may require a treatment regimen that includes substantially continuous CSF filtration for nine hours, repeating the treatment regimen once a day for five consecutive or spaced days or more, observing other clinical measures of the disease, and repeating the once a day treatment for about three months, more or less.

Optionally, in addition to the tubing for the conduit 1510a and return conduit 1510b, the CSF direction or circulation system 1535 may include access ports for injecting drugs or introducing a bolus into the tubing and/or for removing waste from the untreated or treated volume of CSF. The CSF direction or circulation system 1535 may also include one or more of: T-valves, shutoff valves, anti-backflow valves, and the like for controlling the flow of the CSF through the conduits. The various valves can be used, for example, to prevent or minimize unintended backward fluid flow and to permit one or more of: priming, flushing, gas purging, removal of occlusions, maintenance operations (e.g., component replacement), and so forth. The CSF direction or circulation system 1535 may also include one or more filtration systems positioned before or after the cartridge 1515 as a primary or additional treatment method. Exemplary filtration systems may include, for the purpose of illustration rather than limitation: size filtration, ionic filtration, tangential flow filtration, counter-current tangential flow filtration, ultrafiltration, notch filtration, series filtration, cascade filtration, and combinations thereof. As the untreated volume of removed CSF or the treated volume of CSF pass through the CSF direction or circulation system 1535, the flowing CSF may flow past stations at which the CSF may also be subjected to electromagnetic fields, ultraviolet (UV) radiation, heat, bioaffinity interactions (with or without the use of antibodies), and the like. Optionally, bioaffinity interactions may appear with or may be used in combination with manipulation agents (e.g., beads, nanoparticles, optical tweezers, and the like).

Cartridge

Figure 18:
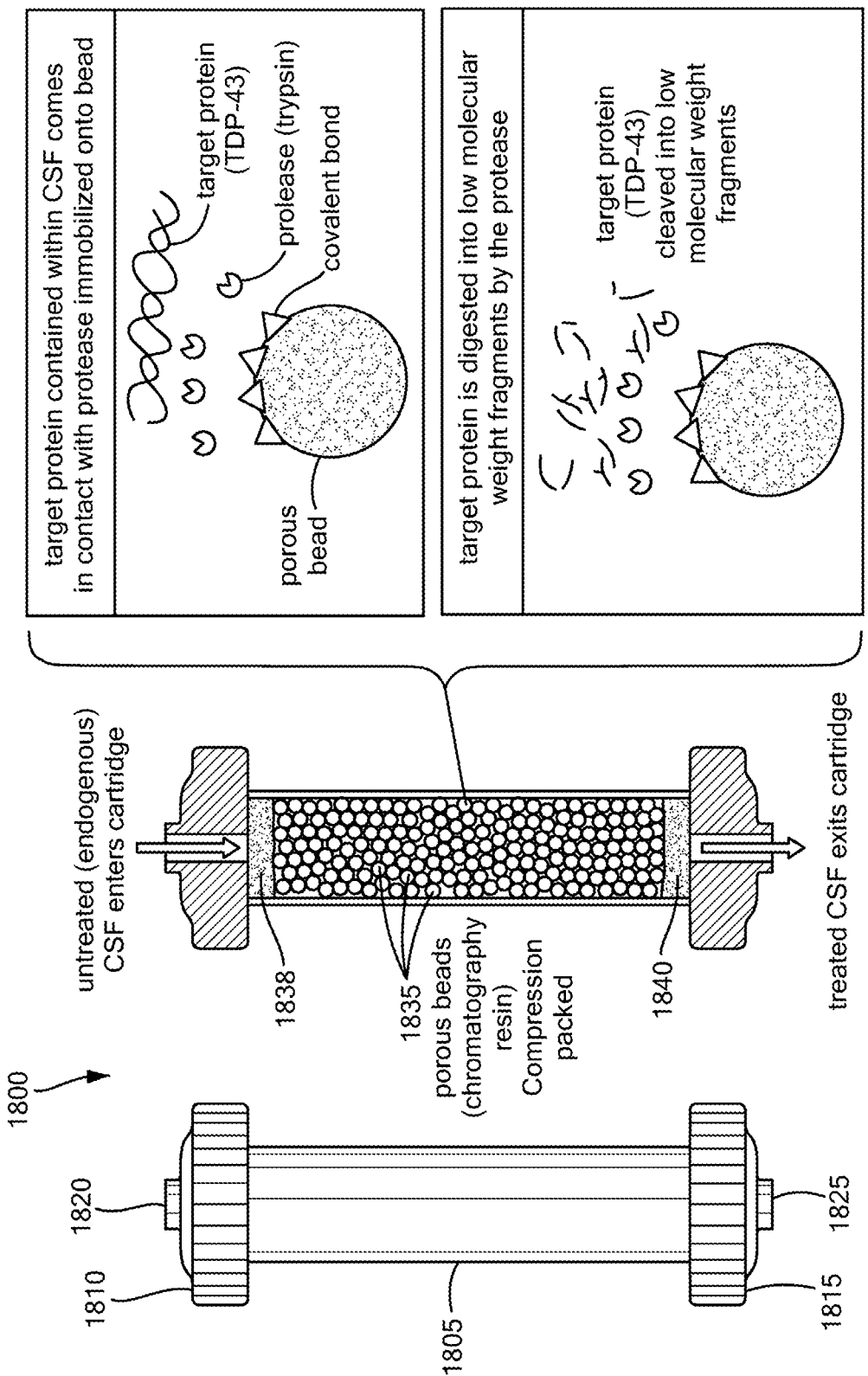
FIG. 18 shows a schematic of a cartridge, in accordance with some embodiments of the present invention.

Referring to FIG. 18, one embodiment of a cartridge 1800 for use in treating CSF removed from a mammalian subject is shown. In some embodiments, the cartridge 1800 can be a commercially-available chromatography column 1805 such as the OPUS® MiniChrom (11.3 mm×5 mL, REP-001) manufactured by Repligen Corporation of Waltham, Massachusetts. The cartridge 1800 may have a first end to which a first cap 1810 is removably attachable (e.g., by friction fit, screw on, snap on, and so forth), as well as a second end to which a second cap 1815 is removably attachable (e.g., by friction fit, screw on, snap on, and so forth). Each of the caps

1810, 1815 may include an opening through which a first (e.g., upstream) conduit 1820 or a second (e.g., downstream) conduit 1825 may be inserted to provide fluidic communication to and through the cartridge 1800. In some embodiments, the inner plenum space 1830 of the cartridge 1800 may be filled with a plurality of (e.g., porous, chromatography resin) beads 1835 that have been compression packed. To prevent constituents from entering or escaping from the cartridge 1800, a first filter membrane 1838 may be disposed at the first end of the cartridge 1800 and a second filter membrane 1840 may be disposed at the second end of the cartridge 1800. In some applications, the ameliorating agent has been decorated on the beads 1835.

In some applications, the cartridge 1800 may be compression packed with a chromatography resin (e.g., agarose, epoxy methacrylate, amino resin, and the like) that has a protease covalently bonded (i.e. immobilized) to the three-dimensional resin matrix. The resin is a porous structure having a particle size commonly ranging between 75-300 micrometers and, depending on the specific grade, a pore size commonly ranging between 300-1800 Å.

In order to preserve proper function and sterility of the cartridge 1800, aspects of the cartridge manufacturing process should be carefully managed. For example, the activity of the cartridge 1800 or the availability of active sites of the protease to digest target proteins and inhibition of microbial growth within the resin matrix is important. In some implementations, particle size may be about 1-50 micrometers and pore size may be about 8-12 nanometers. In some applications, a narrow distribution of pore size may be desirable, while in other applications, a broad distribution of pore size may be desirable. In still other applications, a multimodal distribution of pore size may be desirable.

In the case of cartridge activity, it is common to fill the column 1805 with a buffer solution for preservation. Buffers are intended to inhibit autocatalysis and prevent the reduction of active sites on the available surface area of the resin matrix. One example of a buffer solution that has been successfully implemented is 10 mM HCl with 20 mM $CaCl_2$) at pH 2 and stored at 4° C. In some variations, buffers may include: PBS 1× may be used as an immobilization buffer, Ethanolamine 1M, pH 7.5 may be used as a blocking buffer, PBS 1×/0.05% ProClin 300 may be used as a storage buffer, and HBSS may be used as a digestion buffer.

In the case of inhibiting microbial growth, it is common to assembly similar components in an environment that is either clean (e.g., in compliance with ISO 14644-1 Cleanroom Standards) or sterile in order to avoid the introduction of microorganisms, followed by a sterilization process utilizing proven approaches such as gamma irradiation, x-ray, UV, electron beam, ethylene oxide, steam, or combinations thereof.

Another variable that may be controlled to inhibit the growth of microorganisms and/or to influence the inhibition of autodegradation of enzymes is the pH level of the solution. Solutions with a pH of 2 may be successfully implemented; however, solutions with a pH in the range of about 3 to about 7.5 pH are possible.

Yet another variable that can be controlled to inhibit the growth of microorganisms is temperature. Chromatography columns are commonly stored at temperatures in the range of 2-8° C., which range has been proven to be effective and widely accepted. Storage may be kept within this temperature range until the cartridge is ready to use.

Manufacture of the cartridge 1800 may occur in a near-ambient temperature cleanroom (e.g., ISO Class 8) environment. This manufacturing process includes packing the resin (with immobilized enzyme) onto the chromatography column 1805 and packaging in a double-layer film polypropylene package. The packaged cartridge 1800 may then be prepared for the sterilization process, which may be gamma sterilization. Gamma sterilization has been identified as the exemplary sterilization technique, which is primarily driven by the presence of a liquid buffer. Techniques such as ethylene oxide and steam may be unlikely to penetrate and permeate the liquid adequately to achieve the necessary level of sterility. Ideally, the cartridge 1800 should be refrigerated as soon as it is produced and kept refrigerated during transport to and from the sterilization. Once the cartridge is through the sterilization process, it can be shipped (e.g., after refrigeration) to a final destination, such as a contract manufacturer or inventory holding area, where it can be stored at 2-8° C.

In use, the cartridge 1800 may be retrieved from its temperature-controlled environment and staged at the point-of-care (POC). At the POC, the cartridge 1800 may be removed from its sterile packaging and subjected to a flushing protocol to wash away the buffer solutions, as well as any potentially unwanted residual components, such as unbound enzyme. Flushing or washing mitigates the risk of residual/detached trypsin or other amelioration agent from entering the body when treated CSF is returned to the subject.

The flushing protocol may require a plurality of flushing procedures using various volumes of a flushing solution. Advantageously, the flushing protocol may ensure that any potential residual amelioration agent or enzyme (e.g., trypsin) that may elute from the cartridge 1800 is flushed out. For example, in some implementations, the cartridge 1800 may be flushed with approximately one column volume (i.e., 1.0 CV) of a solution (e.g. phosphate-buffered saline (PBS)). PBS has been shown to eliminate trace amounts of residual enzyme. A higher volume of solution could be used for added assurance. For example, the cartridge 1800 could be flushed with 5-6 CVs (or 25-30 Ml) for a 5 mL column 1805. In some variations, for more consistent flow through the porous chromatography resin, the temperature of the cartridge 1800 may be raised above ambient temperatures. An exemplary flushing protocol may include flushing with 6 CVs (or 30 mL) of PBS followed by a second flushing 6 CV or 30 mL of Hanks' Balanced Salt solution (HBSS).

In one embodiment, the system may be used to deliver substances by means of cells or exosomes that have been deposited in or decorated on the cartridges 1515. The cells or biomolecules used for amelioration may be selected based on the beneficial molecules that are secreted (e.g., trophic factors, anti-inflammatory molecules, and the like) or genetically engineered to produce and release beneficial biomolecules (e.g. having trophic factors, anti-inflammatory factors, and the like). Thus, therapeutic material may be delivered (e.g. by way of circulation of CSF) back into the mammalian subject (e.g., the brain, the spinal cord, and so forth) using these beneficial molecules. As long as there is a barrier against inflammatory mediators and immune system cells on the cartridge 1515, the ex-vivo nature of the application cartridge 1515 also may prevent or hinder a subject's immune system from attacking the foreign cells, if the cells were otherwise implanted directly into the body.

More specifically, the embodied system 1500, in some applications, employs exosomes and or living cells in the amelioration of CSF removed from a mammalian subject. Exosomes are vesicles containing, for example, DNA, RNA, proteins, lipids, and miRNAs. Exosomes are typically found in the extracellular space and have a variety of functions in the body. For example, exosomes are known to transfer between cells, providing a method for cell-to-cell communication. Exosomes have also demonstrated protective activity thought to be via the release of proteins from the exosomes that are neuroprotective. Exosomes isolated from relevant cells that are known to have protective properties are loaded into the cartridge 1515 and the secreted molecules circulate to the brain and spinal cord.

In some implementations, the cartridge 1515 in the system may be loaded with exosomes or cells, so that, when the CSF is removed from the subject, the CSF circulates through the cartridge 1515 packed with the exosomes or cells and, subsequently, when the treated CSF is returned to the mammalian subject, the secreted factors released by the exosomes or cells packed in the cartridge 1515 may be distributed into the CSF and circulated through the brain and spinal cord.

Exosomes may also have a negative impact on a disease state, in certain instances. For example, exosomes may facilitate the transfer of misfolded proteins. The exosomes are also known to be able to penetrate the blood-brain barrier. In such an instance, these exosomes penetrating the blood-brain barrier should be removed or degraded from the CSF, thus reducing their impact on disease course. Studies have also found that the content of exosomes that are found in CSF can change in the presence of disease. In some implementations, the system 1500 may be used to remove unwanted exosomes or cells from the CSF.

Kit

Figure 19:
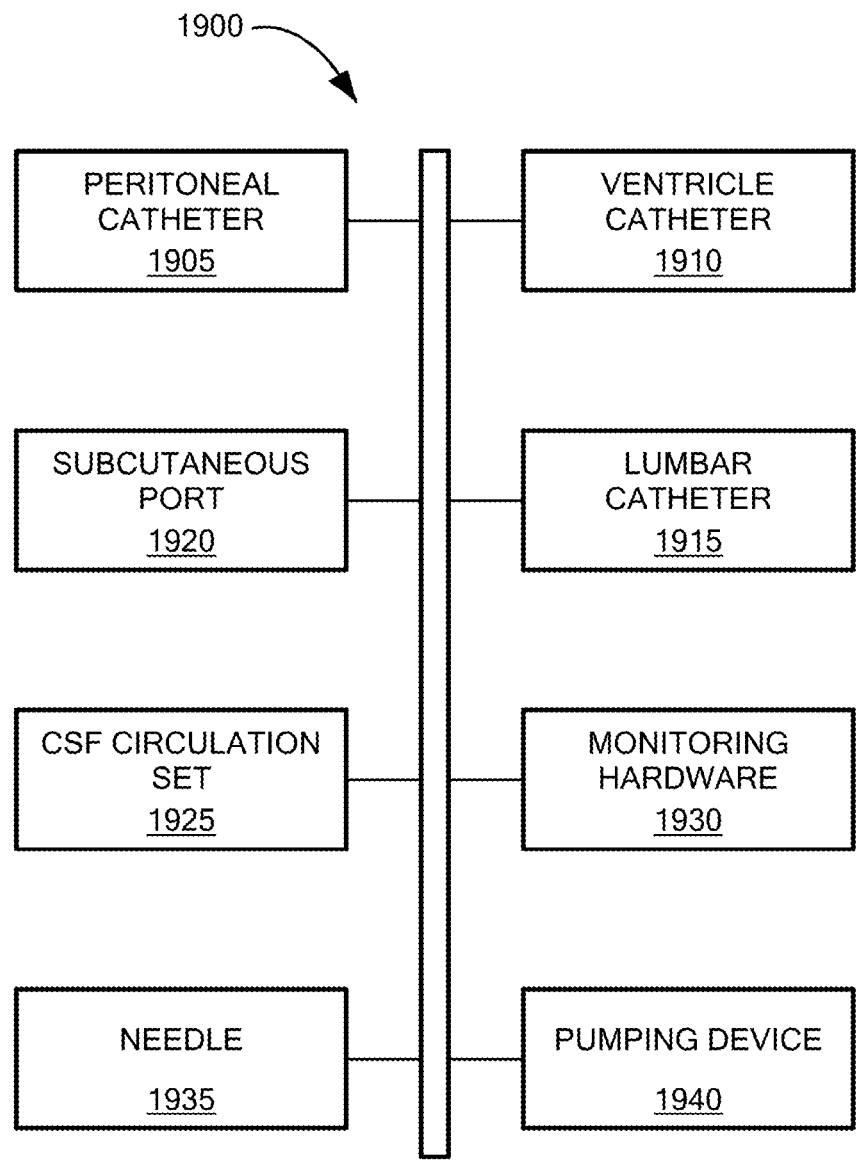
FIG. 19 shows a block diagram of an amelioration kit, in accordance with some embodiments of the present invention.

In some implementations of the various system and device embodiments described above, a packaged kit that includes desirable or necessary system components and sub-systems would be useful. Referring to FIG. 19, a block diagram of an exemplary kit 1900 is shown. In some implementations, the kit 1900 may include devices for a ventricle CSF line, a lumbar CSF line, a CSF circulation system or set 1925, monitoring hardware 1930, and a pumping device 1940. In some variations, the ventricle CSF line may include the following: a peritoneal catheter 1905, a ventricular catheter 1910, one or more catheter adapters, a subcutaneous access port 1920, and a subcutaneous access needle 1935. In some variations, the lumbar CSF line may include the following: a peritoneal catheter 1905, a lumbar catheter 1915, one or more catheter adapters, a subcutaneous access port 1920, and a subcutaneous access needle 1935. In some variations, a second peritoneal catheter 1905 and/or the peritoneal catheter 1905 may be optional, if the lumbar catheter 1915 can reach the lower abdomen of the subject, which would enable connecting the lumbar catheter 1915 directly to the subcutaneous access port 1920.

In some embodiments, the CSF circulation set 1925 may include a cartridge 1800 (FIG. 18), one or more pressure sensors (and/or other sensors), one or more sample ports, and pump-specific tubing. Advantageously, the cartridge 1800 may be packaged and stored separately. When the kit 1900 is needed, the cartridge 1800 may be added at POC. The pump-specific tubing in the CSF circulation set 1925 of the kit 1900 may be selected to be compatible with the pumping device (e.g., a peristaltic pump) 1940. The monitoring hardware 1930 may include a programmed programmable microprocessor having a touch-screen graphical user interface, random access memory, read-only memory, and a processing unit. Optionally, the monitoring hardware 1930 may include a cradle that may be structured and arranged to releasably attach the pumping device 1940 to the monitoring hardware 1930 (as shown in FIG. 15B) and for releasably attaching the monitoring hardware 1930 to a standard IV pole or similar fixture (as shown in FIG. 15A).

Various Advantages of Some Embodiments of the Present Invention

A significant advantage of variations and embodiments of the invention is the removal of toxic proteins from the CSF. Additional advantages and benefits are numerous. For example, a completely implanted device does not have to explicitly regulate pressure or temperature when the CSF remains within the body. Moreover, precise flow control is not required, because within the body there is a substantially no-net flow condition; hence, there is no CSF volume change within the body of the subject.

By completely implanting the structure, the structure is more sterile, more tolerable, more portable, and easier to maintain in that condition. With implanted structures, there is no fluid dead space nor is there extensive tubing that may be clogged.

When introducing a flexible structure into the SAS, its flexible nature may permit entry into the body via a smaller diameter opening.

In instances with no active pumping, the system may be more robust and simpler in its configuration. With monolithic implanted pumps, the moving parts may be combined into a single piece, which is simpler and potentially more robust than an external pump system.

Alternatively, advantages of an external system include the ability to rapidly and without great disturbance exchange, repair, or adjust the components, the ability to utilize non-biocompatible materials such as certain battery power sources, and the ability to readily configure to a larger capacity for filtration, flow or power for temperature or pressure control.

Because the course of therapy and treatment may likely be extensive, once low levels of, for example, DPRs in the CSF have been achieved, the present invention provides for chronic use for which its less invasive, implantable, ambulatory, low power, low maintenance, and non-constraining attributes are suitable.

Alternatively, once low levels of the target proteins are achieved, an ex corpore system may be detached to allow for patient mobility and, subsequently, reattached for additional treatment.

Embodiments of the present invention also enable focused or targeted flow to a specific area requiring therapy or treatment before the DPRs, for example, are able to affect other locations within the subject's body. For example, if a cell toxicity has been identified in the lumbar region, embodiments of the present invention may be implanted locally in the lumbar region, upstream or proximate to the source of the DPRs, to treat (i.e., focus on) the afflicted area. Such selectivity in locating the structure proximate to the specific area provides for zeroing in on the problem area while also reducing the spread of the toxin-induced damage through CSF mediated transport.

Advantageously, once the structure has been completely implanted, the structure may also be used to sample CSF at will or, alternatively, in a pseudo-continuous or periodic fashion. This feature facilitates chronic monitoring and treatment of the subject. Having a completely implanted structure in the subject may also constitute a stand-alone diagnostic tool.

Various combinations and permutations of the systems, sub-systems, components and associated treatment methods are contemplated and considered to be within the scope of the invention. For example, embodiments of the present invention may include an ex corpore method of treating neurological and non-neurological pathologies, neurological and non-neurological trauma, and/or neurological and non-neurological deficiencies. For example, in one embodiment, the present invention may be used to remove, e.g., by enzymatic digestion, toxic DPRs or other biomolecules from the CSF, thereby ameliorating neurological or non-neurological pathologies, neurological or non-neurological trauma, and/or neurological or non-neurological deficiencies such as, for the purpose of illustration rather than limitation: amyotrophic lateral sclerosis (ALS), Frontotemporal Degeneration (FTD), Progressive supranuclear palsy (PSP), Alzheimer disease (AD), Parkinson disease (PD), Huntington disease (HD), Guillain-Barré Syndrome (GBS), meningitis, cerebral vasospasm, a drug overdose, and so forth.

In some implementations, the method may include modifying one or more of a dynamic disposition, a kinetic disposition, and/or a spatial disposition of the biochemical milieu (e.g., fungi, spores, prions, peptides, bacteria, viruses, antigens, blood cells, toxic proteins, dissolved gases, inflammatory mediators, and so forth) and/or of the physical character (e.g., pH, volume, salinity, pressure, concentration, temperature, oncotic pressure, total protein content, and so forth) of the CSF in a mammalian subject (e.g., a human being). In some applications, the dynamic modification may include amelioration of (e.g., toxic) biomolecules within the CSF by one or more of: removing the CSF via a shunt, reducing the concentration of (e.g., toxic) biomolecules within the CSF, redistributing (e.g., toxic) biomolecules within the CSF, and/or focusing a flow pattern in the CSF. Some embodiments of dynamic modification may include a treatment method based on implementing physiochemical processes including one or more of: filtering, charge separation, exposure to ultraviolet light, exposure to infrared radiation, exposure to nuclear radiation, Raman scattering, dynamic light scattering, and the like. Kinetic modification may include influencing one or more of a flow rate, a local flow velocity, potential energy, and/or photonic or chemical excitation. Spatial modification may include treating biological, chemical, and/or molecular constituents. For example, such treatments for spatial modification purposes may include separation, degradation, sterilization, irradiation, immobilization, sequestration, aseptic separation, chemical reaction, molecular reconfiguration, de-aggregation, localized modification, combination of entities, and the like.

Dynamic modification may include a treatment method based on implementing a focused CSF flow. In some embodiments, the focused flow may be implemented such that the flow is operable to reduce the concentration of one or more target species (e.g., biomolecules) at a discrete target location(s). In other implementations, the focused flow may be implemented such that the flow may be operable to increase the concentration of the target species at a treatment location(s). In still other implementations, the focused flow may be implemented such that the flow may be operable to increase the transportation of the target species from one location to another location.

In some implementations involving focused flow, a conditioning cartridge or other structure containing an ameliorating agent may be located external to the subarachnoid space (SAS) while the CSF is actively pumped (e.g., via a plurality of catheters) to and through the external conditioning cartridge, and such that motor neuron locations are presented with a high circulation of CSF.

Spatial modification (e.g., modification of chemical constituents) may include introducing an ameliorating agent (e.g., an enzyme) operable to enzymatically (e.g., proteolytically) digest biomolecules within the CSF. In some implementations, the ameliorating agent may be introduced to CSF biomolecules within the SAS or outside of the SAS without circulation of the ameliorating agent. The CSF may selectively circulate naturally about the stationary or substantially stationary ameliorating agent, may be actively circulated, or may be passively circulated. In examples where the ameliorating agent is substantially stationary, the ameliorating agent may be disposed onto a (e.g., solid) substrate, for example, so that the ameliorating agent is decorated on the outer surface of a plurality of porous beads, on a porous monolithic structure contained within a cartridge, and the like. The cartridge enables the inflow of endogenous CSF which comes in contact with the ameliorating agent prior to exiting the cartridge. In some variations, spatial modification may include a combination of ameliorating processes and/or a combination of ameliorating agents. When the ameliorating agent is bound to the substrate, for example, the CSF may be filtered, subject to an ameliorating agent, and then filtered again. In some applications, spatial modification may include a combination of ameliorating processes plus focused flow and/or a combination of ameliorating agents plus focused flow.

Spatial modification (e.g., modification of chemical constituents) may include introducing and circulating an ameliorating agent operable to enzymatically (e.g., proteolytically) digest biomolecules within the CSF. In some implementations, the ameliorating agent may be: introduced and circulated entirely within the SAS, introduced and circulated in and out of the SAS, or may be introduced and circulated entirely outside of the SAS. For example, in some variations, the ameliorating agent may be formed on or decorated on the outer surface of a plurality of (e.g., superparamagnetic) beads that are disposed in-vivo (e.g., in the lumbar sac) as a slurry within a porous bag, a tubular device, and/or a dialysis-like (e.g., a dialysis membrane) catheter. The beads decorated with the ameliorating agent may be circulated (e.g., using magnetic attraction, by actively pumping, and so forth) within the SAS. The CSF may circulate naturally about the circulating ameliorating agent or may be actively or passively circulated.

A further embodiment may include an in-vivo treatment method that includes introducing or placing the ameliorating agent within the SAS (e.g., on a solid, collapsible or flexible substrate or within a tubular structure, cartridge, or catheter) without circulating the ameliorating agent. In various applications, the CSF may circulate naturally (e.g., by passive circulation) in the presence of the ameliorating agent, such that the CSF remains entirely within the SAS; the CSF may be circulated in the presence of the ameliorating agent by actively pumping the CSF entirely within the SAS; the CSF may be circulated in the presence of the ameliorating agent by passively pumping the CSF entirely within the SAS; or the CSF may be circulated in the presence of the ameliorating agent by actively or passively pumping the CSF, which may include pumping the CSF from and back into the SAS.

CSF may circulate in the presence of an (e.g., hydraulically- or pneumatically) inflatable substrate having a plurality of cilia projecting from the substrate or from a plurality of appendages incorporated into the substrate. Each of the cilia may be decorated with an ameliorating agent, such that, as the substrate cyclically expands and contracts, the CSF may be mixed and any biomolecules within the CSF may interact with (e.g., be enzymatically digested by) the ameliorating agent.

CSF may be circulated in the presence of an (e.g., hydraulically- or pneumatically) inflatable substrate having a plurality of outcropping appendages incorporated into the substrate. Each of the outcropping appendages may be decorated with an ameliorating agent, such that, as the substrate cyclically expands and contracts, the CSF may be mixed and any biomolecules within the CSF may interact with (e.g., be enzymatically digested by) the ameliorating agent on the outcropping appendages.

CSF may be circulated in the presence of a tubular-shaped structure having a plurality of fibers attached on the inside of the substrate. Each of the fibers may be decorated with an ameliorating agent and may extend from the inside of the structure and retract back into the structure. Biomolecules within the CSF may interact with (e.g., be enzymatically digested by) the ameliorating agent on the fibers in an extended state.

In variations, an ameliorating agent is applied to the exposed surfaces of a stent or a plate located within the SAS and circulating the CSF through the stent or across the plate. In some variations, the CSF is allowed to circulate naturally (e.g., by passive circulation) through the stent or across the plate. In other variations, the CSF may be circulated outside of the SAS and returned to the SAS before circulating through the stent or across the plate. Some embodiments of the present invention may include a treatment method that also includes a bulk flow system having a plurality of sensors and a number of pumps, valves, and/or actuators that are controllable by a system controller.

Other embodiments may include a method of treating a mammalian subject suffering from neurological or non-neurological pathologies, neurological or non-neurological trauma, or neurological or non-neurological deficiencies. In some embodiments, the method includes circulating CSF in a focused flow in a subject. In some applications, amelioration of the toxic biomolecules in the CSF using an ameliorating agent, an amelioration technique, or combinations thereof. In other implementations, no ameliorating agent is utilized. In some implementations, circulating CSF in a focused flow include: circulating CSF at natural flow levels, enabling CSF flow outside of the subarachnoid space, limiting CSF flow only within the subarachnoid space, and/or using a passive pump.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art, including all combinations and permutations of structural elements and method steps, without departing from the spirit and scope of the invention. Accordingly, the appended claims shall not be limited by the particular features that have been shown and described, but shall be construed also to cover modifications and equivalents thereof.

What is claim is:

1. A method for treating a mammalian subject suffering from at least one of a pathology, trauma, a neurological disease, a non-neurological disease, or a deficiency characterized by presence of toxic biomolecules in a cerebrospinal fluid (CSF) by amelioration of the toxic biomolecules in the CSF using an ameliorating agent, an amelioration technique, or combinations thereof, the method comprising:
    selecting a patient having at least one of a risk, a diagnosis, a prognosis, or at least one symptom of a condition selected from the group consisting of pathology, trauma, neurological disease, non-neurological disease, or deficiency;
    removing a volume of CSF from a first location of the patient at a flow rate between about 0.1 mL/min and about 100 mL/min, the first location located at a lateral ventricle of the patient;
    treating the removed volume of CSF;
    returning the treated volume of CSF to the patient at a second location, the second location located at a lumbar sac of the patient; and
    sensing measurable characteristics of the treated volume of CSF using one or more sensing devices as the treated volume of CSF is being returned to the patient, the measurable characteristics including an intracerebral pressure and an intrathecal pressure, wherein:
    the intracerebral pressure at the first location ranges from about 5 mm Hg to about 15 mm Hg, the intrathecal pressure at the second location ranges from about 5 mm Hg to about 15 mm Hg;
    using anti-backflow valves to control the flow of the CSF through one or more of the first location and the second location to substantially prevent backward fluid flow and to permit one or more of: priming, flushing, gas purging, or removal of occlusions; and
    the intracerebral pressure and the intrathecal pressure are each maintained within the ranges of from about 5 mm Hg to about 15 mm Hg.

2. The method of claim 1, wherein treating the removed volume of CSF comprises treating with a protease comprising a trypsin.

3. The method of claim 2, wherein the protease is bound to a resin.

4. The method of claim 3, where the resin comprises a porous resin.

5. The method of claim 3 wherein the resin comprises a porous bead that incorporates the protease.

6. The method of claim 3, where the resin comprises methacrylate.

7. The method of claim 3, where the resin comprises agarose.

8. The method of claim 1, wherein the neurological disease is selected from the group consisting of amyotrophic lateral sclerosis (ALS), Alzheimer disease (AD), frontotemporal degeneration (FfD), progressive supranuclear palsy (PSP), Huntington disease (HD), Parkinson disease (PD), cancer, intracranial metastatic disease (IMD), diabetes, type-3 diabetes, lupus, poisoning, trauma, chronic traumatic encephalopathy (CTE), bacterial meningitis, aneurysms, stroke, cerebral vasospasms, and traumatic brain injury.

9. The method of claim 1, wherein the neurological disease is ALS.

10. The method of claim 1, wherein treating the removed volume of CSF comprises at least one of removing, reducing, altering, sequestering, digesting, neutralizing, and deactivating one or more substances selected from the group consisting of: tau, cis p-tau, Abeta, TDP-43, SODI, DPRs, neurofilaments, and alpha-synuclein.

11. The method of claim 1, wherein the toxic biomolecules within the CSF includes TDP-43.

12. The method of claim 1, further comprising using a CSF fluid loop with a first access port and a second access port to remove the volume of CSF from the first location at the first access port and return the treated volume of CSF via the second access port.

13. The method of claim 12, wherein the CSF fluid loop comprises at least one sensor.

14. The method of claim 13, further comprising providing at least one of a pump, a valve, or an actuator located within the CSF fluid loop.

15. The method of claim 14, wherein the pump is selected from the group consisting of a peristaltic pump, a rotary vane pump, an Archimedes screw, an air bladder, a pneumatic bladder, a hydraulic bladder, a displacement pump, an electromotive pump, a passive pump, an autopump, a valveless pump, a bi-directional pump, and combinations thereof.

16. The method of claim 1, further comprising:
measuring a fluid characteristic;
determining whether the measured fluid characteristic meets a prescribed relationship to a predetermined threshold for a period of time;
updating at least one parameter of a set of treatment operational parameters as a function of said determining, the operational parameters being updated to maintain at least one of a specific volume change, or a specific flow rate within a CSF space of the patient.

17. The method of claim 1, wherein the ameliorating agent is a therapeutic substance.

18. The method of claim 17, wherein the therapeutic substance is a drug that includes secreted molecules having trophic factors or anti-inflammatory molecules, or genetically engineered to produce trophic factors or anti-inflammatory molecules.

19. The method of claim 1, wherein amelioration is performed by one or more of digestion, enzymatic digestion, filtration, size filtration, tangential flow filtering, countercurrent cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photoacoustic interactions, chemical treatments, thermal methods, and combinations thereof.

20. The method of claim 1, wherein the ameliorating agent includes one or more of enzymes, antibodies or antibody fragments, nucleic acids, receptors, anti-bacterial, anti-viral, antiDNA/RNA, protein/amino acid, carbohydrate, enzymes, isomerases, compounds with highlow biospecific binding affinity, aptamers, exosomes, ultraviolet light, temperature change, electric field, molecular imprinted polymers, or living cells.

21. The method of claim 1, wherein the ameliorating agent includes one or more of trypsin; elastase; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin, including the cathepsins E, S, B, K, or Ll; Tissue Type A; heparinase; granzymes, including granzyme A; meprin alpha; pepsin; endothiapepsin; kallikrein-6; kallikrein-5; pinl; and exosomes.

* * * * *